US012728159B2

(12) United States Patent
Baker et al.

(10) Patent No.: US 12,728,159 B2
(45) Date of Patent: Sep. 8, 2026

(54) CORONAVIRUS VACCINES COMPOSITIONS AND METHOD OF USING SAME

(71) Applicants: LOYOLA UNIVERSITY OF CHICAGO, Chicago, IL (US); THE UNITED STATES OF AMERICA, AS REPRESENTED BY THE SECRETARY OF AGRICULTURE, District of Columbia, WA (US)

(72) Inventors: Susan Baker, Elmhurst, IL (US); Xufang Deng, Lyons, IL (US); Kelly Milton Lager, Colo, IA (US); Kay Faaberg, Ames, IA (US); Alexandra DeVries, Ames, IA (US)

(73) Assignees: LOYOLA UNIVERSITY OF CHICAGO, Chicago, IL (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 826 days.

(21) Appl. No.: 17/914,293

(22) PCT Filed: Mar. 23, 2021

(86) PCT No.: PCT/US2021/023764

§ 371 (c)(1),
(2) Date: Sep. 23, 2022

(87) PCT Pub. No.: WO2021/195137

PCT Pub. Date: Sep. 30, 2021

(65) Prior Publication Data

US 2023/0117744 A1 Apr. 20, 2023

Related U.S. Application Data

(60) Provisional application No. 62/993,489, filed on Mar. 23, 2020.

(51) Int. Cl.

| | |
|---|---|
| ***A61K 39/00*** | (2006.01) |
| ***A61K 39/215*** | (2006.01) |
| ***A61P 31/14*** | (2006.01) |
| ***C12N 7/00*** | (2006.01) |

(52) U.S. Cl.

CPC ............ *A61K 39/215* (2013.01); *A61P 31/14* (2018.01); *C12N 7/00* (2013.01); *A61K 2039/5254* (2013.01); *A61K 2039/552* (2013.01); *A61K 2039/57* (2013.01); *C12N 2770/20021* (2013.01); *C12N 2770/20034* (2013.01)

(58) Field of Classification Search

CPC .......... A61K 39/215; A61K 2039/5254; A61K 2039/552; A61K 2039/57; A61K 39/12; A61P 31/14; C12N 9/127

See application file for complete search history.

(56) References Cited

U.S. PATENT DOCUMENTS

| | | | |
|---|---|---|---|
| 5,057,540 | A | 10/1991 | Kensil et al. |
| 5,273,965 | A | 12/1993 | Kensil et al. |
| 5,352,449 | A | 10/1994 | Beltz et al. |
| 5,443,829 | A | 8/1995 | Kensil et al. |
| 5,560,398 | A | 10/1996 | Pfleger |
| 5,679,356 | A | 10/1997 | Bonnem et al. |
| 2012/0283110 | A1 | 11/2012 | Shendure et al. |
| 2018/0333482 | A1 | 11/2018 | Baker et al. |

FOREIGN PATENT DOCUMENTS

| | | | |
|---|---|---|---|
| WO | 2016/012793 | A1 | 1/2016 |
| WO | WO2106012793 | * | 1/2016 |
| WO | 2018/160977 | A1 | 9/2018 |

OTHER PUBLICATIONS

Bouvet et al (JBC 289: p. 25783-796, 2014) (Year: 2014).*
Zheng et al (JBC 293: 12054-12067, 2018). (Year: 2019).*
Hou et al (JV 93:e00406, Aug. 2019, IDS dated Jul. 24, 2023, #17 (Year: 2019).*
Zhang et al (JV 92: e01677-17 Feb. 2018, IDS dated Jul. 24, 2023, #48), (Year: 2018).*
Deng et al (JV, 93: e02000-18, Apr. 2019, IDS dated Jul. 24, 2023, #9 (Year: 2019).*
Akira et al., Role of adapters in Toll-like receptor signalling, Bioch. Soc. Trans., 31:637-642 (2003).
Bhardwaj et al., The severe acute respiratory syndrome coronavirus Nsp15 protein is an endoribonuclease that prefers manganese as a cofactor, J. Virol., 78:12218-12224 (2004).
Boehm et al., Cellular responses to interferon-gamma, Ann. Rev. Immunol., 15:749-795 (1997).
Bolles et al., A double-inactivated severe acute respiratory syndrome coronavirus vaccine provides incomplete protection in mice and induces increased eosinophilic proinflammatory pulmonary response upon challenge, J. Virol., 85:12201-15 (2011).
Change et al., Granulocyte-macrophage colony stimulating factor: an adjuvant for cancer vaccines, Hematology, 9(3):207-215 (2004).
Channappanavar et al., Dysregulated Type I Interferon and Inflammatory Monocyte-Macrophage Responses Cause Lethal Pneumonia in SARS-CoV-Infected Mice, Cell Host Microbe., 19:181-193 (2016).
Channappanavar et al., IFN-I response timing relative to virus replication determines MERS coronavirus infection outcomes, J. Clin. Invest., 129:3625-3639 (2019).
Deng et al., An "Old" protein with a new story: Coronavirus endoribonuclease is important for evading host antiviral defenses, Virology, 517:157-163 (2018).
Deng et al., Coronavirus Endoribonuclease Activity in Porcine Epidemic Diarrhea Virus Suppresses Type I and Type III Interferon Responses, J. Virol., 93:e02000-18 (2019).

(Continued)

*Primary Examiner* — Lei Yao

(74) *Attorney, Agent, or Firm* — MARSHALL, GERSTEIN & BORUN LLP

(57) ABSTRACT

The present disclosure provides compositions, for example vaccine compositions comprising live, attenuated coronavirus. The disclosure also provides methods of using coronavirus vaccines, including methods of treating and/or preventing coronavirus infections, and provides methods of preparing coronavirus vaccines.

8 Claims, 22 Drawing Sheets

Specification includes a Sequence Listing.

(56) References Cited

OTHER PUBLICATIONS

Deng et al., Coronavirus nonstructural protein 15 mediates evasion of dsRNA sensors and limits apoptosis in macrophages, Proc. Natl. Acad. Sci. USA., 114:E4251-E4260 (2017).
Dranoff, GM-CSF-based cancer vaccines, G. Immunol. Rev., 188:147-154 (2002).
Du et al., Genome-wide identification of interferon-sensitive mutations enables influenza vaccine design, Science, 359:290-296 (2018).
Fung et al., A tug-of-war between severe acute respiratory syndrome coronavirus 2 and host antiviral defence: lessons from other pathogenic viruses, Emerging Microbes & Infections, 9(1):558-570 (2020).
Graham, et al., SARS coronavirus replicase proteins in pathogenesis, Virus Research, 133(1):88-100 (2008).
Hackbart et al., Coronavirus endoribonuclease targets viral polyuridine sequences to evade activating host sensors, Proc. Natl. Acad. Sci., 117:8094-8103 (2020).
Holshue et al., First Case of 2019 Novel Coronavirus in the United States, N. Engl. J. Med., 382:929-936 (2020).
Hou et al., Engineering a Live Attenuated Porcine Epidemic Diarrhea Virus Vaccine Candidate via Inactivation of the Viral 2'-O-Methyltransferase and the Endocytosis Signal of the Spike Protein, J. Virol., 93:e00406-19 (2019).
Huang et al., Clinical features of patients infected with 2019 novel coronavirus in Wuhan, China, Lancet, 395:497-506 (2020).
International Application No. PCT/US21/23764, International Preliminary Report on Patentability, mailed Oct. 6, 2022.
International Application No. PCT/US21/23764, International Search Report and Written Opinion, mailed Jul. 6, 2021.
Ivanov et al., Major genetic marker of nidoviruses encodes a replicative endoribonuclease, Proc. Natl. Acad. Sci. USA., 101:12694-12699 (2004).
Kindler et al., To sense or not to sense viral RNA—essentials of coronavirus innate immune evasion, Curr. Opin. Microbiol., 20:69-75 (2014).
Lin et al., Present status of the use of cytokines as adjuvants with vaccines to protect against infectious diseases, Clin. Infec. Dis., 21(6):1439-1449 (1995).
Marazzi et al., Interference of viral effector proteins with chromatin, transcription, and the epigenome, Curr. Opin. Microbiol., 26:123-9 (2015).
Menachery et al., Combination Attenuation Offers Strategy for Live Attenuated Coronavirus Vaccines, J. Virol., 92:e00710-18 (2018).
Menachery et al., MERS-CoV Accessory ORFs Play Key Role for Infection and Pathogenesis, Mbio, 8:e00665-17 (2017).
Menachery et al., Middle East Respiratory Syndrome Coronavirus Nonstructural Protein 16 Is Necessary for Interferon Resistance and Viral Pathogenesis, mSphere, 2:e00346-17 (2017).
Mesev et al., Decoding type I and III interferon signalling during viral infection, Nat. Microbiol., 4:914-924 (2019).
Miller et al., Evaluation of two real-time polymerase chain reaction assays for Porcine epidemic diarrhea virus (PEDV) to assess PEDV transmission in growing pigs, J. Vet. Diagnostic Investig, 28:20-29 (2016).
Narayanan et al., Coronavirus nonstructural protein 1: Common and distinct functions in the regulation of host and viral gene expression, Virus Res, 202:89-100 (2015).
Nelson, IL-2, regulatory T cells, and tolerance, J. Immunol., 172(7):3983-3988 (2004).
Okda et al., Development of an indirect ELISA, blocking ELISA, fluorescent microsphere immunoassay and fluorescent focus neutralization assay for serologic evaluation of exposure to North American strains of Porcine Epidemic Diarrhea Virus, BMC Vet. Res., 11:180 (2015).
Perlman et al., Coronaviruses post-SARS: update on replication and pathogenesis, Nat. Rev. Microbiology, 7:439-450 (2009).
Portielje et al., IL-12: a promising adjuvant for cancer vaccination, Cancer Immunol. Immunother., 52(3):133-144 (2003).
Reed et al., A Simple Method of Estimating Fifty Per Cent Endpoints, Am. J. Epidemiol., 27:493-497 (1938).
Ricagno et al., Crystal structure and mechanistic determinants of SARS coronavirus nonstructural protein 15 define an endoribonuclease family, Proc. Natl. Acad. Sci., 103:11892-11897 (2006).
Smith et al., How Does Vaccinia Virus Interfere With Interferon?, Adv. Virus Res., 100:355-378 (2018).
Smith et al., Vaccinia virus immune evasion: mechanisms, virulence and immunogenicity, J. Gen. Virol., 94:2367-2392 (2013).
Snijyder et al., Unique and conserved features of genome and proteome of SARS-coronavirus, an early split-off from the coronavirus group 2 lineage, Journal of Molecular Biology, 331:991-1004 (2003).
Taylor, Cytokines as adjuvants for vaccines: antigen-specific responses differ from polyclonal responses, Infect. Immun., 63(9):3241-3244 (1995).
Theofilopoulos et al., Type I interferons (alpha/beta) in immunity and autoimmunity, Ann. Rev. Immunol., 23:307-336 (2005).
Trinchieri, Interleukin-12 and the regulation of innate resistance and adaptive immunity, Nat. Rev. Immunol., 3(2):133-146 (2003).
Volk et al., Coronavirus Endoribonuclease and Deubiquitinating Interferon Antagonists Differentially Modulate the Host Response during Replication in Macrophages, J. Virology, 94(11):e00178-20 (2020).
Wang et al., Emerging and re-emerging coronaviruses in pigs, Current Opinion in Virology, 34:39-49 (2019).
Wu et al., A new coronavirus associated with human respiratory disease in China, Nature, 579: 265-271 (Mar. 2020).
Xu et al., Characteristics of pediatric SARS-CoV-2 infection and potential evidence for persistent fecal viral shedding, Nat. Med., 26:502-504 (2020).
Xu et al., New antiviral target revealed by the hexameric structure of mouse hepatitis virus nonstructural protein nsp15, J. Virol., 80:7909-7917 (2006).
Zhang et al., Type III Interferon Restriction by Porcine Epidemic Diarrhea Virus and the Role of Viral Protein nsp1 in IRF1 Signaling, J. Virol., 92:e01677-17 (2018).
Zhang, Q., et al., Suppression of type I interferon production by porcine epidemic diarrhea virus and degradation of CREB-binding protein by nspl, Virology, 489:252-268 (2016).
Zhao et al., Antagonism of the interferon-induced OAS-RNase L pathway by murine coronavirus ns2 protein is required for virus replication and liver pathology, Cell Host & Microbe, 11:607-616 (2012).
Zheng et al., Insight into the evolution of nidovirus endoribonuclease based on the finding that nsp15 from porcine Deltacoronavirus functions as a dimer, Journal of Biological Chemistry, 293(31):12054-12067 (2018).
Zhou et al., A pneumonia outbreak associated with a new coronavirus of probable bat origin, Nature, 579:270-273 (2020).
Zhu et al., A Novel Coronavirus from Patients with Pneumonia in China, 2019, N. Engl. J. Med., 382:727-733 (2020).
Zust et al., Ribose 2'-O-methylation provides a molecular signature for the distinction of self and non-self mRNA dependent on the RNA sensor Mda5, Nat. Immunol., 12:137-43 (2011).

* cited by examiner

A

B

| Virus strains | Positions targeted for mutation | | | References |
|---|---|---|---|---|
| icPEDV-WT | Nsp1<br>$_{422}$TTC$_{424}$<br>(F44) | Nsp15<br>$_{19390}$CAC$_{19392}$ (H226)<br>$_{19435}$CAT$_{19437}$ (H241) | Nsp16<br>$_{20116}$GAT$_{20118}$<br>(D129) | Deng et al. 2019 |
| icPEDV-Nsp1mt | GGC<br>(F44A) | WT | WT | Zhang et al. 2018;<br>This study |
| icPEDV-EnUmt | WT | GCC (H226A) | WT | Deng et al. 2019 |
| icPEDV-Nsp16mt | WT | WT | GCA (D129A) | Hou et al. 2019;<br>This study |
| icPEDV-mut4 | GGC (F44A) | GCC (H226A)<br>GCC (H241A) | GCA (D129A) | This study |

Figure 7A icPEDV-WT sequence (SEQ ID NO: 34)

ACTTAAAGAGATTTTCTATCTACGGATAGTTAGCTCTTTTTCTAGACTCTTGTCTACTCAATTCAACTAA
ACGAAATTTTGTCCTTCCGGCCGCATGTCCATGCTGCTGGAAGCTGACGTGGAATTTCATTAGGTTTGCT
TAAGTAGCCATCGCAAGTGCTGTGCTGTCCTCTAGTTCCTGGTTGGCGTTCCGTCGCCTTCTACATACTA
GACAAACAGCCTTCCTCCGGTTCCGTCTGGGGGTTGTGTGGATAACTAGTTCTGTCTAGTTTGAAACCAG
TAACTGTCGGCTATGGCTAGCAACCATGTTACATTGGCTTTTGCCAATGATGCAGAAATTTCAGCTTTTG
GCTTTTGCACTGCTAGTGAAGCCGTCTCATACTATTCTGAGGCCGCCGCTAGTGGATTTATGCAATGCCG
TTTCGTGTCCTTCGATCTCGCTGACACTGTTGAGGGATTGCTTCCCGAAGACTATGTCATGGTGGTGGTC
GGCACTACCAAGCTTAGTGCGTATGTGGACACTTTTGGTAGCCGCCCCAAAAACATTTGTGGTTGGCTGT
TATTTTCTAACTGTAATTACTTCCTCGAAGAGTTAGAGCTTACTTTTGGTCGTCGTGGTGGTAACATCGT
GCCAGTTGACCAATACATGTGTGGCGCTGACGGTAAACCTGTTCTTCAGGAATCCGAATGGGAGTATACA
GATTTCTTTGCTGACTCCGAAGACGGTCAACTCAACATTGCTGGTATCACTTATGTGAAGGCCTGGATTG
TAGAGCGATCGGATGTCTCTTATGCGAGTCAGAATTTAACATCTATTAAGTCTATTACTTACTGTTCAAC
CTATGAGCATACTTTTCCTGATGGTACTGCCATGAAGGTTGCACGTACTCCAAAGATTAAGAAGACTGTT
GTCTTGTCTGAGCCACTTGCTACTATCTACAGGGAAATTGGTTCTCCTTTTGTGGATAATGGGAGCGATG
CTCGTTCTATCATTAAGAGACCAGTGTTCCTCCACGCTTTTGTTAAGTGTAAGTGTGGTAGTTATCATTG
GACTGTTGGTGATTGGACTTCCTATGTCTCCACTTGCTGTGGCTTTAAGTGTAAGCCAGTCCTTGTGGCT
TCATGCTCTGCTACGCCTGGTTCTGTTGTGGTTACGCGCGCTGGTGCTGGCACTGGTGTTAAGTATTACA
ACAACATGTTCCTGCGCCATGTGGCAGACATTGATGGGTTGGCATTCTGGCGAATTCTCAAGGTGCAGTC
CAAAGACGACCTCGCTTGCTCTGGTAAATTCCTTGAACACCATGAGGAAGGTTTCACAGATCCTTGCTAC
TTTTTGAATGACTCGAGCATTGCTACTAAGCTCAAGTTTGACATCCTTAGTGGCAAGTTTTCTGATGAAG
TCAAACAAGCTATCTTTGCTGGTCATGTTGTTGTTGGCAGCGCGCTCGTTGACATTGTTGACGATGCACT
GGGACAGCCTTGGTTTATACGTAAGCTTGGTGACCTTGCAAGTGCAGCTTGGGAGCAGCTTAAGGCTGTC
GTTAGAGGCCTTAACCTCCTGTCTGATGAGGTCGTGCTCTTTGGCAAAAGACTTAGCTGTGCCACTCTTA
GTATCGTTAACGGTGTTTTTGAGTTCATCGCCGAAGTGCCTGAGAAGTTGGCTGCGGCTGTTACAGTTTT
TGTCAACTTCTTGAATGAGCTTTTTGAGTCTGCCTGTGACTGCTTAAAGGTCGGAGGTAAAACCTTTAAC
AAGGTTGGCTCTTATGTTCTTTTTGACAACGCATTGGTTAAGCTTGTCAAGGCAAAAGTTCGCGGCCCAC
GACAGGCAGGTGTTTGTGAAGTTCGTTACACAAGCCTTGTTATTGGGAGTACTACCAAGGTGGTTTCCAA
GCGCGTTGAAAATGCCAATGTGAATCTCGTCGTCGTTGACGAGGATGTGACCCTCAACACCACTGGTCGT
ACAGTTGTTGTTGACGGACTTGCATTCTTCGAGAGTGACGGGTTTTACAGACATCTTGCTGATGCTGACG
TTGTCATTGAACATCCTGTTTATAAGTCTGCTTGTGAGCTCAAGCCAGTTTTTGAGTGTGACCCAATACC
TGATTTTCCTATGCCTGTGGCCGCTAGTGTTGCAGAGCTTTGTGTGCAAACTGATCTGTTGCTTAAAAAT
TACAACACTCCTTATAAAACTTACAGCTGCGTTGTGAGAGGTGATAAGTGTTGTATCACTTGCACCTTAC
ATTTCACAGCACCAAGTTATATGGAGGCTGCTGCTAATTTTGTAGACCTCTGTACCAAGAACATTGGTAC
TGCTGGTTTTCATGAGTTTTACATTACGGCCCATGAACAACAGGATCTGCAAGGGTTCGTAACCACTTGT
TGCACGATGTCAGGTTTTGAGTGTTTTATGCCTATAATCCCACAGTGTCCAGCAGTGCTTGAAGAGATTG
ATGGTGGTAGCATCTGGCGGTCTTTTATCACTGGTCTTAATACAATGTGGGATTTTTGCAAGCATCTTAA
AGTCAGCTTTGGACTAGATGGCATTGTTGTCACTGTAGCACGCAAATTTAAACGACTTGGTGCTCTCTTG
GCAGAAATGTATAACACTTACCTTTCAACTGTGGTGGAAAACTTGGTACTGGCCGGTGTTAGCTTCAAGT
ATTATGCCACCAGTGTCCCAAAAATTGTTTTGGGCTGTTGTTTTCACAGTGTTAAAAGTGTTCTTGCAAG
TGCCTTCCAGATTCCTGTCCAGGCAGGCGTTGAGAAGTTTAAAGTCTTCCTTAACTGTGTTCACCCTGTT
GTACCACGTGTCATTGAAACTTCTTTTGTGGAATTAGAAGAGACGACATTTAAACCACCAGCACTCAATG
GTAGTATTGCTATTGTTGATGGCTTTGCTTTCTATTATGATGGAACACTATACTATCCCACCGATGGTAA
TAGCGTTGTTCCTATCTGCTTTAAGAAGAAAGGTGGTGGTGATGTCAAATTCTCTGATGAAGTCTCTGTT
AAAACCATTGACCCAGTTTATAAGGTCTCCCTTGAATTTGAGTTCGAGTCTGAGACTATTATGGCTGTGC
TTAATAAGGCTGTTGGTAATTGTATCAAGGTTACAGGTGGTTGGGACGATGTTGTTGAGTATATCAATGT
TGCCATTGAGGTTCTTAAAGATCACATCGATGTGCCTAAGTACTACATCTATGATGAGGAAGGTGGCACC
GATCCTAATCTGCCCGTAATGGTTTCTCAGTGGCCGTTGAATGATGACACGATCTCACAGGATCTGCTTG

Figure 7A (cont.)

ATGTTGAAGTTGTTACTGATGCGCCAGTTGATTTCGAGGGTGATGAAGTAGACTCCTCTGACCCTGATAA
GGTGGCAGACGTGGCTAACTCTGAGCCTGAGGATGACGGTCTTAATGTAGCTCCTGAAACAAATGTAGAG
TCTGAAGTTGAGGAAGTTGCCGCAACCTTGTCCTTTATTAAAGATACACCTTCCACAGTTACTAAGGATC
CTTTTGCTTTTGACTTTGCAAGCTATGGAGGACTTAAGGTTTTAAGACAATCTCATAACAACTGCTGGGT
TACTTCTACCTTGGTGCAGCTACAATTGCTTGGCATCGTTGATGACCCTGCAATGGAGCTTTTTAGTGCT
GGTAGAGTTGGTCCAATGGTTCGCAAATGCTATGAGTCACAAAAGGCTATCTTGGGATCTTTGGGTGATG
TGTCGGCTTGCCTAGAGTCTCTGACTAAGGACCTACACACACTTAAGATTACCTGTTCTGTAGTCTGTGG
TTGTGGTACTGGTGAACGTATCTATGATGGTTGTGCTTTTCGTATGACGCCAACTTTGGAACCGTTCCCA
TATGGTGCTTGTGCTCAGTGTGCTCAAGTTTTGATGCACACTTTTAAAAGTATTGTTGGCACCGGCATCT
TTTGTCGAGATACTACTGCTCTCTCCTTGGATTCTTTGGTTGTAAAACCTCTTTGTGCGGCTGCTTTTAT
AGGCAAGGATAGTGGTCATTATGTCACTAACTTTTATGATGCCGCTATGGCTATTGATGGTTATGGTCGT
CATCAGATAAAGTATGACACACTGAACACTATTTGTGTTAAAGACGTTAATTGGACAGCACCTTTTGTCC
CAGACGTTGAGCCTGTATTGGAGCTTGTTGTCAAACCTTTCTATTCTTATAAGAATGTTGATTTTTACCA
AGGAGATTTTAGTGACCTTGTTAAACTTCCATGTGATTTTGTTGTTAATGCTGCAAATGAGAATTTGTCT
CACGGTGGCGGCATAGCAAAGGCCATTGATGTTTATACCAAGGGCATGTTGCAGAAGTGCTCGAATGATT
ACATTAAAGCACACGGTCCCATTAAAGTTGGACGTGGTGTCATGTTGGAGGCATTAGGTCTTAAGGTCTT
TAATGTTGTTGGTCCACGTAAGGGTAAGCATGCACCTGAGCTTCTTGTTAAGGCTTATAAGTCCGTTTTT
GCTAATTCAGGTGTTGCTCTTACACCTTTGATTAGTGTTGGAATTTTTAGTGTTCCTTTGGAAGAATCTT
TATCTGCTTTTCTTGCATGTGTTGGTGATCGCCACTGTAAGTGCTTTTGTTATAGTGACAAAGAGCGCGA
GGCGATCATTAATTACATGGATGGCTTGGTAGATGCTATTTTCAAAGATGCACTTGTTGATACTACTCCT
GTCCAGGAAGATGTTCAACAAGTTTCACAAAAACCAGTTTTGCCTAATTTTGAACCTTTCAGGATTGAAG
GTGCTCATGCTTTCTATGAGTGCAACCCTGAAGGTTTGATGTCATTAGGTGCTGACAAGCTGGTGTTGTT
TACAAATTCCAATTTGGATTTTTGTAGCGTTGGTAAGTGTCTTAACAATGTGACTGGCGGTGCATTGCTT
GAAGCCATAAATGTATTTAAAAAGAGTAACAAAACAGTGCCTGCTGGCAACTGTGTTACTTTTGAGTGTG
CAGATATGATTTCTATTACTATGGTAGTATTGCCATCTGACGGTGATGCTAATTATGACAAAAATTATGC
ACGCGCCGTCGTCAAGGTATCTAAGCTTAAAGGCAAGTTATTGCTTGCTGTTGGTGATGCCATGTTGTAT
TCCAAGTTGTCCCACCTCAGCGTGTTAGGTTTCGTATCCACACCTGATGATGTGGAGCGTTTCTACGCAA
ATAAGAGTGTGGTTATTAAAGTTACTGAGGATACACGTAGTGTTAAGACTGTTAAAGTAGAATCCACTGT
TACTTATGGACAACAAATTGGACCTTGTCTTGTTAATGACACCGTTGTCACAGACAACAAACCTGTTGTT
GCTGATGTTGTAGCTAAGGTTGTACCAAGTGCTAATTGGGATTCACATTATGGTTTTGATAAGGCTGGTG
AGTTCCACATGCTAGACCATACTGGGTTTGCCTTTCCTAGTGAAGTTGTTAACGGTAGGCGTGTGCTTAA
AACCACAGATAATAACTGTTGGGTTAATGTTACATGTTTACAATTACAGTTTGCTAGATTTAGGTTCAAG
TCAGCAGGTCTACAGGCTATGTGGGAGTCCTATTGTACTGGTGATGTTGCTATGTTTGTGCATTGGTTGT
ACTGGCTTACTGGTGTTGACAAAGGTCAGCCTAGTGATTCAGAAAATGCACTTAACATGTTGTCTAAGTA
CATTGTTCCTGCTGGTTCTGTCACTATTGAACGTGTCACGCATGACGGTTGTTGTTGTAGTAAGCGTGTT
GTCACTGCACCAGTTGTGAATGCTAGCGTGTTGAAGCTTGGCGTCGAGGATGGTCTTTGTCCACATGGTC
TTAACTACATTGACAAAGTTGTTGTAGTTAAAGGTACTACAATTGTTGTCAATGTTGGAAAACCTGTAGT
GGCACCATCGCACCTCTTTCTTAAGGGTGTTTCCTACACAACATTCCTAGATAATGGTAACGGTGTTGCC
GGCCATTATACTGTTTTTGATCATGACACTGGTATGGTGCATGATGGAGATGTTTTTGTACCAGGTGATC
TCAATGTGTCTCCTGTTACAAATGTTGTCGTCTCAGAGCAGACGGCTGTTGTGATTAAAGACCCTGTGAA
GAAAGTAGAGTTAGACGCTACAAAGCTGTTAGACACTATGAATTATGCATCGGAAAGATTCTTTTCCTTT
GGTGATTTTATGTCACGTAATTTAATTACAGTGTTTTTGTACATCCTTAGTATTTTGGGTCTCTGTTTTA
GGGCCTTTCGTAAGAGGGATGTTAAAGTTCTAGCTGGTGTACCCCAACGTACTGGTATTATATTGCGTAA
AAGTGTGCGCTATAATGCAAAGGCTTTGGGTGTCTTCTTCAAGCTAAAACTTTATTGGTTCAAAGTTCTT
GGTAAGTTTAGTTTGGGTATTTATGCATTGTATGCATTACTATTCATGACAATACGCTTTACACCTATAG
GTGGCCCTGTTTGTGATGATGTTGTTGCTGGTTATGCTAATTCTAGTTTTGACAAGAATGAGTATTGCAA
CAGTGTTATTTGTAAGGTCTGTCTCTATGGGTACCAGGAACTTTCGGACTTCTCTCACACACAGGTAGTA
TGGCAACACCTTAGAGACCCATTAATTGGTAATGTGATGCCTTTCTTTTATTTGGCATTTCTGGCAATTT
TTGGGGGTGTTTATGTAAAGGCTATTACTCTCTATTTTATTTTCCAGTATCTTAACATACTTGGTGTGTT
TTTGGGCCTACAACAGTCCATTTGGTTTTTGCAGCTTGTGCCTTTTGATGTCTTTGGTGACGAGATCGTC
GTCTTTTTCATCGTTACACGCGTATTGATGTTCCTTAAGCATGTTTTCCTTGGCTGCGATAAGGCATCTT
GTGTGGCTTGCTCTAAGAGTGCTCGCCTTAAGCGCGTTCCTGTCCAGACTATTTTTCAGGGTACTAGCAA

Figure 7A (cont.)

ATCCTTCTACGTACATGCCAATGGTGGTTCTAAGTTCTGTAAGAAGCACAATTTCTTTTGTTTAAATTGT
GATTCTTATGGTCCAGGCTGCACTTTTATTAATGACGTCATTGCAACTGAAGTTGGTAATGTTGTCAAAC
TTAATGTGCAACCGACAGGTCCTGCCACTATTCTTATTGACAAGGTTGAATTCAGTAATGGTTTTTACTA
TCTTTATAGTGGTGACACATTTTGGAAGTACAACTTTGACATAACAGATAACAAATACACTTGCAAAGAG
TCACTTAAAAATTGTAGCATAATCACAGACTTTATTGTTTTTAACAATAATGGTTCCAATGTAAATCAGG
TTAAGAATGCATGTGTGTATTTTTCACAGATGCTTTGTAAACCTGTTAAGTTAGTGGACTCAGCGTTGTT
GGCCAGTTTGTCTGTTGATTTTGGTGCAAGCTTACATAGTGCTTTTGTTAGTGTGTTGTCGAATAGTTTT
GGCAAAGACCTGTCAAGTTGTAATGACATGCAGGATTGCAAGAGCACATTGGGTTTTGATGATGTACCAT
TGGATACCTTTAATGCTGCTGTTGCTGAGGCTCATCGTTACGATGTCCTCTTGACTGACATGTCGTTCAA
CAATTTTACCACCAGTTATGCAAAACCAGAGGAAAAACTTCCCGTCCATGACATTGCCACGTGTATGCGT
GTAGGTGCCAAGATTGTTAATCATAACGTTCTTGTCAAGGATAGTATACCTGTGGTGTGGCTTGTACGTG
ATTTCATTGCCCTTTCTGAAGAAACTAGGAAGTACATTATTCGTACGACTAAAGTTAAGGGTATAACCTT
CATGTTGACCTTTAATGATTGTCGTATGCATACTACCATACCTACTGTTTGCATTGCAAATAAGAAGGGT
GCAGGTCTTCCTAGTTTTTCAAAGGTTAAGAAATTCTTCTGGTTTTTGTGTCTGTTCATAGTTGCTGTTT
TCTTTGCACTAAGCTTTTTTGATTTTAGTACTCAGGTTAGCAGTGATAGTGATTATGACTTCAAGTATAT
TGAGAGTGGCCAGTTGAAGACTTTTGACAATCCACTTAGTTGTGTGCATAATGTCTTTAGTAACTTCGAC
CAGTGGCATGATGCCAAGTTTGGTTTCACCCCCGTCAACAATCCTAGTTGTCCTATAGTCGTTGGTGTAT
CAGACGAAGCGCGCACTGTTCCAGGTATCCCAGCAGGTGTTTATTTAGCTGGTAAAACACTTGTTTTTGC
TATTAACACCATTTTTGGTACATCTGGTTTGTGCTTTGATGCTAGTGGCGTTGCTGATAAGGGCGCTTGC
ATTTTTAATTCGGCTTGCACCACATTATCTGGTTTGGGTGGAACTGCTGTCTACTGTTATAAGAATGGTC
TAGTTGAAGGTGCTAAACTTTATAGTGAGTTGGCACCTCATAGCTACTATAAAATGGTAGATGGTAATGC
TGTGTCTTTACCTGAAATTATCTCACGCGGCTTTGGCATCCGTACTATCCGTACAAAGGCTATGACCTAC
TGTCGCGTTGGCCAGTGTGTGCAATCTGCAGAAGGTGTTTGTTTTGGCGCCGATAGATTCTTTGTCTATA
ATGCAGAATCTGGTTCTGACTTTGTTTGTGGCACAGGGCTCTTTACATTGTTGATGAACGTTATTAGTGT
TTTTTCCAAGACAGTACCAGTAACTGTGTTGTCTGGTCAAATACTTTTTAATTGCATTATTGCTTTTGCT
GCTGTTGCGGTGTGTTTCTTATTTACAAAGTTTAAGCGCATGTTCGGTGATATGTCTGTTGGCGTTTTCA
CTGTCGGTGCTTGTACTTTGTTGAACAATGTTTCCTACATTGTAACACAGAACACACTTGGCATGTTGGG
CTATGCAACTTTGTACTTTTTGTGCACTAAAGGTGTTAGATATATGTGGATTTGGCATTTGGGATTTTTG
ATCTCATATATACTTATTGCACCATGGTGGGTTTTGATGGTTTATGCCTTTTCAGCCATTTTTGAGTTTA
TGCCTAACCTTTTTAAGCTTAAGGTTTCAACACAACTTTTTGAGGGTGACAAGTTCGTAGGCTCTTTTGA
AAATGCTGCAGCAGGTACATTTGTGCTTGATATGCATGCCTATGAGAGACTTGCCAACTCTATCTCAACT
GAAAAACTGCGTCAGTATGCTAGTACTTACAATAAGTACAAGTATTATTCAGGCAGTGCTTCAGAGGCTG
ATTACAGGCTTGCTTGTTTTGCCCATTTGGCCAAGGCTATGATGGATTATGCTTCTAATCACAACGACAC
GTTATACACACCACCCACTGTGAGTTACAATTCAACTCTACAGGCTGGCTTGCGTAAGATGGCACAACCA
TCTGGTGTTGTTGAGAAGTGCATAGTTCGTGTTTGCTATGGTAATATGGCTCTTAATGGCCTATGGCTTG
GTGATACTGTTATCTGCCCACGCCATGTTATAGCGTCTAGTACTACTAGCACTATAGATTATGACTATGC
CCTTTCTGTTTTACGCCTCCACAACTTCTCCATTTCATCTGGTAATGTTTTCCTAGGTGTTGTGGGTGTA
ACCATGCGAGGTGCTTTGTTGCAGATAAAGGTTAATCAAAACAATGTCCACACGCCTAAGTACACCTATC
GCACAGTTAGACCGGGTGAATCTTTTAATATCTTGGCGTGCTATGATGGTTCTGCAGCTGGTGTTTACGG
CGTTAACATGCGCTCTAATTACACTATTAGAGGCTCGTTCATTAATGGCGCTTGTGGTTCACCTGGTTAT
AACATTAACAATGGTACCGTTGAGTTTTGCTATTTACACCAGCTTGAACTTGGTTCAGGCTGTCATGTTG
GTAGCGACTTAGATGGTGTTATGTATGGTGGTTATGAGGACCAACCTACTTTGCAAGTTGAAGGCGCTAG
TAGTCTGTTTACAGAGAATGTGTTGGCATTTCTTTATGCAGCACTCATTAATGGTTCTACCTGGTGGCTT
AGTTCTTCTAGGATTGCTGTAGACAGGTTTAATGAGTGGGCTGTTCATAATGGTATGACAACAGTAGTTA
ATACTGATTGCTTTTCTATTCTTGCTGCTAAGACTGGTGTTGATGTACAACGTTTGTTGGCCTCAATCCA
GTCTCTGCATAAGAATTTTGGTGGAAAGCAAATTCTTGGCTATACCTCGTTGACAGATGAGTTTACTACA
GGTGAAGTTATACGTCAAATGTATGGCGTTAATCTTCAGAGTGGTTATGTTTCACGCGCCTGTAGAAATG
TCTTGCTGGTTGGTTCTTTTCTGACTTTCTTTTGGTCAGAATTAGTTTCCTACACTAAGTTCTTTTGGGT
AAATCCTGGTTATGTCACACCTATGTTTGCGTGTTTGTCATTGCTGTCCTCACTTTTGATGTTCACACTC
AAGCATAAGACATTGTTTTTCCAGGTCTTTCTAATACCTGCTCTGATTGTTACATCTTGCATTAATTTGG
CATTTGATGTTGAAGTCTACAACTATTTGGCAGAGCATTTTGATTACCATGTTTCTCTCATGGGTTTTAA
TGCACAAGGTCTTGTTAACATCTTTGTCTGCTTTGTTGTTACCATTTTACACGGCACATACACATGGCGC

Figure 7A (cont.)

TTTTTTAACACACCTGTGAGTTCTGTCACTTATGTGGTAGCTTTGCTGACTGCGGCATATAACTATTTTT
ACGCTAGTGACATTCTTAGTTGTGCTATGACACTATTTGCTAGTGTGACTGGCAACTGGTTCGTTGGTGC
TGTTTGTTATAAAGCTGCTGTTTATATGGCCTTGAGATTTCCTACTTTTGTGGCTATTTTTGGTGATATT
AAGAGTGTTATGTTCTGTTACCTTGTGTTGGGTTATTTTACCTGTTGCTTCTACGGTATTCTCTACTGGT
TCAACAGGTTTTTTAAGGTTAGTGTAGGTGTCTATGACTATACTGTTAGTGCTGCTGAGTTTAAGTATAT
GGTTGCTAACGGCCTACGTGCACCAACTGGAACACTTGATTCACTACTTCTGTCTGCCAAATTGATTGGT
ATTGGTGGTGAGCGGAATATTAAGATTTCTTCCGTTCAGTCTAAACTGACTGATATTAAGTGTAGTAACG
TTGTGCTTTTAGGCTGTCTCTCTAGCATGAATGTCTCAGCAAATTCAACAGAATGGGCCTATTGTGTTGA
CTTGCATAACAAGATCAACTTGTGTAATGACCCAGAAAAAGCGCAGGAAATGCTACTTGCTTTGTTGGCA
TTTTTCCTTAGTAAGAATAGTGCTTTTGGTTTAGATGACTTATTGGAATCCTATTTTAATGACAATAGTA
TGTTGCAGAGTGTTGCATCTACTTATGTCGGTTTGCCTTCTTATGTCATTTATGAAAATGCACGCCAACA
GTATGAAGATGCTGTTAATAATGGTTCTCCACCTCAGTTGGTTAAGCAATTGCGCCATGCCATGAATGTA
GCAAAGAGCGAATTTGACCGTGAGGCTTCTACTCAGCGTAAGCTTGATAGAATGGCGGAACAGGCTGCAG
CACAGATGTACAAAGAGGCACGAGCAGTTAATAGGAAGTCCAAAGTTGTAAGTGCTATGCATTCACTGCT
TTTTGGTATGTTGAGACGTTTGGACATGTCTTCTGTAGACACCATTCTCAACTTGGCAAAGGATGGGGTT
GTACCTCTGTCTGTCATACCGGCAGTCAGTGCTACTAAGCTTAACATTGTTACTTCTGATATCGATTCTT
ATAATCGTATCCAGCGTGAGGGATGTGTCCACTACGCTGGTACCATTTGGAATATAATTGATATCAAGGA
CAATGATGGCAAGGTGGTACACGTTAAGGAGGTAACCGCACAGAATGCTGAGTCCCTGTCATGGCCCCTG
GTCCTTGGGTGTGAGCGTATTGTCAAGCTCCAGAATAATGAAATTATTCCCGGTAAGCTGAAGCAGCGCT
CCATTAAGGCAGAAGGAGATGGCATAGTTGGAGAAGGTAAGGCACTTTACAATAATGAGGGTGGACGTAC
TTTTATGTATGCTTTCATCTCGGACAAACCGGACCTGCGTGTAGTCAAGTGGGAGTTCGATGGTGGTTGT
AACACTATTGAGCTAGAACCACCACGTAAGTTCTTGGTGGATTCTCCTAATGGTGCACAGATCAAGTATC
TCTACTTTGTTCGTAACCTTAACACGTTACGTAGGGGTGCTGTTCTCGGCTACATAGGTGCCACTGTACG
CTTGCAGGCTGGTAAACAAACAGAACAGGCTATTAACTCTTCATTGTTGACACTTTGCGCTTTCGCTGTG
GATCCTGCTAAGACCTACATCGATGCTGTCAAAAGTGGTCACAAACCAGTAGGTAACTGTGTTAAGATGT
TGGCCAATGGTTCTGGTAATGGACAAGCTGTTACTAATGGTGTGGAGGCTAGTACTAACCAGGATTCATA
CGGTGGTGCGTCCGTGTGTCTATATTGTAGAGCACATGTTGAGCATCCATCTATGGATGGTTTTTGCAGA
CTGAAAGGCAAGTACGTACAGGTTCCACTAGGTACAGTGGATCCTATACGTTTTGTACTTGAGAATGACG
TTTGCAAGGTTTGTGGTTGTTGGCTGGCTAATGGCTGCACTTGTGACAGATCCATTATGCAAAGCACTGA
TATGGCTTATTTAAACGAGTACGGGGCTCTAGTGCAGCTCGACTAGAGCCCTGTAACGGTACTGATACAC
AACATGTGTATCGTGCTTTTGACATCTACAACAAGGATGTTGCTTGTCTAGGTAAATTCCTCAAGGTGAA
CTGTGTTCGCCTGAAGAATTTGGATAAGCATGATGCATTCTATGTTGTCAAAAGATGTACCAAGTCTGCG
ATGGAACACGAGCAATCCATCTATAGCAGACTTGAAAAGTGTGGAGCCGTAGCCGAACACGATTTCTTCA
CTTGGAAGGATGGTCGTGCCATCTATGGTAACGTTTGTAGAAAGGATCTTACCGAGTATACTATGATGGA
TTTGTGTTACGCTTTACGTAACTTTGATGAAAACAATTGCGATGTTCTTAAGAGCATTTTAATTAAGGTA
GGCGCTTGTGAGGAGTCCTACTTCAATAATAAAGTCTGGTTTGACCCTGTTGAAAATGAAGACATTCATC
GTGTCTATGCATTGTTAGGTACCATTGTTTCACGTGCTATGCTTAAATGCGTTAAGTTCTGTGATGCAAT
GGTTGAACAAGGTATAGTTGGTGTTGTCACATTAGATAATCAGGATCTTAATGGTGATTTTTATGATTTT
GGTGATTTTACTTGTAGCATCAAGGGAATGGGTATACCCATTTGCACATCATATTACTCTTATATGATGC
CTGTTATGGGTATGACTAATTGCCTTGCTAGTGAGTGTTTTGTTAAGAGTGATATATTTGGTGAGGATTT
CAAGTCATATGACCTGCTGGAATATGATTTCACGGAGCATAAGACAGCACTCTTCAACAAGTATTTCAAG
TATTGGGGACTGCAATACCACCCTAATTGTGTGGACTGCAGTGATGAGCAGTGCATAGTTCACTGTGCCA
ACTTCAATACGTTGTTTTCCACTACTATACCTATTACGGCATTTGGACCTTTGTGTCGCAAGTGTTGGAT
TGATGGTGTTCCACTGGTAATTACAGCTGGTTATCATTTTAAACAGTTAGGTATAGTTTGGAACAATGAC
CTCAACTTACACTCTAGCAGGCTCTCTATTAACGAATTACTCCAGTTTTGTAGTGATCCTGCATTGCTTA
TAGCATCATCACCAGCCCTTGTTGATCAGCGTACTGTTTGCTTTTCAGTTGCAGCGCTAGGTACAGGTAT
GACTAACCAGACTGTTAAACCTGGCCATTTCAATAAGGAGTTTTATGACTTCTTACTTGAGCAAGGTTTC
TTTTCTGAGGGCTCTGAGCTTACTTTAAAGCACTTCTTCTTTGCACAGAAGGGTGATGCAGCTGTTAAGG
ATTTTGACTACTATAGGTATAATAGACCTACTGTTCTGGACATTTGCCAAGCTCGCGTCGTGTATCAAAT
AGTGCAACGCTATTTTGATATTTACGAAGGTGGTTGTATCACTGCTAAAGAGGTGGTTGTTACAAACCTT
AACAAGAGCGCAGGTTATCCTTTGAACAAGTTTGGTAAAGCTGGTCTTTACTATGAGTCTTTATCCTATG
AGGAACAGGATGAACTTTATGCTTATACTAAGCGTAACATCCTGCCCACTATGACACAGCTCAACCTTAA

Figure 7A (cont.)

ATATGCTATAAGTGGCAAAGAACGTGCACGCACAGTGGGTGGTGTTTCGCTTTTGTCAACCATGACTACT
CGGCAGTATCATCAGAAACACCTTAAGTCCATAGTTAATACTAGGGGCGCTTCGGTTGTTATTGGTACTA
CTAAGTTTTATGGTGGTTGGGACAATATGCTTAAGAACCTTATTGATGGTGTTGAAAATCCGTGTCTTAT
GGGTTGGGACTACCCAAAGTGCGACAGAGCACTGCCCAATATGATACGTATGATTTCAGCCATGATTTTA
GGCTCTAAGCACACCACATGCTGCAGTTCCACTGACCGCTTTTTCAGGTTGTGCAATGAATTGGCTCAAG
TCCTTACTGAGGTTGTTTATTCTAATGGAGGTTTTTATTTGAAGCCAGGTGGTACTACCTCTGGTGATGC
AACCACCGCATATGCAAACTCAGTTTTTAATATCTTCCAAGCAGTAAGTGCCAATGTTAACAAACTTCTT
AGTGTTGACAGCAATGTCTGTCATAATTTAGAAGTTAAGCAATTGCAGCGTAAGCTTTATGAGTGCTGTT
ATAGATCAACTACCGTCGATGACCAGTTCGTCGTTGAGTATTATGGTTACTTGCGTAAACATTTTTCAAT
GATGATTCTTTCTGATGATGGCGTTGTTTGTTATAACAATGACTATGCATCACTTGGTTATGTCGCTGAT
CTTAACGCCTTCAAGGCTGTTTTGTATTACCAGAACAATGTCTTCATGAGCGCCTCTAAATGTTGGATCG
AGCCTGACATTAATAAAGGTCCTCATGAATTTTGCTCGCAGCATACTATGCAGATTGTCGATAAAGATGG
TACTTATTACCTTCCTTACCCTGATCCTTCAAGAATTCTCTCTGCAGGTGTGTTTGTTGATGACGTTGTT
AAAACTGATGCAGTTGTATTGCTTGAACGTTATGTGTCATTGGCTATAGATGCCTACCCGTTATCTAAGC
ATGAAAACCCTGAATATAAGAAGGTGTTTTATGTGCTTTTGGATTGGGTTAAGCATCTGTACAAAACTCT
TAATGCTGGTGTGTTAGAGTCTTTTTCTGTCACACTTTTGGAAGATTCTACTGCTAAATTCTGGGATGAG
AGCTTTTATGCCAACATGTATGAGAAATCTGCAGTTTTACAATCTGCAGGGCTTTGTGTTGTTTGTGGCT
CTCAAACTGTTTTACGTTGTGGTGATTGTCTACGGCGTCCTATGCTTTGTACTAAGTGTGCTTATGATCA
TGTCATTGGAACAACTCACAAGTTCATTTTGGCCATCACTCCATATGTGTGTTGTGCTTCAGATTGTGGT
GTCAATGATGTAACTAAGCTCTACTTAGGTGGTCTTAGTTATTGGTGTCATGACCACAAGCCACGTCTTG
CATTCCCGTTGTGCTCTGCTGGTAATGTTTTTGGCTTGTACAAAAATTCTGCTACCGGCTCACCCGATGT
TGAAGACTTTAATCGCATTGCTACATCCGATTGGACTGATGTTTCTGACTACAGGTTGGCAAATGATGTC
AAGGACTCATTGCGTCTGTTTGCAGCGGAAACTATCAAGGCCAAGGAGGAGAGCGTTAAGTCATCCTATG
CTTGTGCAACACTACATGAGGTTGTAGGACCTAAAGAGTTGTTGCTCAAATGGGAAGTCGGCAGACCCAA
ACCACCCCTTAATAGAAATTCGGTTTTCACTTGTTATCATATAACGAAGAACACCAAATTTCAAATCGGT
GAGTTTGTGTTTGAGAAGGCAGAATATGATAATGATGCTGTAACATATAAAACTACCGCCACAACAAAAC
TTGTTCCTGGCATGGTTTTTGTGCTTACCTCACATAATGTTCAGCCATTGCGCGCACCGACCATTGCTAA
TCAAGAACGTTATTCCACTATACATAAGTTGCATCCTGCTTTTAACATACCTGAAGCTTATTCTAGCTTA
GTGCCCTATTACCAATTGATTGGTAAGCAGAAGATTACAACTATTCAGGGACCTCCCGGTAGTGGTAAAT
CTCACTGTGTTATAGGGCTAGGTTTGTACTATCCAGGTGCACGTATAGTGTTTACAGCTTGTTCTCATGC
AGCGGTCGATTCACTTTGTGTGAAAGCTTCCACTGCTTATAGCAATGACAAATGTTCACGCATCATACCA
CAGCGCGCTCGTGTTGAGTGTTATGATGGTTTCAAGTCTAATAATACTAGTGCTCAGTACCTTTTCTCTA
CTGTCAATGCTTTGCCAGAGTGCAATGCGGACATTGTTGTGGTGGATGAGGTCTCTATGTGCACTAATTA
TGACTTGTCTGTCATAAATCAGCGCATCAGCTATAGGCATGTAGTCTATGTTGGTGACCCTCAACAGCTG
CCTGCACCACGTGTTATGATTTCACGTGGTACTTTGGAACCAAAGGACTACAACGTTGTCACTCAACGCA
TGTGTGCCCTTAAGCCTGATGTTTTCTTGCACAAGTGTTATCGCTGTCCTGCTGAGATAGTGCGTACTGT
GTCTGAGATGGTCTATGAAAACCAATTCATTCCTGTGCACCCAGATAGCAAGCAGTGTTTTAAAATCTTT
TGCAAGGGTAATGTTCAGGTTGATAATGGTTCAAGCATTAATCGCAGGCAATTGGATGTTGTGCGTATGT
TTTTGGCTAAAAATCCTAGGTGGTCAAAGGCTGTTTTTATTTCTCCTTATAACAGCCAGAATTATGTTGC
CAGCCGCATGCTAGGTCTACAAATTCAGACAGTTGACTCATCCCAGGGTAGTGAGTATGACTATGTCATT
TACACACAAACTTCAGATACTGCCCATGCCTGTAATGTTAACAGGTTTAATGTTGCCATCACAAGGGCCA
AGAAAGGCATATTATGTATAATGTGCGATAGGTCCCTTTTTGATGTGCTTAAATTCTTTGAGCTTAAATT
GTCTGATTTGCAGGCTAATGAGGGTTGTGGTCTTTTTAAAGACTGTAGCAGAGGTGATGATCTGTTGCCA
CCATCTCACGCTAACACCTTCATGTCTTTAGCGGACAATTTTAAGACTGATCAAGATCTTGCTGTTCAAA
TAGGTGTTAATGGACCCATTAAATATGAGCATGTTATCTCGTTTATGGGTTTCCGTTTTGATATCAACAT
ACCCAACCATCATACTCTCTTTTGCACACGCGACTTTGCCATGCGCAATGTTAGAGGTTGGTTAGGCTTT
GACGTTGAAGGAGCACATGTTGTTGGCTCTAACGTCGGTACAAATGTCCCATTGCAATTAGGGTTTTCTA
ACGGTGTTGATTTTGTTGTCAGACCTGAAGGTTGCGTTGTAACAGAGTCTGGTGACTACATTAAACCCGT
CAGAGCTCGTGCTCCACCAGGGGAACAATTCGCACACCTTTTGCCTTTACTTAAACGCGGCCAACCATGG
GATGTTGTCCGCAAACGTATAGTGCAGATGTGTAGTGACTACCTGGCCAACCTATCAGACATACTAATTT
TTGTGTTGTGGGCTGGTGGTTTGGAGTTGACAACTATGCGTTATTTTGTCAAGATTGGACCAAGTAAGAG
TTGTGATTGTGGTAAGGTTGCTACTTGTTACAATAGTGCGCTGCATACGTACTGTTGTTTCAAACATGCC

Figure 7A (cont.)

CTTGGTTGTGATTATCTGTATAACCCATACTGTATTGATATACAGCAGTGGGGATACAAGGGATCACTTA
GCCTTAACCACCATGAGCATTGTAATGTACATAGAAACGAGCATGTGGCTTCTGGTGATGCCATAATGAC
TCGCTGTCTGGCCATACATGATTGCTTTGTCAAGAACGTTGACTGGTCCATCACATACCCATTTATTGGT
AATGAGGCTGTTATTAATAAGAGCGGCCGAATTGTGCAATCACACACTATGCGGTCAGTTCTTAAGTTAT
ACAATCCGAAAGCCATATATGATATTGGCAATCCTAAGGGCATTAGATGTGCCGTAACGGATGCTAAGTG
GTTTTGCTTTGACAAGAATCCTACTAATTCTAATGTCAAGACATTGGAGTATGACTATATAACACATGGC
CAATTTGATGGGTTGTGCTTGTTTTGGAATTGCAATGTAGACATGTATCCAGAATTTTCTGTGGTCTGTC
GTTTTGATACTCGCTGTAGGTCACCACTCAACTTGGAGGGTTGTAATGGTGGTTCACTGTATGTTAATAA
TCATGCATTCCATACACCGGCTTTTGACAAGCGTGCTTTTGCTAAGTTGAAGCCAATGCCATTTTTCTTT
TATGATGATACTGAGTGTGACAAGTTACAGGACTCCATAAACTATGTTCCTCTTAGGGCTAGTAACTGCA
TTACTAAATGTAATGTTGGTGGTGCTGTCTGTAGTAAGCATTGTGCTATGTATCATAGCTATGTTAATGC
TTACAACACTTTTACGTCGGCGGGCTTTACTATTTGGGTGCCTACTTCGTTTGACACCTATAATCTGTGG
CAGACATTTAGTAACAATTTGCAAGGTCTTGAGAACATTGCTTTCAATGTCGTAAAGAAAGGATCTTTTG
TTGGTGCCGAAGGTGAACTTCCTGTAGCTGTGGTTAATGACAAAGTGCTCGTTAGAGATGGTACTGTTGA
TACTCTTGTTTTTACAAACAAGACATCACTACCCACTAACGTAGCTTTTGAGTTGTATGCCAAGCGTAAG
GTAGGACTCACCCCACCCATTACGATCCTACGTAACTTGGGTGTAGTTTGTACATCTAAGTGTGTCATTT
GGGACTATGAAGCCGAACGTCCACTTACTACTTTTACAAAGGATGTTTGTAAATATACCGACTTTGAGGG
TGACGTCTGTACACTCTTTGATAACAGCATTGTTGGTTCATTAGAGCGATTCTCCATGACCCAAAATGCT
GTGCTTATGTCACTTACAGCTGTTAAAAAGCTTACTGGCATAAAGTTAACTTATGGTTATCTTAATGGTG
TCCCAGTTAACACACATGAAGATAAACCTTTTACTTGGTATATTTACACTAGGAAGAACGGCAAGTTCGA
GGACCATCCTGATGGCTATTTTACCCAAGGTAGAACAACCGCTGATTTTAGCCCTCGTAGCGACATGGAA
AAGGACTTCCTAAGTATGGATATGGGTCTGTTTATTAACAAGTACGGACTTGAGGATTACGGCTTTGAGC
ACGTTGTGTATGGTGATGTTTCAAAAACCACCCTTGGTGGTTTGCATCTACTAATTTCGCAGGTGCGTCT
GGCCTGTATGGGTGTGCTCAAAATAGACGAGTTTGTGTCTAGTAATGATAGCACGTTAAAGTCTTGTACT
GTTACATATGCTGATAACCCTAGTAGTAAGATGGTTTGTACGTATATGGATCTCCTGCTTGACGATTTTG
TCAGCATTCTTAAATCTTTGGATTTGGGCGTTGTATCTAAAGTTCATGAAGTTATGGTCGATTGTAAAAT
GTGGAGGTGGATGTTGTGGTGTAAGGATCATAAACTCCAGACATTTTATCCGCAACTTCAGGCCAGTGAA
TGGAAGTGTGGTTATTCCATGCCTTCTATTTACAAGATACAACGTATGTGTTTAGAACCTTGCAATCTCT
ACAACTATGGTGCTGGTATTAAGTTACCTGATGGCATTATGTTTAACGTAGTTAAATACACACAGCTTTG
TCAATATCTCAATAGCACCACAATGTGTGTACCCCATCACATGCGTGTGCTACATCTTGGTGCTGGCTCC
GACAAGGGTGTTGCACCTGGCACGGCTGTCTTACGACGTTGGTTGCCACTGGATGCCATTATAGTTGACA
ATGATAGTGTGGATTACGTTAGCGATGCTGATTATAGTGTTACAGGAGATTGCTCTACCTTATACCTGTC
AGATAAGTTTGATTTAGTTATATCTGATATGTATGATGGTAAGATTAAAAGTTGTGATGGGGAGAACGTG
TCTAAAGAAGGCTTCTTTCCCTATATTAATGGTGTCATCACCGAAAAGTTGGCACTTGGTGGTACTGTAG
CTATTAAGGTGACGGAGTTTAGTTGGAATAAGAAGTTGTATGAACTCATTCAGAGGTTTGAGTATTGGAC
AATGTTCTGTACCAGTGTTAACACGTCATCGTCAGAGGCATTCTTAATTGGTGTTCACTATTTAGGTGAT
TTTGCAAGTGGCGCTGTGATTGACGGCAACACTATGCATGCCAATTATATCTTCTGGCGTAATTCCACAA
TTATGACTATGTCTTACAATAGTGTACTTGATTTAAGCAAGTTCAATTGTAAGCATAAGGCTACAGTTGT
CATTAATTTAAAAGATTCATCCATTAGTGATGTTGTGTTAGGTTTGTTGAAGAATGGTAAGTTGCTAGTG
CGTAATAATGACGCCATTTGTGGTTTTTCTAATCATTTGGTCAACGTAAACAAATGAAGTCTTTAACCTA
CTTCTGGTTGTTCTTACCAGTACTTTCAACACTTAGCCTACCACAAGATGTCACCAGGTGCTCAGCTAAC
ACTAATTTTAGGCGGTTCTTTTCAAAATTTAATGTTCAGGCGCCTGCAGTTGTTGTACTGGGCGGTTATC
TACCTATTGGTGAAAACCAGGGTGTCAATTCAACTTGGTACTGTGCTGGCCAACATCCAACTGCTAGTGG
CGTTCATGGTATCTTTGTTAGCCATATTAGAGGTGGTCATGGCTTTGAGATTGGCATTTCGCAAGAGCCT
TTTGACCCTAGTGGTTACCAGCTTTATTTACATAAGGCTACTAACGGTAACACTAATGCTACTGCGCGAC
TGCGCATTTGCCAGTTTCCTAGCATTAAAACATTGGGCCCCACTGCTAATAATGATGTTACAACAGGTCG
TAATTGCCTATTTAACAAAGCCATCCCAGCTCATATGAGTGAACATAGTGTTGTCGGCATAACATGGGAT
AATGATCGTGTCACTGTCTTTTCTGACAAGATCTATTATTTTTATTTTAAAAATGATTGGTCCCGTGTTG
CGACAAAGTGTTACAACAGTGGAGGTTGTGCTATGCAATATGTTTACGAACCCACCTATTACATGCTTAA
TGTTACTAGTGCTGGTGAGGATGGTATTTCTTATCAACCCTGTACAGCTAATTGCATTGGTTATGCTGCC
AATGTATTTGCTACTGAGCCCAATGGCCACATACCAGAAGGTTTTAGTTTTAATAATTGGTTTCTTTTGT
CCAATGATTCCACTTTGGTGCATGGTAAGGTGGTTTCCAACCAACCATTGTTGGTCAATTGTCTTTTGGC

Figure 7A (cont.)

CATTCCTAAGATTTATGGACTAGGCCAATTTTTCTCCTTTAATCAAACGATCGATGGTGTTTGTAATGGA
GCTGCTGTGCAGCGTGCCCCAGAGGCTCTGAGGTTTAATATTAATGACATCTCTGTCATTCTTGCTGAAG
GCTCAATTGTACTTCATACTGCTTTAGGAACAAATTTTTCTTTTGTTTGCAGTAATTCCTCAAATCCTCA
CTTAGCCACCTTCGCCATACCTCTGGGTGCTACCCAAGTACCTTATTATTGTTTTTTTAAAGTGGATACT
TACAACTCCACTGTTTATAAATTTTTGGCTGTTTTACCTCCTACCGTCAGGGAAATTGTCATCACCAAGT
ATGGTGATGTTTATGTCAATGGGTTTGGATACTTGCATCTCGGTTTGTTGGATGCTGTCACAATTAATTT
CACTGGTCATGGCACTGACGATGATGTTTCTGGTTTTTGGACCATAGCATCGACTAATTTTGTTGATGCA
CTCATCGAAGTTCAAGGAACCGCCATTCAGCGTATTCTTTATTGTGATGGGCATCCTGTTAGCCAACTCA
AGTGTTCTCAGGTTGCTTTTGACCTTGACGATGGTTTTTACACTATTTCTTCTAGAAACCTTCTGAGTCA
TGAACAGCCAATTTCTTTTGTTACTCTGCCATCATTTAATGATCATTCTTTTGTTAACATTACTGTATCT
GCTTCCTTTGGTGGTCATAGTGGTGCCAACCTTATTGCATCTGACACTACTATCAATGGGTTTAGTTCTT
TCTGTGTTGACACTAGACAATTTACCATTTCACTGTTTTATAACGTTACAAACAGTTATGGTTATGTGTC
TAAATCACAGGACAGTAATTGCCCTTTCACCTTGCAATCTGTTAATGATTACCTGTCTTTTAGCAAATTT
TGTGTTTCCACCAGCCTTTTGGCTAGTGCCTGTACCATAGATCTTTTTGGTTACCCTGAGTTTGGTAGTG
GTGTTAAGTTTACGTCCCTTTACTTTCAATTCACAAAGGGTGAGTTGATTACTGGCACGCCTAAACCACT
TGAAGGTGTCACGGACGTTTCTTTTATGACTCTGGATGTGTGTACCAAGTATACTATCTATGGCTTTAAA
GGTGAGGGTATCATTACCCTTACAAATTCTAGCTTTTTGGCAGGTGTTTATTACACATCTGATTCTGGAC
AGTTGTTAGCCTTTAAGAATGTCACTAGTGGTGCTGTTTATTCTGTTACGCCATGTTCTTTTTCAGAGCA
GGCTGCATATGTTGATGATGATATAGTGGGTGTTATTTCTAGTTTGTCTAGCTCCACTTTTAACAGTACT
AGGGAGTTGCCTGGTTTCTTCTACCATTCTAATGATGGCTCTAATTGTACAGAGCCTGTGTTGGTGTATA
GTAACATAGGTGTTTGTAAATCTGGCAGTATTGGCTACGTCCCATCTCAGTCTGGCCAAGTCAAGATTGC
ACCCACGGTTACTGGGAATATTAGTATTCCCACCAACTTTAGTATGAGTATTAGGACAGAATATTTACAG
CTTTACAACACGCCTGTTAGTGTTGATTGTGCCACATATGTTTGTAATGGTAACTCTCGTTGTAAACAAT
TACTCACCCAGTACACTGCAGCATGTAAGACCATAGAGTCAGCATTACAACTCAGCGCTAGGCTTGAGTC
TGTTGAAGTTAACTCTATGCTTACTATTTCTGATGAGGCTCTACAGTTAGCTACCATTAGTTCGTTTAAT
GGTGATGGATATAATTTTACTAATGTGCTGGGTGTTTCTGTGTATGATCCTGCAAGTGGCAGGGTGGTAA
AGAAGAGGTCTTTTATTGAAGACCTGCTTTTTAATAAAGTGGTTACTAATGGCCTTGGTACTGTTGATGA
AGACTATAAGCGCTGTTCTAATGGTCGCTCTGTGGCAGATCTAGTCTGTGCACAGTATTACTCTGGTGTC
ATGGTACTACCTGGTGTTGTTGACGCTGAGAAGCTTCACATGTATAGTGCGTCTCTCATCGGTGGTATGG
TGCTAGGAGGTTTTACTTCTGCAGCGGCATTGCCTTTTAGCTATGCTGTTCAAGCTAGACTCAATTATCT
TGCTCTACAGACGGATGTTCTACAGCGGAACCAGCAATTGCTTGCTGAGTCTTTTAACTCTGCTATTGGT
AATATAACTTCAGCCTTTGAGAGTGTTAAAGAGGCTATTAGTCAAACTTCCAAGGGTTTGAACACTGTGG
CTCATGCGCTTACTAAGGTTCAAGAGGTTGTTAACTCGCAGGGTGCAGCTTTGACTCAACTTACCGTACA
GCTGCAACACAACTTCCAAGCCATTTCTAGTTCTATTGATGACATTTACTCTCGACTGGACATTCTTTCA
GCCGATGCTCAGGTTGACCGTCTCATCACCGGCAGATTATCAGCACTTAATGCTTTTGTTGCTCAAACCC
TCACTAAGTATACTGAGGTTCAGGCTAGCAGGAAGTTAGCACAGCAAAAGGTTAATGAGTGCGTTAAATC
GCAATCTCAGCGTTATGGTTTTTGTGGTGGTGATGGCGAGCACATTTTCTCTCTGGTACAGGCAGCACCT
CAGGGCCTGCTGTTTTTACATACAGTACTTGTACCGAGTGATTTTGTAGATGTTATTGCCATCGCTGGCT
TATGCGTTAACGATGAAATTGCCTTGACTCTACGTGAGCCTGGCTTAGTCTTGTTTACGCATGAACTTCA
AAATCATACTGCGACGGAATATTTTGTTTCATCGCGACGTATGTTTGAACCTAGAAAACCTACCGTTAGT
GATTTTGTTCAAATTGAGAGTTGTGTGGTCACCTATGTCAATTTGACTAGAGACCAACTACCAGATGTAA
TCCCAGATTACATCGATGTTAACAAAACACTTTATGAGATTTTAGCTTCTCTGCCCAATAGAACTGGTCC
AAGTCTTCCTTTAGATGTTTTTAATGCCACTTATCTTAATCTCACTGGTGAAATTGCAGATTTAGAGCAG
CGTTCAGAGTCTCTCCGTAATACTACAGAGGAGCTCCAAAGTCTTATATATAATATCAACAACACACTAG
TTGACCTTGAGTGGCTCAACCGAGTTGAGACATATATCAAGTGGCCGTGGTGGGTTTGGTTGATTATTTT
CATTGTTCTCATCTTTGTTGTGTCATTACTAGTGTTCTGCTGCATTTCCACGGGTTGTTGTGGATGCTGC
GGCTGCTGCTGTGCTTGTTTCTCAGGTTGTTGTAGGGGTCCTAGACTTCAACCTTACGAAGTTTTTGAAA
AGGTCCACGTGCAGTGATGTTTCTTGGACTTTTTCAATACACGATTGACACAGTTGTCAAAGATGTCTCA
AAGTCTGCTAACTTGTCTTTGGATGCTGTCCAAGAGTTGGAGCTCAATGTAGTTCCAATTAGACAAGCTT
CAAATGTGACGGGTTTTCTTTTCACCAGTGTTTTTATCTACTTCTTTGCACTGTTTAAAGCGTCTTCTTT
GAGGCGCAATTATATTATGTTGGCAGCGCGTTTTGCTGTCATTGTTCTTTATTGCCCACTTTTATATTAT
TGTGGTGCATTTTTAGATGCAACTATTATTTGTTGCACACTTATTGGCAGGCTTTGTTTAGTCTGCTTTT

Figure 7A (cont.)

ACTCCTGGCGCTATAAAAATGCGCTCTTTATTATTTTTAATACTACGACACTTTCTTTCCTCAATGGTAA
AGCAGCTTATTATGACGGCAAATCCATTGTGATTTTAGAAGGTGGTGACCATTACATCACTTTTGGCAAC
TCTTTTGTTGCTTTTGTTAGTAGCATCGACTTGTATCTAGCTATACGTGGGCGGCAAGAAGCTGACCTAC
AGCTGTTGCGAACTGTTGAGCTTCTTGATGGCAAGAAGCTTTATGTCTTTTCGCAACATCAAATTGTTGG
CATTACTAATGCTGCATTTGACTCAATTCAACTAGACGAGTATGCTACAATTAGTGAATGATAATGGTCT
AGTAGTTAATGTTATACTTTGGCTTTTCGTACTCTTTTTCCTGCTTATTATAAGCATTACTTTCGTCCAA
TTGGTTAATCTGTGCTTCACTTGTCACCGGTTGTGTAATAGCGCAGTTTACACACCTATAGGGCGTTTGT
ATAGAGTTTATAAGTCTTACATGCAAATAGACCCCCTCCTTAGTACTGTTATTGACGTATAAACGAAATA
TGTCTAACGGTTCTATTCCCGTTGATGAGGTGATTCAACACCTTAGAAACTGGAATTTCACATGGAATAT
CATACTGACGATACTACTTGTAGTGCTTCAGTATGGCCATTACAAGTACTCTGCGTTCTTGTATGGTGTC
AAGATGGCTATTCTATGGATACTTTGGCCTCTTGTGTTAGCACTGTCACTTTTTGATGCATGGGCTAGCT
TTCAGGTCAATTGGGTCTTTTTTGCTTTCAGCATCCTTATGGCTTGCATCACTCTTATGCTGTGGATAAT
GTACTTTGTCAATAGCATTCGGTTGTGGCGCAGGACACATTCTTGGTGGTCTTTCAATCCTGAAACAGAC
GCGCTTCTCACTACTTCTGTGATGGGCCGACAGGTCTGCATTCCAGTGCTTGGAGCACCAACTGGTGTAA
CGCTAACACTCCTTAGTGGTACATTGCTTGTAGAGGGCTATAAGGTTGCTACTGGCGTACAGGTAAGTCA
ATTACCTAATTTCGTCACAGTCGCCAAGGCCACTACAACAATTGTCTACGGACGTGTTGGTCGTTCAGTC
AATGCTTCATCTGGCACTGGTTGGGCTTTCTATGTCCGGTCCAAACACGGCGACTACTCAGCTGTGAGTA
ATCCGAGTTCGGTTCTCACAGATAGTGAGAAAGTGCTTCATTTAGTCTAAACAGAAACTTTATGGCTTCT
GTCAGTTTTCAGGATCGTGGCCGCAAACGGGTGCCATTATCCCTCTATGCCCCTCTTAGGGTTACTAATG
ACAAACCCCTTTCTAAGGTACTTGCAAATAATGCTGTACCCACTAATAAAGGAAATAAGGACCAGCAAAT
TGGATACTGGAATGAGCAAATTCGCTGGCGCATGCGCCGTGGTGAGCGAATTGAACAACCTTCCAATTGG
CATTTCTACTACCTCGGAACAGGACCTCACGCCGACCTCCGCTATAGGACTCGTACTGAGGGTGTTTTCT
GGGTTGCTAAAGAAGGCGCAAAGACTGAACCCACTAACCTGGGTGTCAGAAAGGCGTCTGAAAAGCCAAT
TATTCCAAATTTCTCTCAACAGCTTCCCAGCGTAGTTGAGATTGTTGAACCTAACACACCTCCTACTTCA
CGTGCAAATTCACGTAGCAGGAGTCGTGGTAATGGCAACAACAGGTCCAGATCTCCAAGTAACAACAGAG
GCAATAACCAGTCCCGCGGTAATTCACAGAATCGTGGAAATAACCAGGGTCGTGGAGCTTCTCAGAACAG
AGGAGGCAATAATAATAACAATAACAAGTCTCGTAACCAGTCCAAGAACAGAAACCAGTCAAATGACCGT
GGTGGTGTAACATCACGCGATGATCTGGTGGCTGCTGTCAAGGATGCCCTTAAATCTTTGGGTATTGGCG
AAAACCCTGACAAGCTTAAGCAACAGCAGAAGCCCAAACAGGAAAGGTCTGACAGCAGCGGCAAAAATAC
ACCTAAGAAGAACAAATCCAGAGCCACTTCGAAAGAACGTGACCTCAAAGACATCCCAGAGTGGAGGAGA
ATTCCCAAGGGCGAAAATAGCGTAGCAGCTTGCTTCGGACCCAGGGGAGGCTTCAAAAATTTTGGAGATG
CGGAATTTGTCGAAAAAGGTGTTGATGCCTCAGGCTATGCTCAGATCGCCAGTTTAGCACCAAATGTTGC
AGCATTGCTCTTTGGTGGTAATGTGGCTGTTCGTGAGCTAGCGGACTCTTACGAGATTACATATAATTAT
AAAATGACTGTGCCAAAGTCTGATCCAAATGTAGAGCTTCTTGTTTCACAGGTGGATGCATTTAAAACTG
GGAATGCAAAACCCCAGAGAAAGAAGGAAAAGAAGAACAAGCGTGAAACCACGCAGCAGCTGAATGAAGA
GGCCATCTACGATGATGTGGGTGTGCCATCTGATGTGACTCATGCCAATTTGGAATGGGACACAGCTGTT
GATGGTGGTGACACGGCCGTTGAAATTATCAACGAGATCTTCGACACAGGAAATTAAACAATGTTTGACT
GGCTTATCCTGGCTATGTCCCAGGGTAGTGCCATTACACTGTTATTACTGAGTGTTTTTCTAGCGACTTG
GCTGCTGGGCTATGGCTTTGCCCTCTAACTAGCGGTCTTGGTCTTGCACACAACGGTAAGCCAGTGGTAA
TGTCAGTGCAAGAAGGATATTACCATAGCACTGTCATGAGGGGAACGCAGTACCTTTTCATCTAAACCTT
TGCACGAGTAATCAAAGATCCGCTTGACGAGCCTATATGGAAGAGCGTGCCAGGTATTTGACTCAAGGAC
TGTTAGTAACTGAAGACCTGACGGTGTTGATATGGATACACAAAAAAAAAAAAAAAAAAAAA

Figure 7B icPEDV-mut4 sequence (SEQ ID NO: 35)

ACTTAAAGAGATTTTCTATCTACGGATAGTTAGCTCTTTTTCTAGACTCTTGTCTACTCAATTCAACTAA
ACGAAATTTTGTCCTTCCGGCCGCATGTCCATGCTGCTGGAAGCTGACGTGGAATTTCATTAGGTTTGCT
TAAGTAGCCATCGCAAGTGCTGTGCTGTCCTCTAGTTCCTGGTTGGCGTTCCGTCGCCTTCTACATACTA
GACAAACAGCCTTCCTCCGGTTCCGTCTGGGGGTTGTGTGGATAACTAGTTCTGTCTAGTTTGAAACCAG
TAACTGTCGGCTATGGCTAGCAACCATGTTACATTGGCTTTTGCCAATGATGCAGAAATTTCAGCTTTTG
GCTTTTGCACTGCTAGTGAAGCCGTCTCATACTATTCTGAGGCCGCCGCTAGTGGATTTATGCAATGCCG
TGCCGTGTCCTTCGATCTCGCTGACACTGTTGAGGGATTGCTTCCCGAAGACTATGTCATGGTGGTGGTC
GGCACTACCAAGCTTAGTGCGTATGTGGACACTTTTGGTAGCCGCCCCAAAAACATTTGTGGTTGGCTGT
TATTTTCTAACTGTAATTACTTCCTCGAAGAGTTAGAGCTTACTTTTGGTCGTCGTGGTGGTAACATCGT
GCCAGTTGACCAATACATGTGTGGCGCTGACGGTAAACCTGTTCTTCAGGAATCCGAATGGGAGTATACA
GATTTCTTTGCTGACTCCGAAGACGGTCAACTCAACATTGCTGGTATCACTTATGTGAAGGCCTGGATTG
TAGAGCGATCGGATGTCTCTTATGCGAGTCAGAATTTAACATCTATTAAGTCTATTACTTACTGTTCAAC
CTATGAGCATACTTTTCCTGATGGTACTGCCATGAAGGTTGCACGTACTCCAAAGATTAAGAAGACTGTT
GTCTTGTCTGAGCCACTTGCTACTATCTACAGGGAAATTGGTTCTCCTTTTGTGGATAATGGGAGCGATG
CTCGTTCTATCATTAAGAGACCAGTGTTCCTCCACGCTTTTGTTAAGTGTAAGTGTGGTAGTTATCATTG
GACTGTTGGTGATTGGACTTCCTATGTCTCCACTTGCTGTGGCTTTAAGTGTAAGCCAGTCCTTGTGGCT
TCATGCTCTGCTACGCCTGGTTCTGTTGTGGTTACGCGCGCTGGTGCTGGCACTGGTGTTAAGTATTACA
ACAACATGTTCCTGCGCCATGTGGCAGACATTGATGGGTTGGCATTCTGGCGAATTCTCAAGGTGCAGTC
CAAAGACGACCTCGCTTGCTCTGGTAAATTCCTTGAACACCATGAGGAAGGTTTCACAGATCCTTGCTAC
TTTTTGAATGACTCGAGCATTGCTACTAAGCTCAAGTTTGACATCCTTAGTGGCAAGTTTTCTGATGAAG
TCAAACAAGCTATCTTTGCTGGTCATGTTGTTGTTGGCAGCGCGCTCGTTGACATTGTTGACGATGCACT
GGGACAGCCTTGGTTTATACGTAAGCTTGGTGACCTTGCAAGTGCAGCTTGGGAGCAGCTTAAGGCTGTC
GTTAGAGGCCTTAACCTCCTGTCTGATGAGGTCGTGCTCTTTGGCAAAAGACTTAGCTGTGCCACTCTTA
GTATCGTTAACGGTGTTTTTGAGTTCATCGCCGAAGTGCCTGAGAAGTTGGCTGCGGCTGTTACAGTTTT
TGTCAACTTCTTGAATGAGCTTTTTGAGTCTGCCTGTGACTGCTTAAAGGTCGGAGGTAAAACCTTTAAC
AAGGTTGGCTCTTATGTTCTTTTTGACAACGCATTGGTTAAGCTTGTCAAGGCAAAAGTTCGCGGCCCAC
GACAGGCAGGTGTTTGTGAAGTTCGTTACACAAGCCTTGTTATTGGGAGTACTACCAAGGTGGTTTCCAA
GCGCGTTGAAAATGCCAATGTGAATCTCGTCGTCGTTGACGAGGATGTGACCCTCAACACCACTGGTCGT
ACAGTTGTTGTTGACGGACTTGCATTCTTCGAGAGTGACGGGTTTTACAGACATCTTGCTGATGCTGACG
TTGTCATTGAACATCCTGTTTATAAGTCTGCTTGTGAGCTCAAGCCAGTTTTTGAGTGTGACCCAATACC
TGATTTTCCTATGCCTGTGGCCGCTAGTGTTGCAGAGCTTTGTGTGCAAACTGATCTGTTGCTTAAAAAT
TACAACACTCCTTATAAAACTTACAGCTGCGTTGTGAGAGGTGATAAGTGTTGTATCACTTGCACCTTAC
ATTTCACAGCACCAAGTTATATGGAGGCTGCTGCTAATTTTGTAGACCTCTGTACCAAGAACATTGGTAC
TGCTGGTTTTCATGAGTTTTACATTACGGCCCATGAACAACAGGATCTGCAAGGGTTCGTAACCACTTGT
TGCACGATGTCAGGTTTTGAGTGTTTTATGCCTATAATCCCACAGTGTCCAGCAGTGCTTGAAGAGATTG
ATGGTGGTAGCATCTGGCGGTCTTTTATCACTGGTCTTAATACAATGTGGGATTTTTGCAAGCATCTTAA
AGTCAGCTTTGGACTAGATGGCATTGTTGTCACTGTAGCACGCAAATTTAAACGACTTGGTGCTCTCTTG
GCAGAAATGTATAACACTTACCTTTCAACTGTGGTGGAAAACTTGGTACTGGCCGGTGTTAGCTTCAAGT
ATTATGCCACCAGTGTCCCAAAAATTGTTTTGGGCTGTTGTTTTCACAGTGTTAAAAGTGTTCTTGCAAG
TGCCTTCCAGATTCCTGTCCAGGCAGGCGTTGAGAAGTTTAAAGTCTTCCTTAACTGTGTTCACCCTGTT
GTACCACGTGTCATTGAAACTTCTTTTGTGGAATTAGAAGAGACGACATTTAAACCACCAGCACTCAATG
GTAGTATTGCTATTGTTGATGGCTTTGCTTTCTATTATGATGGAACACTATACTATCCCACCGATGGTAA
TAGCGTTGTTCCTATCTGCTTTAAGAAGAAAGGTGGTGGTGATGTCAAATTCTCTGATGAAGTCTCTGTT
AAAACCATTGACCCAGTTTATAAGGTCTCCCTTGAATTTGAGTTCGAGTCTGAGACTATTATGGCTGTGC
TTAATAAGGCTGTTGGTAATTGTATCAAGGTTACAGGTGGTTGGGACGATGTTGTTGAGTATATCAATGT
TGCCATTGAGGTTCTTAAAGATCACATCGATGTGCCTAAGTACTACATCTATGATGAGGAAGGTGGCACC
GATCCTAATCTGCCCGTAATGGTTTCTCAGTGGCCGTTGAATGATGACACGATCTCACAGGATCTGCTTG

Figure 7B (cont.)

ATGTTGAAGTTGTTACTGATGCGCCAGTTGATTTCGAGGGTGATGAAGTAGACTCCTCTGACCCTGATAA
GGTGGCAGACGTGGCTAACTCTGAGCCTGAGGATGACGGTCTTAATGTAGCTCCTGAAACAAATGTAGAG
TCTGAAGTTGAGGAAGTTGCCGCAACCTTGTCCTTTATTAAAGATACACCTTCCACAGTTACTAAGGATC
CTTTTGCTTTTGACTTTGCAAGCTATGGAGGACTTAAGGTTTTAAGACAATCTCATAACAACTGCTGGGT
TACTTCTACCTTGGTGCAGCTACAATTGCTTGGCATCGTTGATGACCCTGCAATGGAGCTTTTTAGTGCT
GGTAGAGTTGGTCCAATGGTTCGCAAATGCTATGAGTCACAAAAGGCTATCTTGGGATCTTTGGGTGATG
TGTCGGCTTGCCTAGAGTCTCTGACTAAGGACCTACACACACTTAAGATTACCTGTTCTGTAGTCTGTGG
TTGTGGTACTGGTGAACGTATCTATGATGGTTGTGCTTTTCGTATGACGCCAACTTTGGAACCGTTCCCA
TATGGTGCTTGTGCTCAGTGTGCTCAAGTTTTGATGCACACTTTTAAAAGTATTGTTGGCACCGGCATCT
TTTGTCGAGATACTACTGCTCTCTCCTTGGATTCTTTGGTTGTAAAACCTCTTTGTGCGGCTGCTTTTAT
AGGCAAGGATAGTGGTCATTATGTCACTAACTTTTATGATGCCGCTATGGCTATTGATGGTTATGGTCGT
CATCAGATAAAGTATGACACACTGAACACTATTTGTGTTAAAGACGTTAATTGGACAGCACCTTTTGTCC
CAGACGTTGAGCCTGTATTGGAGCTTGTTGTCAAACCTTTCTATTCTTATAAGAATGTTGATTTTTACCA
AGGAGATTTTAGTGACCTTGTTAAACTTCCATGTGATTTTGTTGTTAATGCTGCAAATGAGAATTTGTCT
CACGGTGGCGGCATAGCAAAGGCCATTGATGTTTATACCAAGGGCATGTTGCAGAAGTGCTCGAATGATT
ACATTAAAGCACACGGTCCCATTAAAGTTGGACGTGGTGTCATGTTGGAGGCATTAGGTCTTAAGGTCTT
TAATGTTGTTGGTCCACGTAAGGGTAAGCATGCACCTGAGCTTCTTGTTAAGGCTTATAAGTCCGTTTTT
GCTAATTCAGGTGTTGCTCTTACACCTTTGATTAGTGTTGGAATTTTTAGTGTTCCTTTGGAAGAATCTT
TATCTGCTTTTCTTGCATGTGTTGGTGATCGCCACTGTAAGTGCTTTTGTTATAGTGACAAAGAGCGCGA
GGCGATCATTAATTACATGGATGGCTTGGTAGATGCTATTTTCAAAGATGCACTTGTTGATACTACTCCT
GTCCAGGAAGATGTTCAACAAGTTTCACAAAAACCAGTTTTGCCTAATTTTGAACCTTTCAGGATTGAAG
GTGCTCATGCTTTCTATGAGTGCAACCCTGAAGGTTTGATGTCATTAGGTGCTGACAAGCTGGTGTTGTT
TACAAATTCCAATTTGGATTTTTGTAGCGTTGGTAAGTGTCTTAACAATGTGACTGGCGGTGCATTGCTT
GAAGCCATAAATGTATTTAAAAAGAGTAACAAAACAGTGCCTGCTGGCAACTGTGTTACTTTTGAGTGTG
CAGATATGATTTCTATTACTATGGTAGTATTGCCATCTGACGGTGATGCTAATTATGACAAAAATTATGC
ACGCGCCGTCGTCAAGGTATCTAAGCTTAAAGGCAAGTTATTGCTTGCTGTTGGTGATGCCATGTTGTAT
TCCAAGTTGTCCCACCTCAGCGTGTTAGGTTTCGTATCCACACCTGATGATGTGGAGCGTTTCTACGCAA
ATAAGAGTGTGGTTATTAAAGTTACTGAGGATACACGTAGTGTTAAGACTGTTAAAGTAGAATCCACTGT
TACTTATGGACAACAAATTGGACCTTGTCTTGTTAATGACACCGTTGTCACAGACAACAAACCTGTTGTT
GCTGATGTTGTAGCTAAGGTTGTACCAAGTGCTAATTGGGATTCACATTATGGTTTTGATAAGGCTGGTG
AGTTCCACATGCTAGACCATACTGGGTTTGCCTTTCCTAGTGAAGTTGTTAACGGTAGGCGTGTGCTTAA
AACCACAGATAATAACTGTTGGGTTAATGTTACATGTTTACAATTACAGTTTGCTAGATTTAGGTTCAAG
TCAGCAGGTCTACAGGCTATGTGGGAGTCCTATTGTACTGGTGATGTTGCTATGTTTGTGCATTGGTTGT
ACTGGCTTACTGGTGTTGACAAAGGTCAGCCTAGTGATTCAGAAAATGCACTTAACATGTTGTCTAAGTA
CATTGTTCCTGCTGGTTCTGTCACTATTGAACGTGTCACGCATGACGGTTGTTGTTGTAGTAAGCGTGTT
GTCACTGCACCAGTTGTGAATGCTAGCGTGTTGAAGCTTGGCGTCGAGGATGGTCTTTGTCCACATGGTC
TTAACTACATTGACAAAGTTGTTGTAGTTAAAGGTACTACAATTGTTGTCAATGTTGGAAAACCTGTAGT
GGCACCATCGCACCTCTTTCTTAAGGGTGTTTCCTACACAACATTCCTAGATAATGGTAACGGTGTTGCC
GGCCATTATACTGTTTTTGATCATGACACTGGTATGGTGCATGATGGAGATGTTTTTGTACCAGGTGATC
TCAATGTGTCTCCTGTTACAAATGTTGTCGTCTCAGAGCAGACGGCTGTTGTGATTAAAGACCCTGTGAA
GAAAGTAGAGTTAGACGCTACAAAGCTGTTAGACACTATGAATTATGCATCGGAAAGATTCTTTTCCTTT
GGTGATTTTATGTCACGTAATTTAATTACAGTGTTTTTGTACATCCTTAGTATTTTGGGTCTCTGTTTTA
GGGCCTTTCGTAAGAGGGATGTTAAAGTTCTAGCTGGTGTACCCCAACGTACTGGTATTATATTGCGTAA
AAGTGTGCGCTATAATGCAAAGGCTTTGGGTGTCTTCTTCAAGCTAAAACTTTATTGGTTCAAAGTTCTT
GGTAAGTTTAGTTTGGGTATTTATGCATTGTATGCATTACTATTCATGACAATACGCTTTACACCTATAG
GTGGCCCTGTTTGTGATGATGTTGTTGCTGGTTATGCTAATTCTAGTTTTGACAAGAATGAGTATTGCAA
CAGTGTTATTTGTAAGGTCTGTCTCTATGGGTACCAGGAACTTTCGGACTTCTCTCACACACAGGTAGTA
TGGCAACACCTTAGAGACCCATTAATTGGTAATGTGATGCCTTTCTTTTATTTGGCATTTCTGGCAATTT
TTGGGGGTGTTTATGTAAAGGCTATTACTCTCTATTTTATTTTCCAGTATCTTAACATACTTGGTGTGTT
TTTGGGCCTACAACAGTCCATTTGGTTTTTGCAGCTTGTGCCTTTTGATGTCTTTGGTGACGAGATCGTC
GTCTTTTTCATCGTTACACGCGTATTGATGTTCCTTAAGCATGTTTTCCTTGGCTGCGATAAGGCATCTT
GTGTGGCTTGCTCTAAGAGTGCTCGCCTTAAGCGCGTTCCTGTCCAGACTATTTTTCAGGGTACTAGCAA

Figure 7B (cont.)

ATCCTTCTACGTACATGCCAATGGTGGTTCTAAGTTCTGTAAGAAGCACAATTTCTTTTGTTTAAATTGT
GATTCTTATGGTCCAGGCTGCACTTTTATTAATGACGTCATTGCAACTGAAGTTGGTAATGTTGTCAAAC
TTAATGTGCAACCGACAGGTCCTGCCACTATTCTTATTGACAAGGTTGAATTCAGTAATGGTTTTTACTA
TCTTTATAGTGGTGACACATTTTGGAAGTACAACTTTGACATAACAGATAACAAATACACTTGCAAAGAG
TCACTTAAAAATTGTAGCATAATCACAGACTTTATTGTTTTTAACAATAATGGTTCCAATGTAAATCAGG
TTAAGAATGCATGTGTGTATTTTTCACAGATGCTTTGTAAACCTGTTAAGTTAGTGGACTCAGCGTTGTT
GGCCAGTTTGTCTGTTGATTTTGGTGCAAGCTTACATAGTGCTTTTGTTAGTGTGTTGTCGAATAGTTTT
GGCAAAGACCTGTCAAGTTGTAATGACATGCAGGATTGCAAGAGCACATTGGGTTTTGATGATGTACCAT
TGGATACCTTTAATGCTGCTGTTGCTGAGGCTCATCGTTACGATGTCCTCTTGACTGACATGTCGTTCAA
CAATTTTACCACCAGTTATGCAAAACCAGAGGAAAAACTTCCCGTCCATGACATTGCCACGTGTATGCGT
GTAGGTGCCAAGATTGTTAATCATAACGTTCTTGTCAAGGATAGTATACCTGTGGTGTGGCTTGTACGTG
ATTTCATTGCCCTTTCTGAAGAAACTAGGAAGTACATTATTCGTACGACTAAAGTTAAGGGTATAACCTT
CATGTTGACCTTTAATGATTGTCGTATGCATACTACCATACCTACTGTTTGCATTGCAAATAAGAAGGGT
GCAGGTCTTCCTAGTTTTTCAAAGGTTAAGAAATTCTTCTGGTTTTTGTGTCTGTTCATAGTTGCTGTTT
TCTTTGCACTAAGCTTTTTTGATTTTAGTACTCAGGTTAGCAGTGATAGTGATTATGACTTCAAGTATAT
TGAGAGTGGCCAGTTGAAGACTTTTGACAATCCACTTAGTTGTGTGCATAATGTCTTTAGTAACTTCGAC
CAGTGGCATGATGCCAAGTTTGGTTTCACCCCCGTCAACAATCCTAGTTGTCCTATAGTCGTTGGTGTAT
CAGACGAAGCGCGCACTGTTCCAGGTATCCCAGCAGGTGTTTATTTAGCTGGTAAAACACTTGTTTTTGC
TATTAACACCATTTTTGGTACATCTGGTTTGTGCTTTGATGCTAGTGGCGTTGCTGATAAGGGCGCTTGC
ATTTTTAATTCGGCTTGCACCACATTATCTGGTTTGGGTGGAACTGCTGTCTACTGTTATAAGAATGGTC
TAGTTGAAGGTGCTAAACTTTATAGTGAGTTGGCACCTCATAGCTACTATAAAATGGTAGATGGTAATGC
TGTGTCTTTACCTGAAATTATCTCACGCGGCTTTGGCATCCGTACTATCCGTACAAAGGCTATGACCTAC
TGTCGCGTTGGCCAGTGTGTGCAATCTGCAGAAGGTGTTTGTTTTGGCGCCGATAGATTCTTTGTCTATA
ATGCAGAATCTGGTTCTGACTTTGTTTGTGGCACAGGGCTCTTTACATTGTTGATGAACGTTATTAGTGT
TTTTTCCAAGACAGTACCAGTAACTGTGTTGTCTGGTCAAATACTTTTTAATTGCATTATTGCTTTTGCT
GCTGTTGCGGTGTGTTTCTTATTTACAAAGTTTAAGCGCATGTTCGGTGATATGTCTGTTGGCGTTTTCA
CTGTCGGTGCTTGTACTTTGTTGAACAATGTTTCCTACATTGTAACACAGAACACACTTGGCATGTTGGG
CTATGCAACTTTGTACTTTTTGTGCACTAAAGGTGTTAGATATATGTGGATTTGGCATTTGGGATTTTTG
ATCTCATATATACTTATTGCACCATGGTGGGTTTTGATGGTTTATGCCTTTTCAGCCATTTTTGAGTTTA
TGCCTAACCTTTTTAAGCTTAAGGTTTCAACACAACTTTTTGAGGGTGACAAGTTCGTAGGCTCTTTTGA
AAATGCTGCAGCAGGTACATTTGTGCTTGATATGCATGCCTATGAGAGACTTGCCAACTCTATCTCAACT
GAAAAACTGCGTCAGTATGCTAGTACTTACAATAAGTACAAGTATTATTCAGGCAGTGCTTCAGAGGCTG
ATTACAGGCTTGCTTGTTTTGCCCATTTGGCCAAGGCTATGATGGATTATGCTTCTAATCACAACGACAC
GTTATACACACCACCCACTGTGAGTTACAATTCAACTCTACAGGCTGGCTTGCGTAAGATGGCACAACCA
TCTGGTGTTGTTGAGAAGTGCATAGTTCGTGTTTGCTATGGTAATATGGCTCTTAATGGCCTATGGCTTG
GTGATACTGTTATCTGCCCACGCCATGTTATAGCGTCTAGTACTACTAGCACTATAGATTATGACTATGC
CCTTTCTGTTTTACGCCTCCACAACTTCTCCATTTCATCTGGTAATGTTTTCCTAGGTGTTGTGGGTGTA
ACCATGCGAGGTGCTTTGTTGCAGATAAAGGTTAATCAAAACAATGTCCACACGCCTAAGTACACCTATC
GCACAGTTAGACCGGGTGAATCTTTTAATATCTTGGCGTGCTATGATGGTTCTGCAGCTGGTGTTTACGG
CGTTAACATGCGCTCTAATTACACTATTAGAGGCTCGTTCATTAATGGCGCTTGTGGTTCACCTGGTTAT
AACATTAACAATGGTACCGTTGAGTTTTGCTATTTACACCAGCTTGAACTTGGTTCAGGCTGTCATGTTG
GTAGCGACTTAGATGGTGTTATGTATGGTGGTTATGAGGACCAACCTACTTTGCAAGTTGAAGGCGCTAG
TAGTCTGTTTACAGAGAATGTGTTGGCATTTCTTTATGCAGCACTCATTAATGGTTCTACCTGGTGGCTT
AGTTCTTCTAGGATTGCTGTAGACAGGTTTAATGAGTGGGCTGTTCATAATGGTATGACAACAGTAGTTA
ATACTGATTGCTTTTCTATTCTTGCTGCTAAGACTGGTGTTGATGTACAACGTTTGTTGGCCTCAATCCA
GTCTCTGCATAAGAATTTTGGTGGAAAGCAAATTCTTGGCTATACCTCGTTGACAGATGAGTTTACTACA
GGTGAAGTTATACGTCAAATGTATGGCGTTAATCTTCAGAGTGGTTATGTTTCACGCGCCTGTAGAAATG
TCTTGCTGGTTGGTTCTTTTCTGACTTTCTTTTGGTCAGAATTAGTTTCCTACACTAAGTTCTTTTGGGT
AAATCCTGGTTATGTCACACCTATGTTTGCGTGTTTGTCATTGCTGTCCTCACTTTTGATGTTCACACTC
AAGCATAAGACATTGTTTTTCCAGGTCTTTCTAATACCTGCTCTGATTGTTACATCTTGCATTAATTTGG
CATTTGATGTTGAAGTCTACAACTATTTGGCAGAGCATTTTGATTACCATGTTTCTCTCATGGGTTTTAA
TGCACAAGGTCTTGTTAACATCTTTGTCTGCTTTGTTGTTACCATTTTACACGGCACATACACATGGCGC

Figure 7B (cont.)

TTTTTTAACACACCTGTGAGTTCTGTCACTTATGTGGTAGCTTTGCTGACTGCGGCATATAACTATTTTT
ACGCTAGTGACATTCTTAGTTGTGCTATGACACTATTTGCTAGTGTGACTGGCAACTGGTTCGTTGGTGC
TGTTTGTTATAAAGCTGCTGTTTATATGGCCTTGAGATTTCCTACTTTTGTGGCTATTTTTGGTGATATT
AAGAGTGTTATGTTCTGTTACCTTGTGTTGGGTTATTTTACCTGTTGCTTCTACGGTATTCTCTACTGGT
TCAACAGGTTTTTTAAGGTTAGTGTAGGTGTCTATGACTATACTGTTAGTGCTGCTGAGTTTAAGTATAT
GGTTGCTAACGGCCTACGTGCACCAACTGGAACACTTGATTCACTACTTCTGTCTGCCAAATTGATTGGT
ATTGGTGGTGAGCGGAATATTAAGATTTCTTCCGTTCAGTCTAAACTGACTGATATTAAGTGTAGTAACG
TTGTGCTTTTAGGCTGTCTCTCTAGCATGAATGTCTCAGCAAATTCAACAGAATGGGCCTATTGTGTTGA
CTTGCATAACAAGATCAACTTGTGTAATGACCCAGAAAAAGCGCAGGAAATGCTACTTGCTTTGTTGGCA
TTTTTCCTTAGTAAGAATAGTGCTTTTGGTTTAGATGACTTATTGGAATCCTATTTTAATGACAATAGTA
TGTTGCAGAGTGTTGCATCTACTTATGTCGGTTTGCCTTCTTATGTCATTTATGAAAATGCACGCCAACA
GTATGAAGATGCTGTTAATAATGGTTCTCCACCTCAGTTGGTTAAGCAATTGCGCCATGCCATGAATGTA
GCAAAGAGCGAATTTGACCGTGAGGCTTCTACTCAGCGTAAGCTTGATAGAATGGCGGAACAGGCTGCAG
CACAGATGTACAAAGAGGCACGAGCAGTTAATAGGAAGTCCAAAGTTGTAAGTGCTATGCATTCACTGCT
TTTTGGTATGTTGAGACGTTTGGACATGTCTTCTGTAGACACCATTCTCAACTTGGCAAAGGATGGGGTT
GTACCTCTGTCTGTCATACCGGCAGTCAGTGCTACTAAGCTTAACATTGTTACTTCTGATATCGATTCTT
ATAATCGTATCCAGCGTGAGGGATGTGTCCACTACGCTGGTACCATTTGGAATATAATTGATATCAAGGA
CAATGATGGCAAGGTGGTACACGTTAAGGAGGTAACCGCACAGAATGCTGAGTCCCTGTCATGGCCCCTG
GTCCTTGGGTGTGAGCGTATTGTCAAGCTCCAGAATAATGAAATTATTCCCGGTAAGCTGAAGCAGCGCT
CCATTAAGGCAGAAGGAGATGGCATAGTTGGAGAAGGTAAGGCACTTTACAATAATGAGGGTGGACGTAC
TTTTATGTATGCTTTCATCTCGGACAAACCGGACCTGCGTGTAGTCAAGTGGGAGTTCGATGGTGGTTGT
AACACTATTGAGCTAGAACCACCACGTAAGTTCTTGGTGGATTCTCCTAATGGTGCACAGATCAAGTATC
TCTACTTTGTTCGTAACCTTAACACGTTACGTAGGGGTGCTGTTCTCGGCTACATAGGTGCCACTGTACG
CTTGCAGGCTGGTAAACAAACAGAACAGGCTATTAACTCTTCATTGTTGACACTTTGCGCTTTCGCTGTG
GATCCTGCTAAGACCTACATCGATGCTGTCAAAAGTGGTCACAAACCAGTAGGTAACTGTGTTAAGATGT
TGGCCAATGGTTCTGGTAATGGACAAGCTGTTACTAATGGTGTGGAGGCTAGTACTAACCAGGATTCATA
CGGTGGTGCGTCCGTGTGTCTATATTGTAGAGCACATGTTGAGCATCCATCTATGGATGGTTTTTGCAGA
CTGAAAGGCAAGTACGTACAGGTTCCACTAGGTACAGTGGATCCTATACGTTTTGTACTTGAGAATGACG
TTTGCAAGGTTTGTGGTTGTTGGCTGGCTAATGGCTGCACTTGTGACAGATCCATTATGCAAAGCACTGA
TATGGCTTATTTAAACGAGTACGGGGCTCTAGTGCAGCTCGACTAGAGCCCTGTAACGGTACTGATACAC
AACATGTGTATCGTGCTTTTGACATCTACAACAAGGATGTTGCTTGTCTAGGTAAATTCCTCAAGGTGAA
CTGTGTTCGCCTGAAGAATTTGGATAAGCATGATGCATTCTATGTTGTCAAAAGATGTACCAAGTCTGCG
ATGGAACACGAGCAATCCATCTATAGCAGACTTGAAAAGTGTGGAGCCGTAGCCGAACACGATTTCTTCA
CTTGGAAGGATGGTCGTGCCATCTATGGTAACGTTTGTAGAAAGGATCTTACCGAGTATACTATGATGGA
TTTGTGTTACGCTTTACGTAACTTTGATGAAAACAATTGCGATGTTCTTAAGAGCATTTTAATTAAGGTA
GGCGCTTGTGAGGAGTCCTACTTCAATAATAAAGTCTGGTTTGACCCTGTTGAAAATGAAGACATTCATC
GTGTCTATGCATTGTTAGGTACCATTGTTTCACGTGCTATGCTTAAATGCGTTAAGTTCTGTGATGCAAT
GGTTGAACAAGGTATAGTTGGTGTTGTCACATTAGATAATCAGGATCTTAATGGTGATTTTTATGATTTT
GGTGATTTTACTTGTAGCATCAAGGGAATGGGTATACCCATTTGCACATCATATTACTCTTATATGATGC
CTGTTATGGGTATGACTAATTGCCTTGCTAGTGAGTGTTTTGTTAAGAGTGATATATTTGGTGAGGATTT
CAAGTCATATGACCTGCTGGAATATGATTTCACGGAGCATAAGACAGCACTCTTCAACAAGTATTTCAAG
TATTGGGGACTGCAATACCACCCTAATTGTGTGGACTGCAGTGATGAGCAGTGCATAGTTCACTGTGCCA
ACTTCAATACGTTGTTTTCCACTACTATACCTATTACGGCATTTGGACCTTTGTGTCGCAAGTGTTGGAT
TGATGGTGTTCCACTGGTAATTACAGCTGGTTATCATTTTAAACAGTTAGGTATAGTTTGGAACAATGAC
CTCAACTTACACTCTAGCAGGCTCTCTATTAACGAATTACTCCAGTTTTGTAGTGATCCTGCATTGCTTA
TAGCATCATCACCAGCCCTTGTTGATCAGCGTACTGTTTGCTTTTCAGTTGCAGCGCTAGGTACAGGTAT
GACTAACCAGACTGTTAAACCTGGCCATTTCAATAAGGAGTTTTATGACTTCTTACTTGAGCAAGGTTTC
TTTTCTGAGGGCTCTGAGCTTACTTTAAAGCACTTCTTCTTTGCACAGAAGGGTGATGCAGCTGTTAAGG
ATTTTGACTACTATAGGTATAATAGACCTACTGTTCTGGACATTTGCCAAGCTCGCGTCGTGTATCAAAT
AGTGCAACGCTATTTTGATATTTACGAAGGTGGTTGTATCACTGCTAAAGAGGTGGTTGTTACAAACCTT
AACAAGAGCGCAGGTTATCCTTTGAACAAGTTTGGTAAAGCTGGTCTTTACTATGAGTCTTTATCCTATG
AGGAACAGGATGAACTTTATGCTTATACTAAGCGTAACATCCTGCCCACTATGACACAGCTCAACCTTAA

Figure 7B (cont.)

ATATGCTATAAGTGGCAAAGAACGTGCACGCACAGTGGGTGGTGTTTCGCTTTTGTCAACCATGACTACT
CGGCAGTATCATCAGAAACACCTTAAGTCCATAGTTAATACTAGGGGCGCTTCGGTTGTTATTGGTACTA
CTAAGTTTTATGGTGGTTGGGACAATATGCTTAAGAACCTTATTGATGGTGTTGAAAATCCGTGTCTTAT
GGGTTGGGACTACCCAAAGTGCGACAGAGCACTGCCCAATATGATACGTATGATTTCAGCCATGATTTTA
GGCTCTAAGCACACCACATGCTGCAGTTCCACTGACCGCTTTTTCAGGTTGTGCAATGAATTGGCTCAAG
TCCTTACTGAGGTTGTTTATTCTAATGGAGGTTTTTATTTGAAGCCAGGTGGTACTACCTCTGGTGATGC
AACCACCGCATATGCAAACTCAGTTTTTAATATCTTCCAAGCAGTAAGTGCCAATGTTAACAAACTTCTT
AGTGTTGACAGCAATGTCTGTCATAATTTAGAAGTTAAGCAATTGCAGCGTAAGCTTTATGAGTGCTGTT
ATAGATCAACTACCGTCGATGACCAGTTCGTCGTTGAGTATTATGGTTACTTGCGTAAACATTTTTCAAT
GATGATTCTTTCTGATGATGGCGTTGTTTGTTATAACAATGACTATGCATCACTTGGTTATGTCGCTGAT
CTTAACGCCTTCAAGGCTGTTTTGTATTACCAGAACAATGTCTTCATGAGCGCCTCTAAATGTTGGATCG
AGCCTGACATTAATAAAGGTCCTCATGAATTTTGCTCGCAGCATACTATGCAGATTGTCGATAAAGATGG
TACTTATTACCTTCCTTACCCTGATCCTTCAAGAATTCTCTCTGCAGGTGTGTTTGTTGATGACGTTGTT
AAAACTGATGCAGTTGTATTGCTTGAACGTTATGTGTCATTGGCTATAGATGCCTACCCGTTATCTAAGC
ATGAAAACCCTGAATATAAGAAGGTGTTTTATGTGCTTTTGGATTGGGTTAAGCATCTGTACAAAACTCT
TAATGCTGGTGTGTTAGAGTCTTTTTCTGTCACACTTTTGGAAGATTCTACTGCTAAATTCTGGGATGAG
AGCTTTTATGCCAACATGTATGAGAAATCTGCAGTTTTACAATCTGCAGGGCTTTGTGTTGTTTGTGGCT
CTCAAACTGTTTTACGTTGTGGTGATTGTCTACGGCGTCCTATGCTTTGTACTAAGTGTGCTTATGATCA
TGTCATTGGAACAACTCACAAGTTCATTTTGGCCATCACTCCATATGTGTGTTGTGCTTCAGATTGTGGT
GTCAATGATGTAACTAAGCTCTACTTAGGTGGTCTTAGTTATTGGTGTCATGACCACAAGCCACGTCTTG
CATTCCCGTTGTGCTCTGCTGGTAATGTTTTTGGCTTGTACAAAAATTCTGCTACCGGCTCACCCGATGT
TGAAGACTTTAATCGCATTGCTACATCCGATTGGACTGATGTTTCTGACTACAGGTTGGCAAATGATGTC
AAGGACTCATTGCGTCTGTTTGCAGCGGAAACTATCAAGGCCAAGGAGGAGAGCGTTAAGTCATCCTATG
CTTGTGCAACACTACATGAGGTTGTAGGACCTAAAGAGTTGTTGCTCAAATGGGAAGTCGGCAGACCCAA
ACCACCCCTTAATAGAAATTCGGTTTTCACTTGTTATCATATAACGAAGAACACCAAATTTCAAATCGGT
GAGTTTGTGTTTGAGAAGGCAGAATATGATAATGATGCTGTAACATATAAAACTACCGCCACAACAAAAC
TTGTTCCTGGCATGGTTTTTGTGCTTACCTCACATAATGTTCAGCCATTGCGCGCACCGACCATTGCTAA
TCAAGAACGTTATTCCACTATACATAAGTTGCATCCTGCTTTTAACATACCTGAAGCTTATTCTAGCTTA
GTGCCCTATTACCAATTGATTGGTAAGCAGAAGATTACAACTATTCAGGGACCTCCCGGTAGTGGTAAAT
CTCACTGTGTTATAGGGCTAGGTTTGTACTATCCAGGTGCACGTATAGTGTTTACAGCTTGTTCTCATGC
AGCGGTCGATTCACTTTGTGTGAAAGCTTCCACTGCTTATAGCAATGACAAATGTTCACGCATCATACCA
CAGCGCGCTCGTGTTGAGTGTTATGATGGTTTCAAGTCTAATAATACTAGTGCTCAGTACCTTTTCTCTA
CTGTCAATGCTTTGCCAGAGTGCAATGCGGACATTGTTGTGGTGGATGAGGTCTCTATGTGCACTAATTA
TGACTTGTCTGTCATAAATCAGCGCATCAGCTATAGGCATGTAGTCTATGTTGGTGACCCTCAACAGCTG
CCTGCACCACGTGTTATGATTTCACGTGGTACTTTGGAACCAAAGGACTACAACGTTGTCACTCAACGCA
TGTGTGCCCTTAAGCCTGATGTTTTCTTGCACAAGTGTTATCGCTGTCCTGCTGAGATAGTGCGTACTGT
GTCTGAGATGGTCTATGAAAACCAATTCATTCCTGTGCACCCAGATAGCAAGCAGTGTTTTAAAATCTTT
TGCAAGGGTAATGTTCAGGTTGATAATGGTTCAAGCATTAATCGCAGGCAATTGGATGTTGTGCGTATGT
TTTTGGCTAAAAATCCTAGGTGGTCAAAGGCTGTTTTTATTTCTCCTTATAACAGCCAGAATTATGTTGC
CAGCCGCATGCTAGGTCTACAAATTCAGACAGTTGACTCATCCCAGGGTAGTGAGTATGACTATGTCATT
TACACACAAACTTCAGATACTGCCCATGCCTGTAATGTTAACAGGTTTAATGTTGCCATCACAAGGGCCA
AGAAAGGCATATTATGTATAATGTGCGATAGGTCCCTTTTTGATGTGCTTAAATTCTTTGAGCTTAAATT
GTCTGATTTGCAGGCTAATGAGGGTTGTGGTCTTTTTAAAGACTGTAGCAGAGGTGATGATCTGTTGCCA
CCATCTCACGCTAACACCTTCATGTCTTTAGCGGACAATTTTAAGACTGATCAAGATCTTGCTGTTCAAA
TAGGTGTTAATGGACCCATTAAATATGAGCATGTTATCTCGTTTATGGGTTTCCGTTTTGATATCAACAT
ACCCAACCATCATACTCTCTTTTGCACACGCGACTTTGCCATGCGCAATGTTAGAGGTTGGTTAGGCTTT
GACGTTGAAGGAGCACATGTTGTTGGCTCTAACGTCGGTACAAATGTCCCATTGCAATTAGGGTTTTCTA
ACGGTGTTGATTTTGTTGTCAGACCTGAAGGTTGCGTTGTAACAGAGTCTGGTGACTACATTAAACCCGT
CAGAGCTCGTGCTCCACCAGGGGAACAATTCGCACACCTTTTGCCTTTACTTAAACGCGGCCAACCATGG
GATGTTGTCCGCAAACGTATAGTGCAGATGTGTAGTGACTACCTGGCCAACCTATCAGACATACTAATTT
TTGTGTTGTGGGCTGGTGGTTTGGAGTTGACAACTATGCGTTATTTTGTCAAGATTGGACCAAGTAAGAG
TTGTGATTGTGGTAAGGTTGCTACTTGTTACAATAGTGCGCTGCATACGTACTGTTGTTTCAAACATGCC

Figure 7B (cont.)

CTTGGTTGTGATTATCTGTATAACCCATACTGTATTGATATACAGCAGTGGGGATACAAGGGATCACTTA
GCCTTAACCACCATGAGCATTGTAATGTACATAGAAACGAGCATGTGGCTTCTGGTGATGCCATAATGAC
TCGCTGTCTGGCCATACATGATTGCTTTGTCAAGAACGTTGACTGGTCCATCACATACCCATTTATTGGT
AATGAGGCTGTTATTAATAAGAGCGGCCGAATTGTGCAATCACACACTATGCGGTCAGTTCTTAAGTTAT
ACAATCCGAAAGCCATATATGATATTGGCAATCCTAAGGGCATTAGATGTGCCGTAACGGATGCTAAGTG
GTTTTGCTTTGACAAGAATCCTACTAATTCTAATGTCAAGACATTGGAGTATGACTATATAACACATGGC
CAATTTGATGGGTTGTGCTTGTTTTGGAATTGCAATGTAGACATGTATCCAGAATTTTCTGTGGTCTGTC
GTTTTGATACTCGCTGTAGGTCACCACTCAACTTGGAGGGTTGTAATGGTGGTTCACTGTATGTTAATAA
TCATGCATTCCATACACCGGCTTTTGACAAGCGTGCTTTTGCTAAGTTGAAGCCAATGCCATTTTTCTTT
TATGATGATACTGAGTGTGACAAGTTACAGGACTCCATAAACTATGTTCCTCTTAGGGCTAGTAACTGCA
TTACTAAATGTAATGTTGGTGGTGCTGTCTGTAGTAAGCATTGTGCTATGTATCATAGCTATGTTAATGC
TTACAACACTTTTACGTCGGCGGGCTTTACTATTTGGGTGCCTACTTCGTTTGACACCTATAATCTGTGG
CAGACATTTAGTAACAATTTGCAAGGTCTTGAGAACATTGCTTTCAATGTCGTAAAGAAAGGATCTTTTG
TTGGTGCCGAAGGTGAACTTCCTGTAGCTGTGGTTAATGACAAAGTGCTCGTTAGAGATGGTACTGTTGA
TACTCTTGTTTTTACAAACAAGACATCACTACCCACTAACGTAGCTTTTGAGTTGTATGCCAAGCGTAAG
GTAGGACTCACCCCACCCATTACGATCCTACGTAACTTGGGTGTAGTTTGTACATCTAAGTGTGTCATTT
GGGACTATGAAGCCGAACGTCCACTTACTACTTTTACAAAGGATGTTTGTAAATATACCGACTTTGAGGG
TGACGTCTGTACACTCTTTGATAACAGCATTGTTGGTTCATTAGAGCGATTCTCCATGACCCAAAATGCT
GTGCTTATGTCACTTACAGCTGTTAAAAAGCTTACTGGCATAAAGTTAACTTATGGTTATCTTAATGGTG
TCCCAGTTAACACACATGAAGATAAACCTTTTACTTGGTATATTTACACTAGGAAGAACGGCAAGTTCGA
GGACCATCCTGATGGCTATTTTACCCAAGGTAGAACAACCGCTGATTTTAGCCCTCGTAGCGACATGGAA
AAGGACTTCCTAAGTATGGATATGGGTCTGTTTATTAACAAGTACGGACTTGAGGATTACGGCTTTGAGG
CCGTTGTGTATGGTGATGTTTCAAAAACCACCCTTGGTGGTTTGGCCCTACTAATTTCGCAGGTGCGTCT
GGCCTGTATGGGTGTGCTCAAAATAGACGAGTTTGTGTCTAGTAATGATAGCACGTTAAAGTCTTGTACT
GTTACATATGCTGATAACCCTAGTAGTAAGATGGTTTGTACGTATATGGATCTCCTGCTTGACGATTTTG
TCAGCATTCTTAAATCTTTGGATTTGGGCGTTGTATCTAAAGTTCATGAAGTTATGGTCGATTGTAAAAT
GTGGAGGTGGATGTTGTGGTGTAAGGATCATAAACTCCAGACATTTTATCCGCAACTTCAGGCCAGTGAA
TGGAAGTGTGGTTATTCCATGCCTTCTATTTACAAGATACAACGTATGTGTTTAGAACCTTGCAATCTCT
ACAACTATGGTGCTGGTATTAAGTTACCTGATGGCATTATGTTTAACGTAGTTAAATACACACAGCTTTG
TCAATATCTCAATAGCACCACAATGTGTGTACCCCATCACATGCGTGTGCTACATCTTGGTGCTGGCTCC
GACAAGGGTGTTGCACCTGGCACGGCTGTCTTACGACGTTGGTTGCCACTGGATGCCATTATAGTTGACA
ATGATAGTGTGGATTACGTTAGCGATGCTGATTATAGTGTTACAGGAGATTGCTCTACCTTATACCTGTC
AGATAAGTTTGATTTAGTTATATCTGCAATGTATGATGGTAAGATTAAAAGTTGTGATGGGGAGAACGTG
TCTAAAGAAGGCTTCTTTCCCTATATTAATGGTGTCATCACCGAAAAGTTGGCACTTGGTGGTACTGTAG
CTATTAAGGTGACGGAGTTTAGTTGGAATAAGAAGTTGTATGAACTCATTCAGAGGTTTGAGTATTGGAC
AATGTTCTGTACCAGTGTTAACACGTCATCGTCAGAGGCATTCTTAATTGGTGTTCACTATTTAGGTGAT
TTTGCAAGTGGCGCTGTGATTGACGGCAACACTATGCATGCCAATTATATCTTCTGGCGTAATTCCACAA
TTATGACTATGTCTTACAATAGTGTACTTGATTTAAGCAAGTTCAATTGTAAGCATAAGGCTACAGTTGT
CATTAATTTAAAAGATTCATCCATTAGTGATGTTGTGTTAGGTTTGTTGAAGAATGGTAAGTTGCTAGTG
CGTAATAATGACGCCATTTGTGGTTTTTCTAATCATTTGGTCAACGTAAACAAATGAAGTCTTTAACCTA
CTTCTGGTTGTTCTTACCAGTACTTTCAACACTTAGCCTACCACAAGATGTCACCAGGTGCTCAGCTAAC
ACTAATTTTAGGCGGTTCTTTTCAAAATTTAATGTTCAGGCGCCTGCAGTTGTTGTACTGGGCGGTTATC
TACCTATTGGTGAAAACCAGGGTGTCAATTCAACTTGGTACTGTGCTGGCCAACATCCAACTGCTAGTGG
CGTTCATGGTATCTTTGTTAGCCATATTAGAGGTGGTCATGGCTTTGAGATTGGCATTTCGCAAGAGCCT
TTTGACCCTAGTGGTTACCAGCTTTATTTACATAAGGCTACTAACGGTAACACTAATGCTACTGCGCGAC
TGCGCATTTGCCAGTTTCCTAGCATTAAAACATTGGGCCCCACTGCTAATAATGATGTTACAACAGGTCG
TAATTGCCTATTTAACAAAGCCATCCCAGCTCATATGAGTGAACATAGTGTTGTCGGCATAACATGGGAT
AATGATCGTGTCACTGTCTTTTCTGACAAGATCTATTATTTTTATTTTAAAAATGATTGGTCCCGTGTTG
CGACAAAGTGTTACAACAGTGGAGGTTGTGCTATGCAATATGTTTACGAACCCACCTATTACATGCTTAA
TGTTACTAGTGCTGGTGAGGATGGTATTTCTTATCAACCCTGTACAGCTAATTGCATTGGTTATGCTGCC
AATGTATTTGCTACTGAGCCCAATGGCCACATACCAGAAGGTTTTAGTTTTAATAATTGGTTTCTTTTGT
CCAATGATTCCACTTTGGTGCATGGTAAGGTGGTTTCCAACCAACCATTGTTGGTCAATTGTCTTTTGGC

Figure 7B (cont.)

CATTCCTAAGATTTATGGACTAGGCCAATTTTTCTCCTTTAATCAAACGATCGATGGTGTTTGTAATGGA
GCTGCTGTGCAGCGTGCCCCAGAGGCTCTGAGGTTTAATATTAATGACATCTCTGTCATTCTTGCTGAAG
GCTCAATTGTACTTCATACTGCTTTAGGAACAAATTTTTCTTTTGTTTGCAGTAATTCCTCAAATCCTCA
CTTAGCCACCTTCGCCATACCTCTGGGTGCTACCCAAGTACCTTATTATTGTTTTTTTAAAGTGGATACT
TACAACTCCACTGTTTATAAATTTTTGGCTGTTTTACCTCCTACCGTCAGGGAAATTGTCATCACCAAGT
ATGGTGATGTTTATGTCAATGGGTTTGGATACTTGCATCTCGGTTTGTTGGATGCTGTCACAATTAATTT
CACTGGTCATGGCACTGACGATGATGTTTCTGGTTTTTGGACCATAGCATCGACTAATTTTGTTGATGCA
CTCATCGAAGTTCAAGGAACCGCCATTCAGCGTATTCTTTATTGTGATGGGCATCCTGTTAGCCAACTCA
AGTGTTCTCAGGTTGCTTTTGACCTTGACGATGGTTTTTACACTATTTCTTCTAGAAACCTTCTGAGTCA
TGAACAGCCAATTTCTTTTGTTACTCTGCCATCATTTAATGATCATTCTTTTGTTAACATTACTGTATCT
GCTTCCTTTGGTGGTCATAGTGGTGCCAACCTTATTGCATCTGACACTACTATCAATGGGTTTAGTTCTT
TCTGTGTTGACACTAGACAATTTACCATTTCACTGTTTTATAACGTTACAAACAGTTATGGTTATGTGTC
TAAATCACAGGACAGTAATTGCCCTTTCACCTTGCAATCTGTTAATGATTACCTGTCTTTTAGCAAATTT
TGTGTTTCCACCAGCCTTTTGGCTAGTGCCTGTACCATAGATCTTTTTGGTTACCCTGAGTTTGGTAGTG
GTGTTAAGTTTACGTCCCTTTACTTTCAATTCACAAAGGGTGAGTTGATTACTGGCACGCCTAAACCACT
TGAAGGTGTCACGGACGTTTCTTTTATGACTCTGGATGTGTGTACCAAGTATACTATCTATGGCTTTAAA
GGTGAGGGTATCATTACCCTTACAAATTCTAGCTTTTTGGCAGGTGTTTATTACACATCTGATTCTGGAC
AGTTGTTAGCCTTTAAGAATGTCACTAGTGGTGCTGTTTATTCTGTTACGCCATGTTCTTTTTCAGAGCA
GGCTGCATATGTTGATGATGATATAGTGGGTGTTATTTCTAGTTTGTCTAGCTCCACTTTTAACAGTACT
AGGGAGTTGCCTGGTTTCTTCTACCATTCTAATGATGGCTCTAATTGTACAGAGCCTGTGTTGGTGTATA
GTAACATAGGTGTTTGTAAATCTGGCAGTATTGGCTACGTCCCATCTCAGTCTGGCCAAGTCAAGATTGC
ACCCACGGTTACTGGGAATATTAGTATTCCCACCAACTTTAGTATGAGTATTAGGACAGAATATTTACAG
CTTTACAACACGCCTGTTAGTGTTGATTGTGCCACATATGTTTGTAATGGTAACTCTCGTTGTAAACAAT
TACTCACCCAGTACACTGCAGCATGTAAGACCATAGAGTCAGCATTACAACTCAGCGCTAGGCTTGAGTC
TGTTGAAGTTAACTCTATGCTTACTATTTCTGATGAGGCTCTACAGTTAGCTACCATTAGTTCGTTTAAT
GGTGATGGATATAATTTTACTAATGTGCTGGGTGTTTCTGTGTATGATCCTGCAAGTGGCAGGGTGGTAA
AGAAGAGGTCTTTTATTGAAGACCTGCTTTTTAATAAAGTGGTTACTAATGGCCTTGGTACTGTTGATGA
AGACTATAAGCGCTGTTCTAATGGTCGCTCTGTGGCAGATCTAGTCTGTGCACAGTATTACTCTGGTGTC
ATGGTACTACCTGGTGTTGTTGACGCTGAGAAGCTTCACATGTATAGTGCGTCTCTCATCGGTGGTATGG
TGCTAGGAGGTTTTACTTCTGCAGCGGCATTGCCTTTTAGCTATGCTGTTCAAGCTAGACTCAATTATCT
TGCTCTACAGACGGATGTTCTACAGCGGAACCAGCAATTGCTTGCTGAGTCTTTTAACTCTGCTATTGGT
AATATAACTTCAGCCTTTGAGAGTGTTAAAGAGGCTATTAGTCAAACTTCCAAGGGTTTGAACACTGTGG
CTCATGCGCTTACTAAGGTTCAAGAGGTTGTTAACTCGCAGGGTGCAGCTTTGACTCAACTTACCGTACA
GCTGCAACACAACTTCCAAGCCATTTCTAGTTCTATTGATGACATTTACTCTCGACTGGACATTCTTTCA
GCCGATGCTCAGGTTGACCGTCTCATCACCGGCAGATTATCAGCACTTAATGCTTTTGTTGCTCAAACCC
TCACTAAGTATACTGAGGTTCAGGCTAGCAGGAAGTTAGCACAGCAAAAGGTTAATGAGTGCGTTAAATC
GCAATCTCAGCGTTATGGTTTTTGTGGTGGTGATGGCGAGCACATTTTCTCTCTGGTACAGGCAGCACCT
CAGGGCCTGCTGTTTTTACATACAGTACTTGTACCGAGTGATTTTGTAGATGTTATTGCCATCGCTGGCT
TATGCGTTAACGATGAAATTGCCTTGACTCTACGTGAGCCTGGCTTAGTCTTGTTTACGCATGAACTTCA
AAATCATACTGCGACGGAATATTTTGTTTCATCGCGACGTATGTTTGAACCTAGAAAACCTACCGTTAGT
GATTTTGTTCAAATTGAGAGTTGTGTGGTCACCTATGTCAATTTGACTAGAGACCAACTACCAGATGTAA
TCCCAGATTACATCGATGTTAACAAAACACTTTATGAGATTTTAGCTTCTCTGCCCAATAGAACTGGTCC
AAGTCTTCCTTTAGATGTTTTTAATGCCACTTATCTTAATCTCACTGGTGAAATTGCAGATTTAGAGCAG
CGTTCAGAGTCTCTCCGTAATACTACAGAGGAGCTCCAAAGTCTTATATATAATATCAACAACACACTAG
TTGACCTTGAGTGGCTCAACCGAGTTGAGACATATATCAAGTGGCCGTGGTGGGTTTGGTTGATTATTTT
CATTGTTCTCATCTTTGTTGTGTCATTACTAGTGTTCTGCTGCATTTCCACGGGTTGTTGTGGATGCTGC
GGCTGCTGCTGTGCTTGTTTCTCAGGTTGTTGTAGGGGTCCTAGACTTCAACCTTACGAAGTTTTTGAAA
AGGTCCACGTGCAGTGATGTTTCTTGGACTTTTTCAATACACGATTGACACAGTTGTCAAAGATGTCTCA
AAGTCTGCTAACTTGTCTTTGGATGCTGTCCAAGAGTTGGAGCTCAATGTAGTTCCAATTAGACAAGCTT
CAAATGTGACGGGTTTTCTTTTCACCAGTGTTTTTATCTACTTCTTTGCACTGTTTAAAGCGTCTTCTTT
GAGGCGCAATTATATTATGTTGGCAGCGCGTTTTGCTGTCATTGTTCTTTATTGCCCACTTTTATATTAT
TGTGGTGCATTTTTAGATGCAACTATTATTTGTTGCACACTTATTGGCAGGCTTTGTTTAGTCTGCTTTT

Figure 7B (cont.)

ACTCCTGGCGCTATAAAAATGCGCTCTTTATTATTTTAATACTACGACACTTTCTTTCCTCAATGGTAA
AGCAGCTTATTATGACGGCAAATCCATTGTGATTTTAGAAGGTGGTGACCATTACATCACTTTTGGCAAC
TCTTTTGTTGCTTTTGTTAGTAGCATCGACTTGTATCTAGCTATACGTGGGCGGCAAGAAGCTGACCTAC
AGCTGTTGCGAACTGTTGAGCTTCTTGATGGCAAGAAGCTTTATGTCTTTTCGCAACATCAAATTGTTGG
CATTACTAATGCTGCATTTGACTCAATTCAACTAGACGAGTATGCTACAATTAGTGAATGATAATGGTCT
AGTAGTTAATGTTATACTTTGGCTTTTCGTACTCTTTTTCCTGCTTATTATAAGCATTACTTTCGTCCAA
TTGGTTAATCTGTGCTTCACTTGTCACCGGTTGTGTAATAGCGCAGTTTACACACCTATAGGGCGTTTGT
ATAGAGTTTATAAGTCTTACATGCAAATAGACCCCCTCCTTAGTACTGTTATTGACGTATAAACGAAATA
TGTCTAACGGTTCTATTCCCGTTGATGAGGTGATTCAACACCTTAGAAACTGGAATTTCACATGGAATAT
CATACTGACGATACTACTTGTAGTGCTTCAGTATGGCCATTACAAGTACTCTGCGTTCTTGTATGGTGTC
AAGATGGCTATTCTATGGATACTTTGGCCTCTTGTGTTAGCACTGTCACTTTTTGATGCATGGGCTAGCT
TTCAGGTCAATTGGGTCTTTTTTGCTTTCAGCATCCTTATGGCTTGCATCACTCTTATGCTGTGGATAAT
GTACTTTGTCAATAGCATTCGGTTGTGGCGCAGGACACATTCTTGGTGGTCTTTCAATCCTGAAACAGAC
GCGCTTCTCACTACTTCTGTGATGGGCCGACAGGTCTGCATTCCAGTGCTTGGAGCACCAACTGGTGTAA
CGCTAACACTCCTTAGTGGTACATTGCTTGTAGAGGGCTATAAGGTTGCTACTGGCGTACAGGTAAGTCA
ATTACCTAATTTCGTCACAGTCGCCAAGGCCACTACAACAATTGTCTACGGACGTGTTGGTCGTTCAGTC
AATGCTTCATCTGGCACTGGTTGGGCTTTCTATGTCCGGTCCAAACACGGCGACTACTCAGCTGTGAGTA
ATCCGAGTTCGGTTCTCACAGATAGTGAGAAAGTGCTTCATTTAGTCTAAACAGAAACTTTATGGCTTCT
GTCAGTTTTCAGGATCGTGGCCGCAAACGGGTGCCATTATCCCTCTATGCCCCTCTTAGGGTTACTAATG
ACAAACCCCTTTCTAAGGTACTTGCAAATAATGCTGTACCCACTAATAAAGGAAATAAGGACCAGCAAAT
TGGATACTGGAATGAGCAAATTCGCTGGCGCATGCGCCGTGGTGAGCGAATTGAACAACCTTCCAATTGG
CATTTCTACTACCTCGGAACAGGACCTCACGCCGACCTCCGCTATAGGACTCGTACTGAGGGTGTTTTCT
GGGTTGCTAAAGAAGGCGCAAAGACTGAACCCACTAACCTGGGTGTCAGAAAGGCGTCTGAAAAGCCAAT
TATTCCAAATTTCTCTCAACAGCTTCCCAGCGTAGTTGAGATTGTTGAACCTAACACACCTCCTACTTCA
CGTGCAAATTCACGTAGCAGGAGTCGTGGTAATGGCAACAACAGGTCCAGATCTCCAAGTAACAACAGAG
GCAATAACCAGTCCCGCGGTAATTCACAGAATCGTGGAAATAACCAGGGTCGTGGAGCTTCTCAGAACAG
AGGAGGCAATAATAATAACAATAACAAGTCTCGTAACCAGTCCAAGAACAGAAACCAGTCAAATGACCGT
GGTGGTGTAACATCACGCGATGATCTGGTGGCTGCTGTCAAGGATGCCCTTAAATCTTTGGGTATTGGCG
AAAACCCTGACAAGCTTAAGCAACAGCAGAAGCCCAAACAGGAAAGGTCTGACAGCAGCGGCAAAAATAC
ACCTAAGAAGAACAAATCCAGAGCCACTTCGAAAGAACGTGACCTCAAAGACATCCCAGAGTGGAGGAGA
ATTCCCAAGGGCGAAAATAGCGTAGCAGCTTGCTTCGGACCCAGGGGAGGCTTCAAAAATTTTGGAGATG
CGGAATTTGTCGAAAAAGGTGTTGATGCCTCAGGCTATGCTCAGATCGCCAGTTTAGCACCAAATGTTGC
AGCATTGCTCTTTGGTGGTAATGTGGCTGTTCGTGAGCTAGCGGACTCTTACGAGATTACATATAATTAT
AAAATGACTGTGCCAAAGTCTGATCCAAATGTAGAGCTTCTTGTTTCACAGGTGGATGCATTTAAAACTG
GGAATGCAAAACCCCAGAGAAAGAAGGAAAAGAAGAACAAGCGTGAAACCACGCAGCAGCTGAATGAAGA
GGCCATCTACGATGATGTGGGTGTGCCATCTGATGTGACTCATGCCAATTTGGAATGGGACACAGCTGTT
GATGGTGGTGACACGGCCGTTGAAATTATCAACGAGATCTTCGACACAGGAAATTAAACAATGTTTGACT
GGCTTATCCTGGCTATGTCCCAGGGTAGTGCCATTACACTGTTATTACTGAGTGTTTTTCTAGCGACTTG
GCTGCTGGGCTATGGCTTTGCCCTCTAACTAGCGGTCTTGGTCTTGCACACAACGGTAAGCCAGTGGTAA
TGTCAGTGCAAGAAGGATATTACCATAGCACTGTCATGAGGGGAACGCAGTACCTTTTCATCTAAACCTT
TGCACGAGTAATCAAAGATCCGCTTGACGAGCCTATATGGAAGAGCGTGCCAGGTATTTGACTCAAGGAC
TGTTAGTAACTGAAGACCTGACGGTGTTGATATGGATACACAAAAAAAAAAAAAAAAAAAAA

CORONAVIRUS VACCINES COMPOSITIONS AND METHOD OF USING SAME

CROSS-REFERENCE TO RELATED APPLICATIONS

This application is a U.S. National Phase of International Patent Application No. PCT/US21/23764 filed Mar. 23, 2021, which claims the benefit of U.S. Provisional Patent Application No. 62/993,489 filed on Mar. 23, 2020. The entire contents of these applications are incorporated herein by reference in their entirety.

STATEMENT REGARDING FEDERALLY SPONSORED RESEARCH

The invention was made with Government support under Grant No. AI085089 awarded by the NIH, and by agreements 58-5030-6-075, 59-5030-8-003, and 58-5030-9-042 by the USDA ARS. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "55120_Seqlisting.txt", which was created on Mar. 19, 2021 and is 96,941 bytes in size. The subject matter of the Sequence Listing is incorporated herein in its entirety by reference.

BACKGROUND

The emergence of severe acute respiratory coronavirus 2 (SARS-CoV-2, the virus that causes COVID-19) in 2019 and the rapid, global spread of infection in humans highlights the need for developing therapeutics and vaccines to limit coronavirus epidemics (Wu F, et al., 2020, Nature 1-8; Zhou P, et al., 2020, Nature 1-4; and Zhu N, et al., 2020, N Engl J Med NEJMoa2001017). Porcine epidemic diarrhea virus (PEDV) emerged suddenly in the United States in 2013, causing immense losses in swineherds and also belongs to the family Coronaviridae in the order Nidovirales. This family of viruses (CoV) all have large, positive-sense RNA genomes (~30 kb) encapsidated by nucleocapsid (N) protein and enveloped by host membranes modified by viral structural proteins designated envelope (E), membrane (M) and spike (S). The spike protein gives the virus the typical crown-like appearance when visualized by electron microscopy (Zhou P, et al., 2020, Nature 1-4). The spike protein engages the host receptor and mediates fusion of the viral and host membrane, allowing entry of the viral genomic RNA into the cytoplasm of the cell. CoV genomic RNA is translated to generate a large polyprotein that is processed into 15 or 16 nonstructural protein (Nsp or nsp) that assemble together to make the viral replication complex. These Nsps were initially proposed to function exclusively in the replication and transcription of viral RNA. However, recent studies revealed that many of these proteins are multifunctional and play important roles in limiting the host response to virus infection by acting as antagonists of the host type I and type III interferon (IFN) responses [reviewed in (Kindler E, and Thiel V., 2014, Curr Opin Microbiol 20:69-75). Type I IFNs (IFN-$\alpha$ and IFN-$\beta$) and type III IFNs (IFN-$\lambda$s) work in autocrine and paracrine fashion to induce an antiviral state by expressing interferon-stimulated genes (ISGs) that limit replication of coronaviruses (Mesev E V, et al., 2019, Nat Microbiol 4:914-924). Studies from Chanapanavar and co-workers document that this virus-mediated delay the host interferon response during infection contributes to more severe disease (Channappanavar R, et al., 2016, Cell Host Microbe 19:181-193; and Channappanavar R, et al., 2019, J Clin Invest 129).

Researchers are developing and testing strategies of inactivating coronavirus interferon antagonists to reduce viral pathogenesis and generate candidate live-attenuated virus vaccines (Deng X, et al., 2017, Proc Natl Acad Sci U.S.A. 114:E4251-E4260; Deng X, et al., 2019, J Virol 93:e02000-18; Menachery V D, et al., 2017, mSphere 2:e00346-17; Menachery V D, et al., 2018, J Virol 92:e00710-18; and Hou Y, et al., 2019, J Virol 93:e00406-19). Menachery and co-workers showed that inactivating the highly conserved CoV 2'-O-methyltransferase (MTase) enzyme in Nsp16, results in virus that activates the host interferon response, is attenuated in animals, and elicits a protective immune response to Middle East respiratory syndrome (MERS) CoV (Menachery V D, et al., 2017, mSphere 2:e00346-17). Hou and co-workers showed that inactivating Nsp16 in combination with a deletion in the spike glycoprotein in the PEDV-22A strain generated a virus that exhibited reduced pathogenesis, but still caused diarrhea in piglets (Hou Y, et al., 2019, J Virol 93:e00406-19).

In 2017, the role of a highly conserved replicase interferon antagonist, the endoribonuclease (EndoU) contained within Nsp15, was evaluated. The rationale for investigating EndoU as a virulence factor stems from promising results obtained using the murine coronavirus, mouse hepatitis virus (MHV). MHV was generated with a mutation in a catalytic histidine residue of EndoU, and it was found that this virus replicated as well as wild type virus in interferon non-responsive cells, revealing that EndoU activity was not required for CoV replication. EndoU-mutant murine coronavirus elicited a robust type I interferon response in interferon responsive macrophages, caused no clinical disease, and elicited a protective immune response in mice (Deng X, et al., 2017, Proc Natl Acad Sci U.S.A. 114:E4251-E4260). These results documented the critical role of EndoU activity in the pathogenesis of the murine coronavirus. To determine if EndoU activity played a role as a virulence factor in other CoVs, studies using PEDV were performed. Inactivating EndoU/Nsp15 in PEDV was found to be sufficient to elicit both type I and type III interferon responses from infected cells, and reduce clinical disease in infect piglets (Deng X, et al., 2019, J Virol 93:e02000-18). However, the inactivation of this single interferon antagonist was not sufficient to fully attenuate PEDV, as the infected piglets still exhibited some diarrhea (Deng X, et al., 2019, J Virol 93:e02000-18). In addition, the PEDV Nsp1 (F44A) mutation was shown to reduce the ability of Nsp1 to antagonize the activation of interferon in an overexpression system in cultured cells (Zhang Q, et al., 2018, J Virol 92:e01677-17; and Zhang Q, Shi K, Yoo D, 2016, Virology 489:252-268), but the effect of this mutation in the context of virus replication was unknown.

Currently, it is unclear if inactivating multiple CoV antagonists in the context of an enteric infection would impact on disease and the host immune response to infection.

SUMMARY OF THE INVENTION

In various aspects, the present disclosure provides coronaviruses, compositions, including vaccine compositions, methods of preparing and using said compositions, and kits. In one embodiment, a vaccine composition is provided comprising a coronavirus comprising at least one mutation in at least two nonstructural proteins, wherein said vaccine composition is capable of inducing an immune response in a subject. In another embodiment, the coronavirus comprises at least one mutation in each of three nonstructural proteins. In another embodiment, the coronavirus comprises at least one mutation in a first nonstructural protein, at least one mutation in a second nonstructural protein, and at least two mutations in a third nonstructural protein.

In still another embodiment, an aforementioned composition is provided wherein at least two of the nonstructural proteins are interferon antagonists. In one embodiment, the coronavirus comprises at least one mutation in a first nonstructural protein, at least one mutation in a second nonstructural protein, and at least two mutations in a third nonstructural protein, wherein each nonstructural protein is an interferon antagonist. In still another embodiment, the at least two mutations are located in a catalytic site of each of said at least two nonstructural proteins.

In yet another embodiment, the present disclosure provides an aforementioned composition wherein the nonstructural proteins are selected from the group consisting of Nsp1, Nsp15 and Nsp16. In one embodiment, the coronavirus comprises one mutation in Nsp1, two mutations in Nsp15, and one mutation in Nsp16. In still another embodiment, the two mutations in Nsp15 and said one mutation in Nsp16 are located in catalytic sites of Nsp15 and Nsp16. In still another embodiment, the mutation Nsp1 is a phenylalanine to alanine substitution, the Nsp15 mutations are both histidine to alanine substitutions and the Nsp16 mutation is an aspartic acid to alanine substitution.

Various coronaviruses are contemplated herein. In various embodiments, an aforementioned composition is provided wherein the coronavirus is selected from the group consisting of severe acute respiratory syndrome coronavirus-2, (SARS-CoV-2), severe acute respiratory syndrome coronavirus (SARS-CoV), Middle East respiratory syndrome coronavirus (MERS-CoV), human coronavirus 229E (HCoV-229E), human coronavirus 0C43 (HCoV-0C43), human coronavirus HKU1 (HCoV-HKU1), human coronavirus NL63 (HCoV-NL63), feline infectious peritonitis virus (FIPV), canine coronavirus (CCoV), infectious bronchitis virus (IBV), bovine coronavirus (BoCoV), transmissible gastroenteritis virus (TGEV), porcine delta coronavirus (PDCoV), porcine epidemic diarrhea virus (PEDV), porcine respiratory coronavirus (PRCV), swine acute diarrhea syndrome coronavirus (SADS-CoV), and porcine hemagglutinating encephalomyelitis coronavirus (PHE-CoV). In some embodiments, the coronavirus is selected from the group consisting of porcine epidemic diarrhea virus (PEDV), transmissible gastroenteritis virus (TGEV), porcine delta coronavirus (PDCoV), swine acute diarrhea coronavirus (SADS-CoV), and SARS-CoV-2. In one embodiment, the coronavirus is porcine PEDV. In another embodiment, the mutation in Nsp1 is F44A as set out in SEQ ID NO: 4, the Nsp15 mutations are H226A and H241A as set out in SEQ ID NO: 8, and the Nsp16 mutation is D129A as set out in SEQ ID NO: 12.

In some embodiments, an aforementioned composition is provided wherein the coronavirus is live and attenuated. In other embodiment, an aforementioned composition is provided wherein the immune response comprises interferon production, interferon-induced protein with tetratricopeptide repeats 2 (IFIT2 or ISG54) production, and antibody production. In some embodiments, the interferon production comprises type I IFN-β and type III IFN-λ production. In one embodiment, the interferon production is 2-fold above the level produced from wild-type coronavirus infection. In yet another embodiment, the immune response comprises a neutralizing antibody response.

The present disclosure provides, in one embodiment, a vaccine composition comprising a live, attenuated porcine epidemic diarrhea virus (PEDV), wherein said PEDV comprises a F44A substitution mutation in Nsp1 as set out in SEQ ID NO: 4, a H226A and H241A substitution mutations in Nsp15 as set out in SEQ ID NO: 8, and a D129A substitution mutation in Nsp16 as set out in SEQ ID NO: 12; wherein said vaccine composition is capable of inducing type I IFN-β and type III IFN-λ production and a neutralizing antibody response.

The present disclosure also provides methods of treating and/or preventing and/or ameliorating symptoms related to coronavirus infections. In one embodiment, the present disclosure provides a method of treating or preventing a disease associated with a coronavirus comprising administering a composition to a subject, said composition comprising a coronavirus with at least one mutation in at each of least two nonstructural proteins, wherein said vaccine composition is capable of inducing an immune response in a subject. In one embodiment, the coronavirus comprises at least one mutation in each of three nonstructural proteins. In still another embodiment, the coronavirus comprises at least one mutation in a first nonstructural protein, at least one mutation in a second nonstructural protein, and at least two mutations in a third nonstructural protein. In yet another embodiment, at least two of the nonstructural proteins are interferon antagonists. In another embodiment, the coronavirus comprises at least one mutation in a first nonstructural protein, at least one mutation in a second nonstructural protein, and at least two mutations in a third nonstructural protein, wherein each nonstructural protein is an interferon antagonist. In still another embodiment, at least two mutations are located in a catalytic site of each of said at least two nonstructural proteins. In another embodiment, the nonstructural proteins are selected from the group consisting of Nsp1, Nsp15 and Nsp16. In one embodiment, the coronavirus comprises one mutation in Nsp1, two mutations in Nsp15, and one mutation in Nsp16. In one embodiment, the two mutations in Nsp15 and said one mutation in Nsp16 are located in catalytic sites of Nsp15 and Nsp16. In yet another embodiment, the mutation Nsp1 is a phenylalanine to alanine substitution, the Nsp15 mutations are both histidine to alanine substitutions and the Nsp16 mutation is an aspartic acid to alanine substitution.

In some embodiment, the disclosure provides an aforementioned method wherein said coronavirus is selected from the group consisting of severe acute respiratory syndrome coronavirus-2, (SARS-CoV-2), severe acute respiratory syndrome coronavirus (SARS-CoV), Middle East respiratory syndrome coronavirus (MERS-CoV), human coronavirus 229E (HCoV-229E), human coronavirus 0C43 (HCoV-0C43), human coronavirus HKU1 (HCoV-HKU1), human coronavirus NL63 (HCoV-NL63), feline infectious peritonitis virus (FIPV), canine coronavirus (CCoV), infectious bronchitis virus (IBV), bovine coronavirus (BoCoV), transmissible gastroenteritis virus (TGEV), porcine delta coronavirus (PDCoV), porcine epidemic diarrhea virus (PEDV), porcine respiratory coronavirus (PRCV), swine acute diarrhea syndrome coronavirus (SADS-CoV), and porcine hemagglutinating encephalomyelitis coronavirus (PHE-CoV). In some embodiments, the coronavirus is selected from the group consisting of porcine epidemic diarrhea virus (PEDV), transmissible gastroenteritis virus (TGEV), porcine delta coronavirus (PDCoV), and SARS-CoV-2. In one embodiment, the coronavirus is porcine epidemic diarrhea virus (PEDV). In another embodiment, the mutation in Nsp1 is F44A as set out in SEQ ID NO: 4, the Nsp15 mutations are H226A and H241A as set out in SEQ ID NO: 8, and the Nsp16 mutation is D129A as set out in SEQ ID NO: 12.

In still other embodiments, an aforementioned method is provided wherein the coronavirus is live and attenuated. In other embodiments, immune response comprises interferon production, interferon-induced protein with tetratricopeptide repeats 2 (IFIT2 or ISG54) production, and antibody production. In one embodiment, the interferon production comprises type I IFN-β and type III IFN-λ production. In yet another embodiment, the interferon production is 2-fold above the level produced from wild-type coronavirus infection. In still another embodiment, the immune response comprises a neutralizing antibody response.

In other embodiment, an aforementioned method is provided wherein said disease is selected from the group consisting of a respiratory disease, a gastrointestinal disease, and a neurological disease. In one embodiment, the respiratory disease is selected from the group consisting of severe acute respiratory syndrome, acute respiratory distress syndrome, or pneumonia. In still another embodiment, the gastrointestinal disease comprises one or more symptoms selected from the group consisting of diarrhea, dehydration and gastrointestinal distress. In one embodiment, the neurological disease is encephalitis. In another embodiment, the subject is a mammal. In some embodiments, the mammal is a porcine or a human.

The present disclosure provides, in one embodiment, a method of treating or preventing a disease associated with a coronavirus comprising administering a composition to a subject, said composition comprising a live, attenuated porcine epidemic diarrhea virus (PEDV), wherein said PEDV comprises a F44A substitution mutation in Nsp1 as set out in SEQ ID NO: 4, a H226A and H241A substitution mutations in Nsp15 as set out in SEQ ID NO: 8, and a D129A substitution mutation in Nsp16 as set out in SEQ ID NO: 12; wherein said vaccine composition is capable of inducing type I IFN-β and type III IFN-λ production and a neutralizing antibody response.

The present disclosure also provides methods of preparing vaccines. In one embodiment, a method of preparing a coronavirus vaccine composition is provided comprising the steps of: (a) identifying at least one catalytic residue in at least two nonstructural proteins in a coronavirus genome; and (b) mutating said at least one catalytic residue; wherein following said mutating in step (b) the coronavirus is live, attenuated and capable of inducing interferon production and a neutralizing antibody response in a subject. In one embodiment, the coronavirus comprises at least one mutation in each of three nonstructural proteins. In another embodiment, the coronavirus comprises at least one mutation in a first nonstructural protein, at least one mutation in a second nonstructural protein, and at least two mutations in a third nonstructural protein. In some embodiments, at least two of the nonstructural proteins are interferon antagonists. In yet another embodiment, the coronavirus comprises at least one mutation in a first nonstructural protein, at least one mutation in a second nonstructural protein, and at least two mutations in a third nonstructural protein, wherein each nonstructural protein is an interferon antagonist. In still other embodiments, at least two mutations are located in a catalytic site of each of said at least two nonstructural proteins. In other embodiments, the nonstructural proteins are selected from the group consisting of Nsp1, Nsp15 and Nsp16. In yet another embodiment, the coronavirus comprises one mutation in Nsp1, two mutations in Nsp15, and one mutation in Nsp16. In one embodiment, the two mutations in Nsp15 and said one mutation in Nsp16 are located in catalytic sites of Nsp15 and Nsp16. In one embodiment, the mutation Nsp1 is a phenylalanine to alanine substitution, the Nsp15 mutations are both histidine to alanine substitutions and the Nsp16 mutation is an aspartic acid to alanine substitution.

In some embodiments, an aforementioned method is provided wherein said coronavirus is selected from the group consisting of severe acute respiratory syndrome coronavirus-2, (SARS-CoV-2), severe acute respiratory syndrome coronavirus (SARS-CoV), Middle East respiratory syndrome coronavirus (MERS-CoV), human coronavirus 229E (HCoV-229E), human coronavirus 0C43 (HCoV-0C43), human coronavirus HKU1 (HCoV-HKU1), human coronavirus NL63 (HCoV-NL63), feline infectious peritonitis virus (FIPV), canine coronavirus (CCoV), infectious bronchitis virus (IBV), bovine coronavirus (BoCoV), transmissible gastroenteritis virus (TGEV), porcine delta coronavirus (PDCoV), porcine epidemic diarrhea virus (PEDV), porcine respiratory coronavirus (PRCV), swine acute diarrhea syndrome coronavirus (SADS-CoV), and porcine hemagglutinating encephalomyelitis coronavirus (PHE-CoV). In some embodiments, the coronavirus is selected from the group consisting of porcine epidemic diarrhea virus (PEDV), transmissible gastroenteritis virus (TGEV), porcine delta coronavirus (PDCoV), and SARS-CoV-2. In one embodiment, the coronavirus is porcine epidemic diarrhea virus (PEDV). In another embodiment, the mutation in Nsp1 is F44A as set out in SEQ ID NO: 4, the Nsp15 mutations are H226A and H241A as set out in SEQ ID NO: 8, and the Nsp16 mutation is D129A as set out in SEQ ID NO: 12.

In some embodiments, an aforementioned is provided wherein said interferon production comprises type I IFN-β and type III IFN-λ production. In another embodiment, the interferon production is 2-fold above the level produced from wild-type coronavirus infection.

The present disclosure provides, in one embodiment, a method of preparing a live, attenuated porcine epidemic diarrhea virus (PEDV) vaccine composition comprising the steps of: substituting a phenylalanine at position 44 in Nsp1 of SEQ ID NO: 4 with alanine; substituting a histidine at position 226 and a histidine at position 241 of Nsp15 of SEQ ID NO: 8 with alanine; and substituting an aspartic acid at position 129 of Nsp16 of SEQ ID NO: 12 with alanine; wherein said vaccine composition is capable of inducing type I IFN-β and type III IFN-λ production and a neutralizing antibody response in a subject.

Various other methods are also provided by the present disclosure. For example, in one embodiment, a method of inducing an immune response in a subject comprising administering an aforementioned composition is provided. In another embodiment, a method of activating production of interferon in a subject comprising administering an aforementioned composition is provided. In another embodiment, a method of inducing apoptotic cell death in a macrophage in a subject comprising administering an aforementioned composition is provided. In still another embodiment, a method of inducing dsRNA sensors in a subject comprising administering an aforementioned composition is provided. In yet another embodiment, a method of vaccinating a subject comprising administering an aforementioned composition is provided. In another embodiment, the composition is administered by a route selected from the group consisting of oral and intramuscular injection.

In still other embodiments, the present disclosure provides a kit comprising an aforementioned composition and instructions for using same. In one embodiment, the kit comprises at least one vial and at least unit dose of said composition.

As described herein, the present disclosure provides coronaviruses. The coronaviruses provided herein may be modified, e.g., mutated in one or more genes, and used in vaccines and methods as described herein. In one embodiment, the represent disclosure provides a coronavirus comprising a coronavirus comprising at least one mutation in at least two nonstructural proteins, wherein said vaccine composition is capable of inducing an immune response in a subject. In one embodiment, the coronavirus comprises at least one mutation in each of three nonstructural proteins. In another embodiment, the coronavirus comprises at least one mutation in a first nonstructural protein, at least one mutation in a second nonstructural protein, and at least two mutations in a third nonstructural protein. In still another embodiment, at least two of the nonstructural proteins are interferon antagonists. In yet another embodiment, the coronavirus comprises at least one mutation in a first nonstructural protein, at least one mutation in a second nonstructural protein, and at least two mutations in a third nonstructural protein, wherein each nonstructural protein is an interferon antagonist. In still another embodiment, at least two mutations are located in a catalytic site of each of said at least two nonstructural proteins.

In another embodiment, the nonstructural proteins are selected from the group consisting of Nsp1, Nsp15 and Nsp16. In one embodiment of the present disclosure, the coronavirus comprises one mutation in Nsp1, two mutations in Nsp15, and one mutation in Nsp16. In one embodiment, the two mutations in Nsp15 and said one mutation in Nsp16 are located in catalytic sites of Nsp15 and Nsp16. In still another embodiment, the mutation Nsp1 is a phenylalanine to alanine substitution, the Nsp15 mutations are both histidine to alanine substitutions and the Nsp16 mutation is an aspartic acid to alanine substitution.

In various embodiment, the present disclosure provides an aforementioned coronavirus wherein said coronavirus is selected from the group consisting of severe acute respiratory syndrome coronavirus-2, (SARS-CoV-2), severe acute respiratory syndrome coronavirus (SARS-CoV), Middle East respiratory syndrome coronavirus (MERS-CoV), human coronavirus 229E (HCoV-229E), human coronavirus 0C43 (HCoV-0C43), human coronavirus HKU1 (HCoV-HKU1), human coronavirus NL63 (HCoV-NL63), feline infectious peritonitis virus (FIPV), canine coronavirus (CCoV), infectious bronchitis virus (IBV), bovine coronavirus (BoCoV), transmissible gastroenteritis virus (TGEV), porcine delta coronavirus (PDCoV), porcine epidemic diarrhea virus (PEDV), porcine respiratory coronavirus (PRCV), swine acute diarrhea syndrome coronavirus (SADS-CoV), and porcine hemagglutinating encephalomyelitis coronavirus (PHE-CoV). In some embodiments, the coronavirus is selected from the group consisting of porcine epidemic diarrhea virus (PEDV), transmissible gastroenteritis virus (TGEV), porcine delta coronavirus (PDCoV), swine acute diarrhea coronavirus (SADS-CoV), and SARS-CoV-2. In one embodiment, the coronavirus is porcine PEDV. In still another embodiment, the mutation in Nsp1 is F44A as set out in SEQ ID NO: 4, the Nsp15 mutations are H226A and H241A as set out in SEQ ID NO: 8, and the Nsp16 mutation is D129A as set out in SEQ ID NO: 12.

The present disclosure provides, in some embodiments, an aforementioned coronavirus wherein the coronavirus is live and attenuated. In some embodiments, an aforementioned coronavirus is provided wherein said immune response comprises interferon production, interferon-induced protein with tetratricopeptide repeats 2 (IFIT2 or ISG54) production, and antibody production. In one embodiment, the interferon production comprises type I IFN-β and type III IFN-λ production. In still another embodiment, the interferon production is 2-fold above the level produced from wild-type coronavirus infection. In yet another embodiment, the immune response comprises a neutralizing antibody response.

In one embodiment, the present disclosure provides a coronavirus comprising a live, attenuated porcine epidemic diarrhea virus (PEDV), wherein said PEDV comprises a F44A substitution mutation in Nsp1 as set out in SEQ ID NO: 4, a H226A and H241A substitution mutations in Nsp15 as set out in SEQ ID NO: 8, and a D129A substitution mutation in Nsp16 as set out in SEQ ID NO: 12; wherein said vaccine composition is capable of inducing type I IFN-β and type III IFN-λ production and a neutralizing antibody response.

Other aspects and advantages of this invention will be further appreciated from the following detailed description.

BRIEF DESCRIPTION OF THE DRAWINGS

FIG. 1A: Schematic diagram of the genome organization of PEDV, with nonstructural proteins 1, 15 and 16 highlighted in gray. FIG. 1B: The location of nucleotide sequence targeted for mutagenesis, and the resulting change in the amino acid sequence is listed.

FIG. 4A: Experimental Design: A total of 34 piglets from 3 sows were randomly grouped to 3 groups. These piglets were either mock-infected or infected with icPEDV wild-type or icPEDV-4mt virus. Blood samples were drawn prior to infection and also at 21 days after infection. FIG. 4B: Outcomes after PEDV infection. Clinical symptoms were evaluated and scored daily. The score is based on the status of feces and the overall appearance of each animal presented as mean±SD. FIG. 4C: Evaluating shedding of viral RNA. RNA was isolated from rectal swab samples and the RNA was subjected to quantitative PCR to determine the genomic RNA copies/mL of sample. Values are presented mean±SEM and analyzed with unpaired t-tests between the groups at the same time point. *, $p<0.05$. The numbers of animal used in each group are shown in parentheses.

FIG. 5A: histology of uninfected control piglet jejunum. FIG. 5B: histology of icPEDV-WT-infected piglet jejunum. FIG. 5C: histology of icPEDV-mut4-infected piglet jejunum. FIG. 5D: IHC staining of uninfected control piglet jejunum. FIG. 5E: IHC staining of icPEDV-WT infected piglet jejunum. FIG. 5F: IHC staining of icPEDV-mut4-infected piglet jejunum.

FIG. 6A: A fluorescence-linked immunosorbent assay (FLISA) was used to determine the PEDV-specific IgG titer. Briefly, PEDV-infected Vero cells were fixed with ethanol/acetone (1:1) and then incubated with serially diluted porcine sera. The highest dilution of serum that produces positive signal is determined as the FLISA titer. FIG. 6B: Virus neutralizing (VN) antibody titers in sera collected 21 dpi. Each value and mean±SEM are presented. *, $p<0.05$; **, $p<0.01$. Dashed lines represent the limit of detection.

FIG. 7 shows the complete nucleotide sequence of icPEDV-WT (FIG. 7A; SEQ ID NO: 34) and icPEDV-mut4 (mutations underlined) (FIG. 7B; SEQ ID NO: 35).

DETAILED DESCRIPTION OF THE INVENTION

Figure 1:
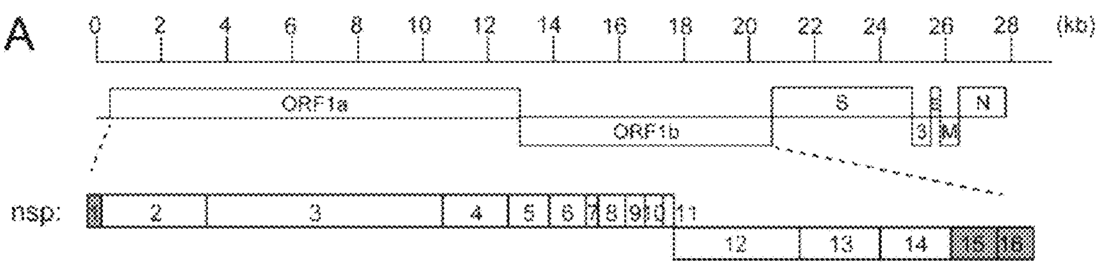
FIG. 1 shows a schematic diagram of the genome organization of PEDV and positions of nucleotide changes made in icPEDV mutant viruses.

Coronaviruses (CoV) have repeatedly emerged from wildlife hosts into humans and livestock animals to cause epidemics with significant morbidity and mortality. CoV outbreaks in swine are associated with enteric infections, which cause diarrhea and fatal disease in young animals. The constellation of viral factors that contribute to developing severe enteric disease is not known. In response to the aforementioned lack of understanding and need in the art for coronavirus vaccines, the present disclosure provides compositions and methods related to CoV interferon antagonists, proteins that block host interferon responses. As described herein, this strategy may be useful for generating candidate live attenuated virus vaccines to existing and emerging coronaviruses.

Coronaviruses and Compositions Comprising Coronaviruses

Coronaviruses (CoVs) are the largest group of viruses belonging to the Nidovirales order, which includes Coronaviridae, Arteriviridae, and Roniviridae families. The Coronavirinae comprise one of two subfamilies in the Coronaviridae family, with the other being the Torovirinae. The Coronavirinae are further subdivided into four groups, the alpha, beta, gamma and delta coronaviruses. The viruses were initially sorted into these groups based on serology but are now divided by phylogenetic clustering.

All viruses in the Nidovirales order are enveloped, non-segmented positive-sense RNA viruses. They all contain very large genomes for RNA viruses, with Coronavirinae having the largest identified RNA genomes, containing approximately 30 kilobase (kb) genomes. Other common features within the Nidovirales order include: i) a highly conserved genomic organization, with a large replicase gene preceding structural and accessory genes; ii) expression of many nonstructural genes by ribosomal frameshifting; iii) several unique or unusual enzymatic activities encoded within the large replicase-transcriptase polyprotein; and iv) expression of downstream genes by synthesis of 3' nested sub-genomic mRNAs. In fact, the Nidovirales order name is derived from these nested 3' mRNAs as nido is Latin for "nest". The major differences within the Nidovirus families are in the number, type, and sizes of the structural proteins. These differences cause significant alterations in the structure and morphology of the nucleocapsids and virions.

Coronaviruses contain a non-segmented, positive-sense RNA genome of ~30 kb. The genome contains a 5' cap structure along with a 3' poly (A) tail, allowing it to act as a mRNA for translation of the replicase polyproteins. The replicase gene encoding the nonstructural proteins (Nsps) occupies two-thirds of the genome, about 20 kb, as opposed to the structural and accessory proteins, which make up only about 10 kb of the viral genome. The 5' end of the genome contains a leader sequence and untranslated region (UTR) that contains multiple stem loop structures required for RNA replication and transcription. Additionally, at the beginning of each structural or accessory gene are transcriptional regulatory sequences (TRSs) that are required for expression of each of these genes (see section on RNA replication). The 3'UTR also contains RNA structures required for replication and synthesis of viral RNA. The organization of the coronavirus genome is 5'-leader-UTR-replicase-S (Spike)-E (Envelope)-M (Membrane)-N (Nucleocapsid)-3'UTR-poly (A) tail with accessory genes interspersed within the structural genes at the 3' end of the genome. The accessory proteins are almost exclusively non-essential for replication in tissue culture; however some have been shown to have important roles in viral pathogenesis.

As used herein, the term "nonstructural protein" or "Nsp" or "nsp" refers to the proteins encoded by coronavirus gene 1 which is translated to produce two long polyprotein (pp), termed pp1a and pp1ab. These two polyproteins are processed by viral proteases into 16 nonstructural proteins, designated Nsp1-16. Every coronavirus has 16 nonstructural proteins, Nsp1-Nsp16 (Netland and Perlman, Nature Reviews Microbiology, 2016).

As used herein, the term "PEDV" refers to the Colorado strain of PEDV. Those of skill in the art recognize that PEDV Colorado strain is representative of many similar strains that infect swine (Wang et al., 2019 Current Opinion in Virology 34: 39-49), with 659 complete genome sequences currently listed in Genbank. Examples of the PEDV genomes that are similar to PEDV Colorado strain include but are not limited to: PEDV/USA/2014/IOWA (GenBank Number: MF373643); PEDV isolates from Italy: 1842/2016, (GenBank Number: KY111278); PEDV strain CV777 (GenBank: NC_003436), each of which are contemplated herein. The Genbank accession ID of the sequence of the complete genome of the PEDV Colorado strain is KF272920.

The coronaviruses and compositions described herein can induce, in various embodiments, multiple immune responses. Immune responses, as used herein, include, but are not limited to, antibodies that neutralize the infectivity of CoVs, antibodies that bind to the CoV particles, a response that protects the vaccinee from subsequent infection by a CoV, and virus-specific T cell responses such as CD8+ and CD4+ CoV-specific responses.

The coronaviruses and compositions described herein comprise proteins that, in various embodiments, include one or more mutations. For example, a nonstructural protein according to the present disclosure may include 1, 2, 3, 4, 5, 6, 7, 8, 9 10 or more mutations. Moreover, the compositions described herein may optionally include a coronavirus with one or more mutations in one or more nonstructural proteins. For example, the coronavirus may include one or more mutations in 1, 2, 3, 4 or 5 no-structural proteins.

In certain embodiments of the present disclosure, the nonstructural proteins are interferon antagonists. "Interferon antagonists" as used herein means viral proteins that function to prevent the host cell from either sensing or transmitting signals to activate the transcription or function of host factors that mount an antiviral response to an invading pathogen. Similarly, in various embodiments the present disclosure provides vaccine compositions that promote the production of interferon production (e.g., by eliminating or reducing the activity of one or more interferon antagonists). Production of interferon, relative to a WT virus, can range from 2-fold or more than the amount induced by the WT virus, and the response can be elicited 2-4 hours earlier after infection as compared to the WT virus infection.

The antibody response plays a key role in protection against viral infections. While antiviral antibodies may reduce the viral burden via several mechanisms, the ability to directly inhibit (neutralize) infection of cells has been extensively studied. Eliciting a neutralizing-antibody response is a goal of many vaccine development programs and commonly correlates with protection from disease. Antibody-mediated neutralization of viruses is the direct inhibition of viral infectivity resulting from antibody docking to virus particles. The elicitation of a neutralizing-antibody (NAb) response is a correlate of protection for many vaccines and contributes to long-lived protection against many viral infections. As used herein, a "neutralizing antibody response" means, in one embodiment, an antibody response sufficient to neutralize the infectivity of 100 TCID50 of the CoV.

One or more of the mutations described herein can occur in a catalytic site of the nonstructural protein or proteins. "Catalytic site," as used herein, refers to amino acid residues required for performing the activity (e.g., the enzymatic activity, in one embodiment) of the protein. By way of example, the following amino acid residues make up catalytic sites of the respective protein. The mutations are also shown below in the context of the nucleotide and amino acid sequences for the respective proteins. The amino acid positions represent positions of the Colorado strain available at accession ID no. KF272920.

- Nsp 15 of PEDV—H226 and H241 (Deng X, et al., 2019, J Virol 93:e02000-18)
- Nsp 16 of PEDV—K45, D129, K169, E202 (Hou Y, et al., 2019, J Virol 93:e00406-19)
- Nsp 1 of PEDV—the catalytic site is unknown, but residue F44 has been documented to be required for Nsp1 to function as an interferon antagonist (Zhang Q, et al., 2018, J Virol 92:e01677-17)

Other coronavirus proteins that have been shown to act as interferon antagonists include but are not limited to Nsp3 (Volk et al., 2020 J. Virology), NS2 (Zhao et al., 2012 Cell Host & Microbe 11: 607-616); structural proteins membrane (M), envelope (E) and nucleocapsid (N) proteins, and strain-specific accessory proteins encoded by open reading frames (ORFs): 3a, 4a, 4b, 6, 7a, 7b, and 8 (reviewed in Sin-Yee Fung, et al., 2020, Emerging Microbes & Infections, 9:1, 558-570). The aforementioned proteins are specifically contemplated herein, including their use alone or in combination with other CoV proteins in vaccines and methods provided herein. In one embodiment, Nsp3 is mutated as described herein and included in a vaccine composition described herein.

It will be appreciated by those of skill in the art that there is a high degree of sequence conservation and homology among coronaviruses (Snijyder et al., 2003 Journal of Molecular Biology 331: 991-1004; Perlman and Netland 2009 Nat Rev Microbiology 7: 439-450). Although specific proteins and amino acids are identified in the context of, for example, PEDV in one embodiment herein, one of skill in the art will readily appreciate that, provided the high degree of conservation, other CoVs and CoV strains may similarly be mutated to practice the methods described herein.

As one example, two histidine residues in a catalytic site of Nsp15, H226 and H241, and the aspartic acid in a catalytic site of Nsp16, D129, are 100% conserved—these residues are in all coronaviruses albeit at different amino acid positions (shown in Deng, X., and Baker, S., 2018, Virology, 517:157-163). By way of example, the catalytic histidine residues of SARS-CoV-2 are histidine 234 and histidine 249. Substituting the catalytic histidine residue of murine CoV (His262) to alanine inactivates interferon antagonism activity (Deng X, et al., 2017, Proc Natl Acad Sci USA 114:E4251-E4260), and substitution of the catalytic histidine residue of PEDV Nsp15 (His226) to alanine inactivated the interferon antagonism activity (Deng X, et al., 2019, J Virol 93:e02000-18). Thus, although the specific number of the amino acid for the catalytic histidine residue may change from one CoV to another, the function is 100% conserved, so those experienced in the art will recognize that substitution of the conserved catalytic residue will inactivate the function of the enzyme in any existing or emerging CoV Nsp15, Nsp16 and/or Nsp1.

"Mutations" as described herein include changes or modifications at the DNA or RNA level or amino acid level. In one embodiment, the mutation (or mutations) is a "substitution" mutation which is a mutation that exchanges one base for another (i.e., A to a G). Such a substitution could: change a codon to one that encodes a different amino acid and cause a small change in the protein produced; change a codon to one that encodes the same amino acid and causes no change in the protein produced (silent mutations); or change an amino-acid-coding codon to a single "stop" codon and cause an incomplete protein. As described herein, in one embodiment the substitution mutations result in the replacement of a WT amino acid with alanine. Other mutations are also contemplated by the present disclosure. Insertions are mutations in which extra base pairs are inserted into a new place in the DNA. Deletions are mutations in which a section of DNA is lost, or deleted.

As described herein, the coronaviruses and vaccine compositions and methods contemplated may be used in association with any coronavirus, including coronaviruses that have not yet emerged. Non-limiting examples of coronaviruses include SARS-Related coronaviruses, severe acute respiratory syndrome coronavirus-2, (SARS-CoV-2), severe acute respiratory syndrome coronavirus (SARS-CoV), Middle East respiratory syndrome coronavirus (MERS-CoV), human coronavirus 229E (HCoV-229E), human coronavirus 0C43 (HCoV-0C43), human coronavirus HKU1 (HCoV-HKU1), human coronavirus NL63 (HCoV-NL63), feline infectious peritonitis virus (FIPV), canine coronavirus (CCoV), infectious bronchitis virus (IBV), bovine coronavirus (BoCoV), transmissible gastroenteritis virus (TGEV), porcine delta coronavirus (PDCoV), porcine epidemic diarrhea virus (PEDV), porcine respiratory coronavirus (PRCV), swine acute diarrhea syndrome coronavirus (SADS-CoV) and porcine hemagglutinating encephalomyelitis coronavirus (PHE-CoV).

Also contemplated herein are CoVs that infect swine using, e.g., as an entry receptor, a swine ACE-2 receptor or swine APN receptor or an unknown receptor (Wang et al., 2019, Opin. Virol., 34:39-49). ACE-2 is a type I transmembrane metallocarboxypeptidase with homology to ACE, an enzyme long-known to be a key player in the Renin-Angiotensin system (RAS) and a target for the treatment of hypertension. In other embodiments, CoVs that infect swine using, e.g., as an entry receptor, amino peptidase N (APN) and/or sialic acid receptor are contemplated.

As provided herein, the Genbank accession ID of PEDV Colorado strain is KF272920. Nsp1, 15 and 16 share this ID as they are from the same virus strain. The following sequences are used herein:

PEDV Nsp1 nucleotide (WT)

(SEQ ID NO: 1)

293 ATGGCTAGCAACCATGTTACATTGGCTTTTGCCAATGATGCAGAAATTTC 342

343 AGCTTTTGGCTTTTGCACTGCTAGTGAAGCCGTCTCATACTATTCTGAGG 392

393 CCGCCGCTAGTGGATTTATGCAATGCCGTTTCGTGTCCTTCGATCTCGCT 442

443 GACACTGTTGAGGGATTGCTTCCCGAAGACTATGTCATGGTGGTGGTCGG 492

493 CACTACCAAGCTTAGTGCGTATGTGGACACTTTTGGTAGCCGCCCCAAAA 542

543 ACATTTGTGGTTGGCTGTTATTTTCTAACTGTAATTACTTCCTCGAAGAG 592

593 TTAGAGCTTACTTTTGGTCGTCGTGGTGGT 622

PEDV Nsp1 nucleotide (F4A mutant)

(SEQ ID NO: 2)

293 ATGGCTAGCAACCATGTTACATTGGCTTTTGCCAATGATGCAGAAATTTC 342

343 AGCTTTTGGCTTTTGCACTGCTAGTGAAGCCGTCTCATACTATTCTGAGG 392

393 CCGCCGCTAGTGGATTTATGCAATGCCGTGCCGTGTCCTTCGATCTCGCT 442

443 GACACTCTTGAGGGATTGCTTCCCGAAGACTATGTCATGGTGGTGCTCGG 492

493 CACTACCAAGCTTAGTGCGTATGTGGACACTTTTGGTAGCCGCCCCAAAA 542

543 ACATTTGTGGTTGGCTGTTATTTTCTAACTGTAATTACTTCCTCGAAGAG 592

593 TTAGAGCTTACTTTTGGTCGTCGTGGTGGT 622

PEDV Nsp1 amino acid (WT)

(SEQ ID NO: 3)

1 MASNHVTLAFANDAEISAFGFCTASEAVSYYSEAAASGFMQCRFVSFDLA 50

51 DTVEGLLPEDYVMVVVGTTKLSAYVDTFGSRPKNICGWLLFSNCNYFLEE 100

101 LELTFGRRGG 110

PEDV Nsp1 amino acid (F4A mutant)

(SEQ ID NO: 4)

1 MASNHVTLAFANDAEISAFGFCTASEAVSYYSEAAASGPMQCRAVSFDLA 50

51 DTVEGLLPEDYVMVVVGTTKLSAYVDTFGSRPKNICGWLLFSNCNYFLEE 100

101 LELTFGRRGG 110

PEDV Nsp15 nucleotide (WT)

(SEQ ID NO: 5)

18715 GGTCTTGAGAACATTGCTTTCAATGTCGTAAAGAAAGGATCTTTTGTTGG 18764

18765 TGCCGAAGGTGAACTTCCTGTAGCTGTGGTTAATGACAAAGTGCTCGTTA 18814

18815 GACATGGTACTGTTGATACTCTTCTTTTTACAAACAAGACATCACTACCC 18864

18865 ACTAACGTAGCTTTTGAGTTGTATGCCAAGCGTAAGGTAGGACTCACCCC 18914

18915 ACCCATTACGATCCTACGTAACTTGGGTGTAGTTTGTACATCTAAGTGTG 18964

18965 TCATTTGGGACTATGAAGCCGAACGTCCACTTACTACTTTTACAAAGGAT 19014

19015 GTTTGTAAATATACCGACTTTGAGGGTGACGTCTGTACACTCTTTGATAA 19064

19065 CAGCATTGTTGGTTCATTAGAGCGATTCTCCATGACCCAAAATGCTGTGC 19114

-continued

19115 TTATGTCACTTACAGCTGTTAAAAAGCTTACTGGCATAAAGTTAACTTAT 19164

19165 GGTTATCTTAATGGTGTCCCAGTTAACACACATGAAGATAAACCTTTTAC 19214

19215 TTGGTATATTTACACTAGGAAGAACGGCAAGTTCGAGGACCATCCTGATG 19264

19265 GCTATTTTACCCAAGGTAGAACAACCGCTGATTTTAGCCCTCGTAGCGAC 19314

19315 ATGGAAAAGGACTTCCTAAGTATGGATATGGGTCTGTTTATTAACAAGTA 19364

19365 CGGACTTGAGGATTACGGCTTTGAGCACGTTGTGTATGGTGATGTTTCAA 19414

19415 AAACCACCCTTGGTGGTTTGCATCTACTAATTTCGCAGGTGCGTCTGGCC 19464

19465 TGTATGGGTGTGCTCAAAATAGACGAGTTTGTGTCTAGTAATGATAGCAC 19514

19515 GTTAAAGTCTTGTACTGTTACATATGCTGATAACCCTAGTAGTAAGATGG 19564

19565 TTTGTACGTATATGGATCTCCTGCTTGACGATTTTGTCAGCATTCTTAAA 19614

19615 TCTTTGGATTTGGGCGTTGTATCTAAAGTTCATGAAGTTATGGTCGATTG 19664

19665 TAAAATGTGGAGGTGGATGTTGTGGTGTAAGGATCATAAACTCCAGACAT 19714

19715 TTTATCCGCAACTTCAG 19731

PEDV Nsp15 nucleotide (H226, H241 mutant)

(SEQ ID NO: 6)

18715 GGTCTTGAGAACATTGCTTTCAATGTCCTAAAGAAAGGATCTTTTGTTGG 18764

18765 TGCCGAAGGTGAACTTCCTGTAGCTGTGGTTAATGACAAAGTGCTCGTTA 18814

18815 GAGATGGTACTGTTGATACTCTTGTTTTTACAAACAAGACATCACTACCC 18864

18865 ACTAACGTAGCTTTTGAGTTGTATGCCAAGCGTAAGGTAGGACTCACCCC 18914

18915 ACCCATTACGATCCTACGTAACTTGGGTGTAGTTTGTACATCTAAGTGTG 18964

18965 TCATTTGGGACTATGAAGCCGAACGTCCACTTACTACTTTTACAAAGGAT 19014

19015 GTTTGTAAATATACCGACTTTGAGGGTGACGTCTGTACACTCTTTGATAA 19064

19065 CAGCATTCTTGGTTCATTAGAGCGATTCTCCATGACCCAAAATGCTGTGC 19114

19115 TTATGTCACTTACAGCTGTTAAAAAGCTTACTGGCATAAAGTTAACTTAT 19164

19165 GGTTATCTTAATGGTGTCCCAGTTAACACACATGAAGATAAACCTTTTAC 19214

19215 TTGGTATATTTACACTAGGAAGAACGGCAAGTTCGAGGACCATCCTGATG 19264

19265 GCTATTTTACCCAAGGTAGAACAACCGCTGATTTTAGCCCTCGTAGCGAC 19314

19315 ATGGAAAAGGACTTCCTAAGTATGGATATGGGTCTGTTTATTAACAAGTA 19364

19365 CGGACTTGAGGATTACGGCTTTGAGGCCGTTGTGTATGGTGATGTTTCAA 19414

19415 AAACCACCCTTGGTGGTTTGGCCCTACTAATTTCGCAGGTGCGTCTGGCC 19464

19465 TGTATGGGTGTGCTCAAAATAGACGAGTTTGTGTCTAGTAATGATAGCAC 19514

19515 CTTAAAGTCTTGTACTGTTACATATGCTGATAACCCTAGTAGTAAGATGG 19564

19565 TTTGTACGTATATGGATCTCCTGCTTGACGATTTTGTCAGCATTCTTAAA 19614

19615 TCTTTGGATTTGGGCGTTGTATCTAAAGTTCATGAAGTTATGGTCGATTG 19664

19665 TAAAATGTGGAGGTGGATGTTGTGGTGTAAGGATCATAAACTCCAGACAT 19714

19715 TTTATCCGCAACTTCAG 19731

PEDV Nsp15 amino acid (WT)

(SEQ ID NO: 7)

1 GLENIAFNVVKKGSFVGAEGELPVAVVNDKVLVRDGTVDTLVFTNKTSLP 50

51 TNVAFELYAKRKVGLTPPITILRNLGVVCTSKCVIWDYEAERPLTTFTKD 100

101 VCKYTDFEGDVCTLFDNSIVGSLERFSMTQNAVLMSLTAVKKLTGIKLTY 150

151 GYLNGVPVNTHEDKPFTWYIYTRKNGKFEDHPDGYFTQGRTTADFSPRSD 200

-continued

```
201 MEKDFLSMDMGLFINKYGLEDYGFEHVVYGDVSKTTLGGLHLLISQVRLA    250

251 CMGVLKIDEFVSSNDSTLKSCTVTYADNPSSKMVCTYMDLLLDDFVSILK    300

301 SLDLGVVSKVHEVMVDCKMWRWMLWCKDHKLQTFYPQLQ               339
```

PEDV Nsp15 amino acid (H226, H241 mutant)

(SEQ ID NO: 8)

```
  1 GLENIAFNVVKKGSFVGAEGELPVAVVNDKVLVRDGTVDTLVFTNKTSLP     50

 51 TNVAFELYAKRKVGLTPPITILRNLGVVCTSKCVIWDYEAERPLTTFTKD    100

101 VCKYTDFEGDVCTLFDNSIVGSLERFSMTQNAVLMSLTAVKKLTGIKLTY    150

151 GYLNGVPVNTHEDKPFTWYIYTRKNGKFEDHPDGYFTQGRTTADFSPRSD    200

201 MEKDFLSMDMGLFINKYGLEDYGFEAVVYGDVSKTTLGGLALLISQVRLA    250

251 CMGVLKIDEFVSSNDSTLKSCTVTYADNPSSKMVCTYMDLLLDDFVSILK    300

301 SLDLGVVSKVHEVMVDCKMWRWMLWCKDHKLQTFYPQLQ               339
```

PEDV Nsp16 nucleotide (WT)

(SEQ ID NO: 9)

```
19732 GCCAGTGAATGGAAGTGTGGTTATTCCATGCCTTCTATTTACAAGATACA  19781

19782 ACGTATGTGTTTAGAACCTTGCAATCTCTACAACTATGGTGCTGGTATTA  19831

19832 AGTTACCTGATGGCATTATGTTTAACGTAGTTAAATACACACAGCTTTGT  19881

19882 CAATATCTCAATAGCACCACAATGTGTGTACCCCATCACATGCGTGTGCT  19931

19932 ACATCTTGGTGCTGGCTCCGACAAGGGTGTTGCACCTGGCACGGCTGTCT  19981

19982 TACGACGTTGGTTGCCACTGGATGCCATTATAGTTGACAATGATAGTGTG  20031

20032 GATTACGTTAGCGATGCTGATTATAGTGTTACAGGAGATTGCTCTACCTT  20081

20082 ATACCTGTCAGATAAGTTTGATTTAGTTATATCTGATATGTATGATGGTA  20131

20132 AGATTAAAAGTTGTGATGGGGAGAACGTGTCTAAAGAAGGCTTCTTTCCC  20181

20182 TATATTAATGGTGTCATCACCGAAAAGTTGGCACTTGGTGGTACTGTAGC  20231

20232 TATTAAGGTGACGGAGTTTAGTTGGAATAAGAAGTTGTATGAACTCATTC  20281

20282 AGAGGTTTGAGTATTGGACAATGTTCTGTACCAGTGTTAACACGTCATCG  20331

20332 TCACAGGCATTCTTAATTGGTCTTCACTATTTAGGTGATTTTGCAAGTGG  20381

20382 CGCTGTGATTGACGGCAACACTATGCATGCCAATTATATCTTCTGGCGTA  20431

20432 ATTCCACAATTATGACTATGTCTTACAATAGTGTACTTGATTTAAGCAAG  20481

20482 TTCAATTGTAAGCATAAGGCTACAGTTGTCATTAATTTAAAAGATTCATC  20531

20532 CATTAGTGATGTTGTGTTAGGTTTGTTGAAGAATGGTAAGTTGCTAGTGC  20581

20582 GTAATAATGACGCCATTTGTGCTTTTTCTAATCATTTGGTCAACCTAAAC  20631

20632 AAATGA                                              20637
```

PEDV Nsp16 nucleotide (D129 mutant)

(SEQ ID NO: 10)

```
19732 GCCAGTGAATGGAAGTGTGGTTATTCCATGCCTTCTATTTACAAGATACA  19781

19782 ACGTATGTGTTTAGAACCTTGCAATCTCTACAACTATGGTGCTGGTATTA  19831

19332 AGTTACCTGATGGCATTATGTTTAACGTAGTTAAATACACACAGCTTTGT  19881

19882 CAATATCTCAATAGCACCACAATGTGTGTACCCCATCACATGCGTGTGCT  19931

19932 ACATCTTGGTGCTGGCTCCGACAAGGGTGTTGCACCTGGCACGGCTGTCT  19981

19982 TACGACGTTGGTTGCCACTGGATGCCATTATAGTTGACAATGATAGTGTG  20031

20032 GATTACGTTAGCGATGCTGATTATAGTGTTACAGGAGATTGCTCTACCTT  20081

20082 ATACCTGTCAGATAAGTTTGATTTAGTTATATCTGCAATGTATGATGGTA  20131

20132 AGATTAAAAGTTGTGATGGGGAGAACGTGTCTAAAGAAGGCTTCTTTCCC  20181
```

-continued

```
20182 TATATTAATGGTGTCATCACCGAAAAGTTGGCACTTGGTGGTACTGTAGC   20231

20232 TATTAAGGTGACGGAGTTTAGTTGGAATAAGAAGTTGTATGAACTCATTC   20281

20282 AGAGGTTTGAGTATTGGACAATGTTCTGTACCAGTGTTAACACGTCATCG   20331

20332 TCAGAGGCATTCTTAATTGGTGTTCACTATTTAGCTGATTTTGCAAGTGG   20381

20382 CGCTGTGATTGACGGCAACACTATGCATGCCAATTATATCTTCTGGCGTA   20431

20432 ATTCCACAATTATGACTATGTCTTACAATAGTGTACTTGATTTAAGCAAC   20481

20482 TTCAATTGTAAGCATAAGGCTACAGTTGTCATTAATTTAAAAGATTCATC   20531

20532 CATTAGTGATGTTGTGTTAGGTTTGTTGAAGAATGGTAAGTTGCTAGTGC   20581

20582 GTAATAATGACGCCATTTCTGGTTTTTCTAATCATTTGGTCAACGTAAAC   20631

20632 AAATGA                                               20637
```

PEDV Nsp16 amino acid (WT)

(SEQ ID NO: 11)

```
  1 ASEWKCGYSMPSIYKIQRMCLEPCNLYNYGAGIKLPDGIMFNVVKYTQLC    50

 51 QYLNSTTMCVPHHMRVLHLGAGSDKGVAPGTAVLRRWLPLDAIIVDNDSV   100

101 DYVSDADYSVTGDCSTLYLSDKFDLVISDMYDGKIKSCDGENVSKEGFEP   150

151 YINGVITEKLALGGTVAIKVTEFSWNKKLYELIQRFEYWTMFCTSVNTSS   200

201 SEAFLIGVHYLGDFASGAVIDGNTMHANYIFWRNSTIMTMSYNSVLDLSK   250

251 FNCKHKATVVINLKDSSISDVVLGLLKNGKLLVRNNDAICGFSNHLVNVN   300

301 K
```

PEDV Nsp16 amino acid (D129 mutant)

(SEQ ID NO: 12)

```
  1 ASEWKCGYSMPSIYKIQRMCLEPCNLYNYGAGIKLPDGIMFNVVKYTQLC    50

 51 QYLNSTTMCVPHHMRVLHLGAGSDKGVAPGTAVLRRWLPLDAIIVDNDSV   100

101 DYVSDADYSVTGDCSTLYLSDKFDLVISAMYDGKIKSCDGENVSKEGFFP   150

151 YINGVITEKLALGGTVAIKVTEFSWNKKLYELIQRFEYWTMFCTSVNTSS   200

201 SEAFLIGVHYLGDFASGAVIDGNTMHANYIFWRNSTIMTMSYNSVLDLSK   250

251 FNCKHKATVVINLKDSSISDVVLGLLKNGKLLVRNNDAICGFSNHLVNVN   300

301 K
```

In one embodiment, the present disclosure provides an infectious clone of CoV porcine epidemic diarrhea virus (icPEDV), which was used to generate viruses with inactive versions of interferon antagonist nonstructural proteins 1, 15 and 16 individually, or combined in one virus designated "icPEDV-mut4." icPEDV-mut4 elicited the most robust interferon responses, which severely limited virus replication. As described herein, icPEDV-mut4 infection of piglets did not induce diarrhea, although virus replication was detected in gut epithelial cells, along with low levels of virus shedding. Importantly, icPEDV-mut4 infection elicited IgG and neutralizing antibody responses to PEDV. The present disclosure provides in various embodiments that Nsp1, Nsp15 and Nsp16 are virulence factors that contribute to the development of PEDV-induced diarrhea in swine. Thus, in various embodiments, inactivating these three CoV interferon antagonists is an approach for generating candidate vaccines to limit the replication and disease caused by enteric CoVs.

This approach of inactivating a viral interferon antagonist to attenuate pathogenic viruses has been successful for diverse viruses including poxviruses (Smith G L, 2018, Adv Virus Res 100:355-378; and Smith G L, 2013, J Gen Virol 94:2367-2392), influenza viruses (Marazzi I, et al., 2015, Curr Opin Microbiol 26:123-9; and Du Y et al., 2018, Science (80-) 359:290-296) and flaviviruses (Xu Y, et al., 2020, Nat Med 1-4.). This approach relies on the ability of the mutant virus to activate the host innate immune response, predominantly type I and type III IFNs. The IFNs and interferon stimulated genes (ISGs) generate a hostile environment that limits virus replication, while still allowing for sufficient virus replication to activate the adaptive immune response. The challenge in applying this approach to coronaviruses has been identifying a key antagonist, or a constellation of antagonists, to inactivate such that the virus replicates at a level that elicits a protective response, without causing any clinical disease.

Nsp16 is a 2'-O-methyltransferase that is important for modifying the viral RNA to mimic the methylation found in host mRNA, thus evading sensing by host pattern recognition receptors (Züst R, 2011, Nat Immunol 12:137-43). By targeting four residues in the conserved catalytic site of Nsp16 (KDKE) and substituting all four to alanine, Hou and co-workers showed that this enzyme was a virulence factor for PEDV strain 22A (Hou Y, et al., 2019, J Virol 93:e00406-19). However, they report that the Nsp16-KDKE4A mutant does not replicate as efficiently as the single Nsp16 mutant (D129A) in Vero cells, suggesting that mutating all four catalytic residues in Nsp16 impairs virus replication. Nsp1 contains a key residue required for disrupting interferon antagonism has been identified by overexpression studies (Zhang Q, et al., 2018, J Virol 92:e01677-17; and Zhang Q, Shi K, Yoo D, 2016, Virology 489:252-268), although the exact mechanism used by PEDV Nsp1 has not yet been elucidated (Narayanan K, et al., 2015, Virus Res 202:89-100). The present disclosure provides for the first time that disrupting Nsp1 F44A in the context of virus replication does result in an elevated interferon response. Thus, Nsp1 is an interferon antagonist and virulence factor for PEDV.

Nsp15 is a viral endoribonuclease that has been show to target the poly uridine residues at the 5'-end of the negative-sense RNA (Hackbart et al., 2020, Proc. Natl. Acad. Sci., doi.org/10.1073/pnas.1921485117). EndoU activity trims the viral negative sense RNA so that it is not recognized by the host pattern recognition receptor MDAS. The structure of CoV endoribonuclease has been solved, revealing two required histidine residues in the catalytic sites, and that mutation of either of these histidine residues to alanine inactivates the enzyme (Ricagno S, et al., 2006, Proc Natl Acad Sci 103:11892-11897; Ivanov K A, et al., 2004, Proc Natl Acad Sci U.S.A. 101:12694-12699; Bhardwaj K, 2004, J Virol 78:12218-12224; Xu X, 2006, J Virol 80:7909-7917). Using the murine CoV mouse hepatitis virus (MHV), inactivating a single catalytic site (H262A) of EndoU was shown to result in a virus that replicated efficiently in interferon receptor knockout cells, but was deficient for replication in interferon responsive cells (Deng X, et al., 2017, Proc Natl Acad Sci USA 114:E4251-E4260). Similar results were observed when a single catalytic site in the PEDV EndoU was inactivated, with robust replication of the mutant virus in Vero cells, but limited replication in PK1 cells. Importantly, this Nsp15 mutant virus was attenuated in piglets, with no mortality associated with administration of a very high dose inoculum (105 TCID50) (Deng X, et al., 2019, J Virol 93:e02000-18).

The combination mutant virus, icPEDV-mut4 described herein, replicated efficiently in Vero cells, elicited a robust type I and III IFN response in PK1 cells which limited virus replication, and was highly attenuated when administer to naive piglets. This mutant virus was able to replicate in enterocytes to a sufficient level to elicit an adaptive immune response, as documented by virus-specific IgG and neutralizing antibody in the serum. The results disclosed herein are in agreement with previous studies using mouse-adapted versions of SARS-CoV and MERS-CoV that documented the efficacy of combination attenuation strategies for generating live attenuated coronavirus vaccines (Menachery V D, et al., 2018, J Virol 92:e00710-18; Menachery V D, et al., 2017, MBio 8:e00665-17; and, Bolles M, et al., 2011, J Virol 85:12201-15). These studies focused on the combination of inactivation of Nsp16 (MTase) and ExoN (proof-reading activity) as a combination strategy that could be leveraged as a platform for generating vaccines for emerging coronaviruses. The results disclosed herein can be informative for SARS-CoV-2, which has also caused symptoms of diarrhea and evidence of shedding in the feces (Wang D, et al., 2020, JAMA; Huang C, et al., 2020, Lancet (London, England) 395:497-506; and Holshue M L, et al., 2020, N Engl J Med NEJMoa2001191). A recent study documented fecal shedding from children infected with SARS-CoV-2 (Xu Y, et al., 2020, Nat Med 1-4), and further studies are needed to determine if these children developed neutralizing antibodies to SARS-CoV-2. Furthermore, it is likely that SARS-CoV-2 emerged either directly or indirectly from a virus reservoir in bats (Zhou P, et al., 2020, Nature 1-4), where the virus replicates in the enteric tract. Understanding the virulence factors that allow coronavirus replication in the enteric tract, such as Nsps 1, 15 and 16, is critical for generating effective candidate vaccines.

Methods of Using Coronavirus Vaccine Compositions

The coronaviruses and compositions and methods disclosed herein are useful, in various embodiments, to treat, prevent, and ameliorate at least one symptom of diseases or disorders associated with coronavirus infection. In this way, subjects such as mammals and, in non-limiting examples, pigs or swine, including sows, piglets, boars and gilts, and humans are contemplated as recipients. In one embodiment, the subject is human. In other embodiments, the subject is a bovine, canine, or primate.

The present disclosure includes coronaviruses and compositions that comprise coronavirus vaccine components, such as a live attenuated CoV, as described herein. In some embodiments, the composition is an antigenic composition. In some embodiments, the composition further comprises a pharmaceutically acceptable carrier. The term carrier encompasses diluents, excipients, adjuvants and combinations thereof. Pharmaceutically acceptable carriers are well known in the art (see, e.g., Remington's Pharmaceutical Sciences by Martin, 1975).

Exemplary "diluents" include sterile liquids such as sterile water, saline solutions, and buffers (e.g., phosphate, tris, borate, succinate, or histidine). Exemplary "excipients" are inert substances that may enhance vaccine stability and include but are not limited to polymers (e.g., polyethylene glycol), carbohydrates (e.g., starch, glucose, lactose, sucrose, or cellulose), and alcohols (e.g., glycerol, sorbitol, or xylitol).

The innate immune system comprises cells that provide defense in a non-specific manner to infection by other organisms. Innate immunity is an immediate defense but it is not long-lasting or protective against future challenges. Immune system cells that generally have a role in innate immunity are phagocytic, such as macrophages and dendritic cells. The innate immune system interacts with the adaptive (also called acquired) immune system in a variety of ways. Cells of the innate immune system can participate in antigen presentation to cells of the adaptive immune system, including expressing lymphokines that activate other cells, emitting chemotactic molecules that attract cells that may be specific to the invader, and secreting cytokines that recruit and activate cells of the adaptive immune system. The immunogenic/antigenic/vaccine compositions disclosed herein optionally include an agent that activates innate immunity in order to enhance the effectiveness of the composition.

Many types of agents can activate innate immunity. Organisms, like bacteria and viruses, can activate innate immunity, as can components of organisms, chemicals such as 2'-5' oligo A, bacterial endotoxins, RNA duplexes, single stranded RNA and other molecules. Many of the agents act through a family of molecules—the Toll-like receptors (TLRs). Engaging a TLR can also lead to production of cytokines and chemokines and activation and maturation of dendritic cells, components involved in development of acquired immunity. The TLR family can respond to a variety of agents, including lipoprotein, peptidoglycan, flagellin, imidazoquinolines, CpG DNA, lipopolysaccharide and double stranded RNA (Akira et al. Biochemical Soc Transactions 31: 637-642, 2003). These types of agents are sometimes called pathogen (or microbe)-associated molecular patterns.

In one aspect, one or more adjuvants are included in the composition, in order to provide an agent(s) that activates innate immunity. An adjuvant is a substance incorporated into or administered simultaneously with antigen that increases the immune response. A variety of mechanisms have been proposed to explain how different adjuvants work (e.g., antigen depots, activators of dendritic cells, macrophages). Without wishing to be bound by theory, one mechanism involves activating the innate immune system, resulting in the production of chemokines and cytokines, which in turn activate the adaptive (acquired) immune response. In particular, some adjuvants activate dendritic cells through TLRs. Thus, an adjuvant is one type of agent that activates the innate immune system that may be used in a vaccine described herein. An adjuvant may act to enhance an acquired immune response in other ways too. Preferably the adjuvant is a TLR4 agonist.

One adjuvant that may be used in the compositions described herein is a monoacid lipid A (MALA) type molecule. An exemplary MALA is MPL adjuvant as described in, e.g., Ulrich J. T. and Myers, K. R., "Monophosphoryl Lipid A as an Adjuvant" Chapter 21 in Vaccine Design, the Subunit and Adjuvant Approach, Powell, M. F. and Newman, M. J., eds. Plenum Press, N.Y. 1995. The adjuvant may be alum, where this term refers to aluminum salts, such as aluminum phosphate (A1PO4) and aluminum hydroxide (Al(OH)3). The adjuvant may be an emulsion having vaccine adjuvant properties. Such emulsions include oil-in-water emulsions. Freund's incomplete adjuvant (IFA) is one such adjuvant. Another suitable oil-in-water emulsion is MF59™ adjuvant which contains squalene, polyoxyethylene sorbitan monooleate (also known as Tween™ 80 surfactant) and sorbitan trioleate. Squalene is a natural organic compound originally obtained from shark liver oil, although also available from plant sources (primarily vegetable oils), including amaranth seed, rice bran, wheat germ, and olives. Other suitable emulsion adjuvants are Montanide™ adjuvants (Seppic Inc., Fairfield NJ) including Montanide™ ISA 50V which is a mineral oil-based adjuvant, Montanide™ ISA 206, and Montanide™ IMS 1312. While mineral oil may be present in the adjuvant, in one embodiment, the oil component(s) of the compositions of the present invention are all metabolizable oils.

The adjuvant may be AS02™ adjuvant or ASO4™ adjuvant. AS02™ adjuvant is an oil-in-water emulsion that contains both MPL™ adjuvant and QS-21™ adjuvant (a saponin adjuvant discussed elsewhere herein). ASO4™ adjuvant contains MPL™ adjuvant and alum. The adjuvant may be Matrix-M™ adjuvant (Novavax).

The adjuvant may be a saponin such as those derived from the bark of the Quillaja saponaria tree species, or a modified saponin, see, e.g., U.S. Pat. Nos. 5,057,540; 5,273,965; 5,352,449; 5,443,829; and 5,560,398. The product QS-21™ adjuvant sold by Antigenics, Inc. Lexington, MA is an exemplary saponin-containing co-adjuvant that may be used with the adjuvant of formula (1). Related to the saponins is the ISCOM™ family of adjuvants, originally developed by Iscotec (Sweden) and typically formed from saponins derived from Quillaja saponaria or synthetic analogs, cholesterol, and phospholipid, all formed into a honeycomb-like structure.

The adjuvant may be a cytokine that functions as an adjuvant, see, e.g., Lin R. et al. Clin. Infec. Dis. 21(6):1439-1449 (1995); Taylor, C. E., Infect. Immun. 63(9):3241-3244 (1995); and Egilmez, N. K., Chap. 14 in Vaccine Adjuvants and Delivery Systems, John Wiley & Sons, Inc. (2007). In various embodiments, the cytokine may be, e.g., granulocyte-macrophage colony-stimulating factor (GM-CSF); see, e.g., Change D. Z. et al. Hematology 9(3):207-215 (2004), Dranoff, G. Immunol. Rev. 188:147-154 (2002), and U.S. Pat. No. 5,679,356; or an interferon, such as a type I interferon, e.g., interferon-α (IFN-α) or interferon-β (IFN-β), or a type II interferon, e.g., interferon-γ (IFN-γ), see, e.g., Boehm, U. et al. Ann. Rev. Immunol. 15:749-795 (1997); and Theofilopoulos, A. N. et al. Ann. Rev. Immunol. 23:307-336 (2005); an interleukin, specifically including interleukin-1α (IL-1α), interleukin-1β (IL-1β), interleukin-2 (IL-2); see, e.g., Nelson, B. H., J. Immunol. 172(7):3983-3988 (2004); interleukin-4 (IL-4), interleukin-7 (IL-7), interleukin-12 (IL-12); see, e.g., Portielje, J. E., et al., Cancer Immunol. Immunother. 52(3): 133-144 (2003) and Trinchieri. G. Nat. Rev. Immunol. 3(2):133-146 (2003); interleukin-15 (Il-15), interleukin-18 (IL-18); fetal liver tyrosine kinase 3 ligand (Flt3L), or tumor necrosis factor α (TNFα).

The present disclosure includes methods for eliciting an immune response in a subject (e.g., a mammalian subject such as an animal or human), comprising administering to the subject an effective amount of a composition, e.g., a vaccine composition, comprising a live, attenuated coronavirus described herein. Unless otherwise indicated, the composition is an immunogenic composition. The methods include administration of a vaccine composition to a subject wherein the subject has not previously been infected with coronavirus. Additionally, the methods include administration of a vaccine composition to a subject wherein the subject is infected by coronavirus and optionally experiencing one or more symptoms of coronavirus infection. Additionally, the methods include administration of a vaccine composition to a subject that has recovered from a coronavirus infection.

The immune response raised by the methods of the present disclosure may, in various embodiments, include an antibody response, preferably a neutralizing antibody response, antibody dependent cell-mediated cytotoxicity (ADCC), antibody cell-mediated phagocytosis (ADCP), complement dependent cytotoxicity (CDC), and T cell-mediated response such as $CD4^+$, $CD8^+$. In some embodiments, the immune response comprises a T cell-mediated response (e.g., peptide-specific response such as a proliferative response or a cytokine response). In preferred embodiments, the immune response comprises both a B cell and a T cell response. Vaccine compositions can be administered in a number of suitable ways, such as intramuscular injection, subcutaneous injection, intradermal administration and mucosal administration such as oral or intranasal. Additional modes of administration include but are not limited to intranasal administration, intra-vaginal, intra-rectal, and oral administration. A combination of different routes of administration in the immunized subject, for example intramuscular and intranasal administration at the same time, is also contemplated by the disclosure.

Administration can involve a single dose or a multiple dose schedule. Multiple doses may be used in a primary immunization schedule and/or in a booster immunization schedule. In a multiple dose schedule the various doses may be given by the same or different routes, e.g., a parenteral prime and mucosal boost, or a mucosal prime and parenteral boost. Administration of more than one dose (typically two doses) is particularly useful in immunologically naive subjects or subjects of a (e.g., with respect to human subjects) hyporesponsive population (e.g., diabetics, or subjects with chronic kidney disease (e.g., dialysis patients)). In animals, administration of more than one dose may be particularly useful to circumvent the hyporesponsive effect of passively acquired immunity. Multiple doses, in some embodiments, can be administered at least 1 week apart (e.g., about 2 weeks, about 3 weeks, about 4 weeks, about 6 weeks, about 8 weeks, about 10 weeks, about 12 weeks, or about 16 weeks). Preferably multiple doses are administered from one, two, three, four or five months apart. Administration may be during gestation comprising one or more doses to confer maximum passive immunity (e.g., in the case of vaccinating a sow to provide passively acquired immunity to swine enteric coronaviruses). Vaccine compositions of the present disclosure may be administered to patients at substantially the same time as (e.g., during the same medical consultation or visit to a healthcare professional) other vaccines.

In various embodiments, a range of dosages for piglets from 1 to 14 days old, e.g., 1, 2, 3, 4, 5, 6, 7, 8, 9, 10, 11, 12, 13, 14 or more days old, with oral doses from 100 TCID50 and up to 10,000 TCID50 (Deng et al., 2017) are provided herein. In some embodiments, 100, 200, 300, 400, 500, 600, 700, 800, 900, 1,000, 2,000, 3,000, 4,000, 5,000, 6,000, 7,000, 8,000, 9,000 or 10,000 TCID50 are contemplated. For adult swine, dosage could be by a route known in the art and as described above. In some embodiments, oral administration or intramuscular injection, either alone, or in combination with other routes and optionally in combination with other vaccines, is contemplated. Dosage for adult swine may range from 100 TCID50 to 1,000,000 TCID50 (e.g., 100, 200, 300, 400, 500, 600, 700, 800, 900, 1,000, 2,000, 3,000, 4,000, 5,000, 6,000, 7,000, 8,000, 9,000, 10,000, 100,000, 500,000 or 1,000,000 TCID50) per animal depending on the route of administration, whether the animal is pregnant, and the age of the animal. For adult swine, multiple administrations (e.g., 2, 3, 4, 5, 6, 7, 8, 9, 10 or more) over the course of 3 months to 1 year (e.g., 3, 4, 5, 6, 7, 8, 9, 10, 11, 12 or more months) are contemplated to generate a maximal protective response.

In general, the amount of coronavirus in each dose of the vaccine composition is selected as an amount effective to induce an immune response in the subject, without causing significant, adverse side effects in the subject. Preferably the immune response elicited includes: neutralizing antibody response; antibody dependent cell-mediated cytotoxicity (ADCC); antibody cell-mediated phagocytosis (ADCP); complement dependent cytotoxicity (CDC); T cell-mediated response such as $CD4^+$, $CD8^+$, or a protective antibody response. Protective in this context does not necessarily require that the subject is completely protected against infection. A protective response is achieved when the subject is protected from developing symptoms of disease, especially severe disease associated with the pathogen corresponding to the heterologous antigen. As described above, the immune response generated by the composition comprising coronavirus as disclosed herein generates an immune response that recognizes, and preferably ameliorates and/or neutralizes, coronavirus.

Methods of treating a subject infected with a coronavirus or preventing a coronavirus infection in a subject are contemplated as described herein.

Methods of preparing a coronavirus vaccine composition are also contemplated. As described herein, given the high degree of conservation among all coronaviruses, the present disclosure provides that the mutations described, for example, with respect to PEDV are informative to preparing and using coronavirus vaccines comprising NSP mutations in coronaviruses other than PEDV, including coronaviruses that have not yet emerged. Although specific proteins and amino acids are identified in the context of, for example, PEDV in one embodiment herein, one of skill in the art will readily appreciate that, provided the high degree of conservation, other CoVs and CoV strains may similarly be mutated to practice the methods described herein.

As used herein, the term “at least,” for the example the phrase “at least one” means one or more, including one, two, three and so on.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a,” “and,” and “the” include plural referents unless the context clearly dictates otherwise. Thus, for example, reference to “a conformation switching probe” includes a plurality of such conformation switching probes and reference to “the microfluidic device” includes reference to one or more microfluidic devices and equivalents thereof known to those skilled in the art, and so forth. It is further noted that the claims may be drafted to exclude any element, e.g., any optional element. As such, this statement is intended to serve as antecedent basis for use of such exclusive terminology as “solely,” “only” and the like in connection with the recitation of claim elements, or use of a “negative” limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

EXAMPLES

The following materials and methods were used in association with the numerous embodiments provided herein and in the Examples that follow.

Cells and virus. Porcine kidney epithelial cells, LLC-PK1 (#ATCC-CL101), termed PK1 cells, were purchased from the ATCC and grown in growth medium containing modified Eagle medium (MEM) (Corning, 10010CV) supplemented with heat-inactive 5% fetal calf serum (FCS) (Atlanta Biological) and 1% Pen/Strep (Hyclone). Vero cells [USDA Animal and Plant Health INspection Agency, National Veterinary Services Laboratory (APHIS-NVSL)] were grown in growth media containing MEM (Gibco, 41500-018) supplemented with 10% FCS, 0.5% lactalbumin enzymatic hydrolysate (Sigma, 68458-87-7), and 1% pen/strep.

An infectious clone of PEDV wild-type (icPEDV-WT) and a PEDV mutant expressing catalytic-inactive endoribonuclease (icPEDV-EnUmt) were generated in our previous study (Deng X, et al., 2019, J Virol 93:e02000-18). A similar approach was used to engineer icPEDV-Nsp1mt, icPEDV-Nsp16mt, and icPEDV-mut4. icPEDV-Nsp1mt expresses a mutated Nsp1 that carries a Phe44-to-Ala substitution. icPEDV-Nsp16mt encodes a catalytic-inactive 2'-O-Methyltransferase which harbors an $Asp_{129}$-to-Ala mutation in Nsp16. icPEDV-mut4 has combined mutations in Nsp1 and Nsp16 in addition to two catalytic histidine mutations ($His_{226}$-to-Ala and $His_{241}$-to-Ala) of Nsp15. Primers used in the site-directed mutagenesis were listed in Table 1.

TABLE 1

| Mutagenesis primers | | |
|---|---|---|
| Targeted site | Forward | Reverse |
| Nsp1-F44A | TTTATGCAATGCCGTgcCGTGTCC TTCGATCT (SEQ ID NO: 13) | AGATCGAAGGACACGgcACGG CATTGCATAAA (SEQ ID NO: 14) |
| Nsp15-H226A | GATTACGGCTTTGAG**gcC**GTTGT GTATGGTGAT (SEQ ID NO: 15) | ATCACCATACACAACGgcCTCAA AGCCGTAATC (SEQ ID NO: 16) |
| Nsp15-H241A | ACCCTTGGTGGTTTG**gcc**CTACTA ATTTCGCAG (SEQ ID NO: 17) | CTGCGAAATTAGTAGggcCAAAC CACCAAGGGT (SEQ ID NO: 18) |
| Nsp16-D129A | GATTTAGTTATATCT**Gca**ATGTATG ATGGTAAG (SEQ ID NO: 19) | CTTACCATCATACAT**TGC**AGATA TAACTAAATC (SEQ ID NO: 20) |

All recombinant PEDVs were rescued in Vero cells and sequenced to confirm the engineered mutations. To make large stocks, these viruses were propagated once more in Vero cells with maintenance media containing FCS-free growth media, 0.15% Bacto tryptose phosphate broth (29.5 g/L, Bectin Dickinson, Cat. 260300), and 2 μg/mL 6-(1-tosylamido-2-phenyl) ethyl chloromethyl ketone (TPCK)-treated trypsin (Worthington Biochemicals, LS003750). The culture medium of infected cells was harvested when ~90% cells showed cytopathic effect (CPE), titrated on Vero cell monolayers, and stored at −80° C.

Growth kinetics and titration of icPEDV-WT and mutant viruses. Vero or PK1 cells were seeded into a 24-well ($1.5\times10^5$ cells/well) plate, and infected with either icPEDV-WT or the designated mutant virus at a dose of 0.1$TCID_{50}$ per cell in the presence of 5 μg/mL trypsin. After one hour incubation, the inoculum was removed and replaced with serum-free maintenance medium. Cell culture supernatant was collected at the indicated time points after infection and subjected to titration in Vero cells using a standard $TCID_{50}$ assay as previously described (Deng X, et al., 2019, J Virol 93:e02000-18).

Analysis of gene expression using RT-qPCR. To measure mRNA levels in cells, $3\times10^5$ PK1 cells per well were plated in a 12-well plate 16 hours prior to infection. Cells were washed twice with PBS and infected with the indicated virus at a dose of 0.1 $TCID_{50}$ per cell in the presence of 5 μg/mL trypsin (Sigma, 59427C). Cells were harvested at different time points using RLT buffer provided by the RNeasy mini kit (QIAGEN, 74104) and total RNA was extracted as instructed by the manufacturer's protocol. 500 ng RNA was used for cDNA synthesis using the RT2 HT First Strand Kit (QIAGEN, 330411). Quantitative PCR (qPCR) was performed using RT2 SYBR Green qPCR mix (QIAGEN, 330502) in the Bio-Rad CFX96 system. The thermocycler was set as follows: one step at 95° C. (10 min), 40 cycles of 95° C. (15 s), 55° C. (1 min) and plate read, one step at 95° C. (10 s), and a melt curve from 65° C. to 95° C. at increments of 0.5° C./0.05 s. Samples were assayed in triplicate and data are representative of three independent experiments. The levels of mRNA were relative to β-actin mRNA and expressed as $2^{-\Delta CT}$ [$\Delta CT=C_{T(gene\ of\ interest)}-C_{T(GAPDH)}$] PCR primers used in this study are listed in Table 2.

TABLE 2

| qPCR primer and probe sequences | | | |
|---|---|---|---|
| Method | Target | Forward | Reverse |
| SYBR green | Porcine IFN-β | AGCAGATCTTCGGCATTCTC (SEQ ID NO: 21) | GTCATCCATCTGCCCATCAA (SEQ ID NO: 22) |
| | Porcine IFN-λ1 | ACTGTGATGCTGGACTTGG (SEQ ID NO: 23) | GCATCCTTGGCTTTCTTGAA G (SEQ ID NO: 24) |
| | Porcine GAPDH | ACCTCCACTACATGGTCTAC A (SEQ ID NO: 25) | ATGACAAGCTTCCCGTTCTC (SEQ ID NO: 26) |

TABLE 2-continued qPCR primer and probe sequences

| Method | Target | Forward | Reverse |
|---|---|---|---|
| | Porcine ISG54 | CTGGCAAAGAGCCCTAAGGA (SEQ ID NO: 27) | CTCAGAGGGTCAATGGAATTCC (SEQ ID NO: 28) |
| | Porcine N gene | CACTAACCTGGGTGTCAGAAA (SEQ ID NO: 29) | CGTGAAGTAGGAGGTGTGTTAG (SEQ ID NO: 30) |
| Taqman | PEDV N gene | GAATTCCCAAGGGCGAAAAT (SEQ ID NO: 31) | TTTTCGACAAATTCCGCATCT (SEQ ID NO: 32) |
| | N gene probe | FAM-CGTAGCAGCTTGCTTCGGACCCA-BHQ[a] (SEQ ID NO: 33) | |

[a]FAM, 6-carboxyfluorescein; BHQ, black hole quencher

Evaluating pathogenesis of icPEDV-WT and icPEDV-mut4. All animal work was performed according to Institutional Animal Care and Use Protocol guidelines (ACUP ARS-2017-603) at the National Animal Disease Center (NADC) in Ames, Iowa. Six pregnant sows free of clinical disease and negative for PEDV antibodies via IFA were purchased from a commercial farm and transported to NADC prior to farrowing. Piglets were weaned from sows between 3-6 days of age, given an iron injection, and ear tagged. Piglets were blocked by litter and assigned to 3 treatment groups: icPEDV-WT (n=13), icPEDV-mut4 (n=13), and controls (n=8). Each group was housed in a separate biosafety level-2 animal room, fed a diet of milk replacer and starter, and given ad libitum access to water. Twenty-four hours after weaning, piglets were orally inoculated with 2 mL of virus solution at a titer of 500 TCIDso/pig. Control pigs received 2 mL of media inoculum orally. Piglets were rectal swabbed and given a clinical diarrhea score on 0-10, 12, 14, 18, and 21 days post inoculation (dpi). Clinical diarrhea scores were assigned with the following criteria: 0=normal feces, 1=soft stool, 2=semiliquid stool, and 3=watery diarrhea. Rectal swabs were collected with a sterile polyester-tipped applicator (Puritan Medical Products, Guilford, ME) immersed in 3 mL of serum-free MEM. Blood was collected in serum separation tube (BD Vacutainer®, Franklin Lakes, NJ) and centrifuged to harvest serum on 0 and 21 dpi. Samples were stored at −80° C. until time of testing.

Two piglets from each group were euthanized on 2 dpi for collection of jejunum and ileum tissue samples. Intestinal sections were fixed in 10% neutral buffered formalin and routinely processed. All remaining animals were euthanized on 21 dpi. Euthanasia was performed with an intravenous administration of barbiturate (Fatal Plus, Vortech Pharmaceuticals, Dearborn, MI) following the manufacturer labeled dose.

PEDV RNA Quantification using Taqman PCR. Viral RNA was quantified from rectal swabs as previously described (Miller L C, et al., 2016, J Vet Diagnostic Investig 28:20-29). Briefly, RNA extraction was performed using the MagMAX™ Pathogen RNA/DNA kit (catalog no. 4462359; Applied Biosystems) following manufacturer's recommendations for fecal samples. Viral RNA was eluted into 90 μL of elution buffer. Following extraction, 5 μL of the nucleic acid templates were added to 20 μL of the Path-ID™ Multiplex One-Step RT-PCR reaction master mix (catalog no. 4442137, Applied Biosystems). Real-time RT-PCR was performed on an ABI 7500 Fast instrument run in standard mode with the following conditions: reverse transcription at 45° C. for 10 min and denaturation at 95° C. for 10 min, followed by 40 cycles of 95° C. for 15 sec and 60° C. for 45 sec. The primer and the probe were synthesized (Integrated DNA Technologies, Coralville, IA), listed in Table 2, and targeted a conserved region (nucleotides 941-1028) of the PEDV N gene with modifications specific to the PEDV strain USA/Colorado/2013 (GenBank, KF272920). PEDV genome copies were calculated based on a standard RNA transcript overlapping the target region.

Immunofluorescence assay to determine the titer of virus-specific IgG. In a 96-well plate, Vero cells were infected with PEDV at a dose of 0.1 $TCID_{50}$ per cell in the presence of 2 μg/ml trypsin. At 16 hours post-infection, cells were washed once with PBS and fixed with cold methanol/acetone (50%/50%, vol/vol) for 15 min at −20° C. Fixed cells were then blocked with PBS containing 5% FCS for 30 min at 37° C. and incubated with serially diluted pig serum for 1 hour at 37° C. Cells were washed three times with PBS and incubated with FITC-conjugated goat anti-swine IgG (H+L) secondary antibody (6050-02, Southern Biotech). Subsequently, cells were washed three times with PBS before examination using a fluorescence microscope.

Viral neutralizing antibody determination. The details of this method was described previously (Hou Y, 2019, J Virol 93:e00406-19). Briefly, the collected sera were first heat-inactivated at 56° C. for 30 minutes and serially 4-fold diluted with MEM. Diluted sera were then mixed with a same volume of virus solution containing 100 $TCID_{50}$/25 μL of icPEDV-WT. After incubating for 90 minutes at 37° C., the mixture was used to infect Vero cells in 96-well plates with controls of mock and virus-only infections. After one hour infection, the inoculum was discarded. The cells were washed three times with PBS and cultured with the maintenance medium containing 5 μg/mL of trypsin. After 3 days of infection, the titers of neutralizing antibody were determined by Reed and Muench Method (Reed L J, Muench H., 1938, Am J Epidemiol 27:493-497). The VN titer of a serum sample is the reciprocal of its dilution that gives no CPE in 50% wells.

H&E staining and immunohistochemistry. The details of this method was described previously (Deng X, et al., 2019, J Virol 93:e02000-18). Briefly, tissues were fixed in neutral buffered formalin, processed, and embedded in paraffin. Five-micron-thick sections were cut and stained with hematoxylin and eosin (H&E) stain utilizing a Tissue-Tek automated slide stainer (Sakura Finetek USA, Torrence, CA). A veterinary pathologist who was blind to the treatment groups evaluated sections of small intestine by light microscopy to identify location and subjectively assess villus atrophy and crypt hyperplasia. For immunohistochemistry, the tissue sections were mounted on positively charged glass slides and oven dried for 60 min at 60° C. Slides were deparaffinized and then rinsed three times in deionized water, followed by soaking in Tris buffer saline with Tween 20 for 5 min. Slides were placed in a Dako autostainer (Agilent, Santa Clara, CA) and run through a preprogrammed immunohistochemistry (IHC) protocol. The IHC protocol utilizes Protease XIV (Millipore Sigma, St. Louis, MO) for antigen retrieval, murine monoclonal antibody SD6-29 specific for the nucleocapsid of PEDV (62) at 1:1,000 dilution, Dako Envision+HRP (Agilent, Santa Clara, CA), and DAB substrate chromogen (Agilent, Santa Clara, CA). The slides were then counterstained in hematoxylin and cover slipped.

Example 1

Generating Interferon Antagonist Mutant Strains of PEDV-Colorado

The use of reverse genetics to generate an infectious clone of wild type PEDV-Colorado strain, and a strain containing a mutation in the catalytic histidine residue (H226A) of endoribonuclease/Nsp15 that inactivates enzyme activity was described previously These viruses were designated icPEDV-wt and icPEDV-EnUmt (Deng X, et al., 2019, J Virol 93:e02000-18; and US Publication No. 2018/0333482, each of which is incorporated by reference herein in their entireties). icPEDV-EnUmt was found to generate an earlier and more robust interferon response in cell culture, and was attenuated compared to the wild type virus in piglets. Using the same strategy of incorporating mutations to inactivate IFN antagonists, three new viruses were generated that contain mutations in either Nsp1, Nsp15, or Nsp16 (FIG. 1). The Nsp1 F44A mutation documented to inactivate IFN antagonism (Zhang Q, et al., 2018, J Virol 92:e01677-17; and Zhang Q, Shi K, Yoo D., 2016, Virology 489:252-268) was incorporated and designated this virus as icPEDV-Nsp1mt. Regarding the Nsp16 mutation, Hou and co-workers working with porcine CoV 22A found that a single alanine substitution in the KDKE catalytic site of the 2'-O-methyltransferase resulted in a replication competent strain of PEDV, whereas substitution of all four catalytic site residues resulted in lower levels of PEDV replication in Vero cells (Hou Y, 2019, J Virol 93:e00406-19). The single alanine substitution in the catalytic D129 site of Nsp16 in the PEDV-Colorado strain was incorporated, and this virus was designated icPEDV-Nsp16mt. Finally, the mutations in Nsp1 and Nsp16 with mutations that inactivate both catalytic histidine residues (H226A and H241A) of Nsp15 were incorporated into one virus and designated that virus icPEDV-mut4. As used herein, the designation for these icPEDVs are: WT, Nsp1mt, EnUmt, Nsp16mt, and mut4.

Example 2

Figure 2:
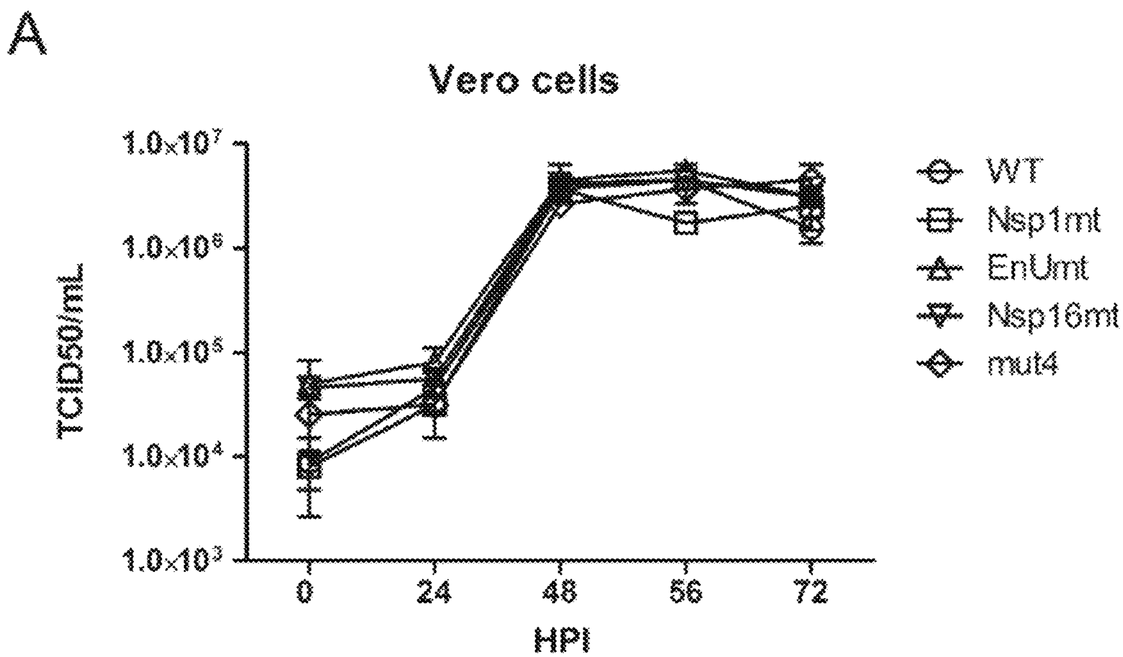
FIG. 2 shows an evaluation of the growth kinetics of icPEDV wild-type and Nsp-mutant viruses in Vero cells and PK1 cells. Vero (FIG. 2A) or PK1 (FIG. 2B) cells were infected with designated virus at a dose of 0.1 TCID50 per cell. Cell culture supernatants were collected at the indicated hours post-infection (HPI). The amount of infectious virus in the supernatant was titrated in Vero cells using a TCID50 assay in triplicate, and the results show the mean±SD. Data sets at the same time point were analyzed with an unpaired t-test. * and *** represent that the data sets between groups have statistic significant p-values at 48, 56 and 72 HPI. *, $p<0.05$; ***$p<0.001$.
Figure 2:
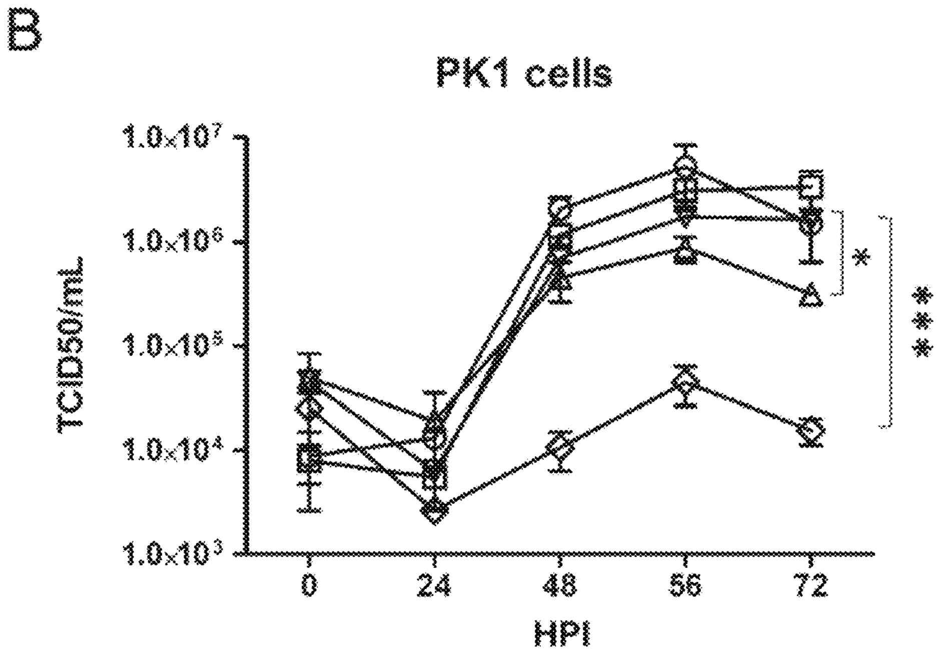

Evaluating Replication of IFN Antagonist Mutant Viruses in Vero Cells and PK1 Cells Inactivating EndoU by mutating the catalytic histidine residue H226A had no effect on virus replication in interferon non-responsive Vero cells, but replication was reduced in interferon responsive PK1 cells (Deng X, et al., 2019, J Virol 93:e02000-18). To determine if the mutation(s) that were introduced had any effect on virus replication, the replication kinetics of the viruses in Vero cells were compared over 72 hours. All four of the mutant viruses replicated efficiently in Vero cells, with kinetics that were similar to WT PEDV (FIG. 2A). These results are consistent with the concept that interferon antagonists are not required for virus replication in interferon-nonresponsive cells. The alanine substitutions in Nsp1, Nsp15 and Nsp16 in PEDV-mut4 had no detrimental effect on virus replication in Vero cells. In contrast to the results in Vero cells, replication of the EnUmt and mut4 were significantly reduced in PK1 cells, with mut4 reduce by 1000-fold compared to wild type PEDV (FIG. 2B). Since PK1 cells are interferon responsive, it is believed the mutant viruses were activating the expression of Type I and Type III interferons and interferon responsive genes (ISGs), which limited the production of infectious virus progeny over time.

Example 3

Evaluating the Kinetics of the IFN Response in PEDV-Infected PK1 Cells

Figure 3:
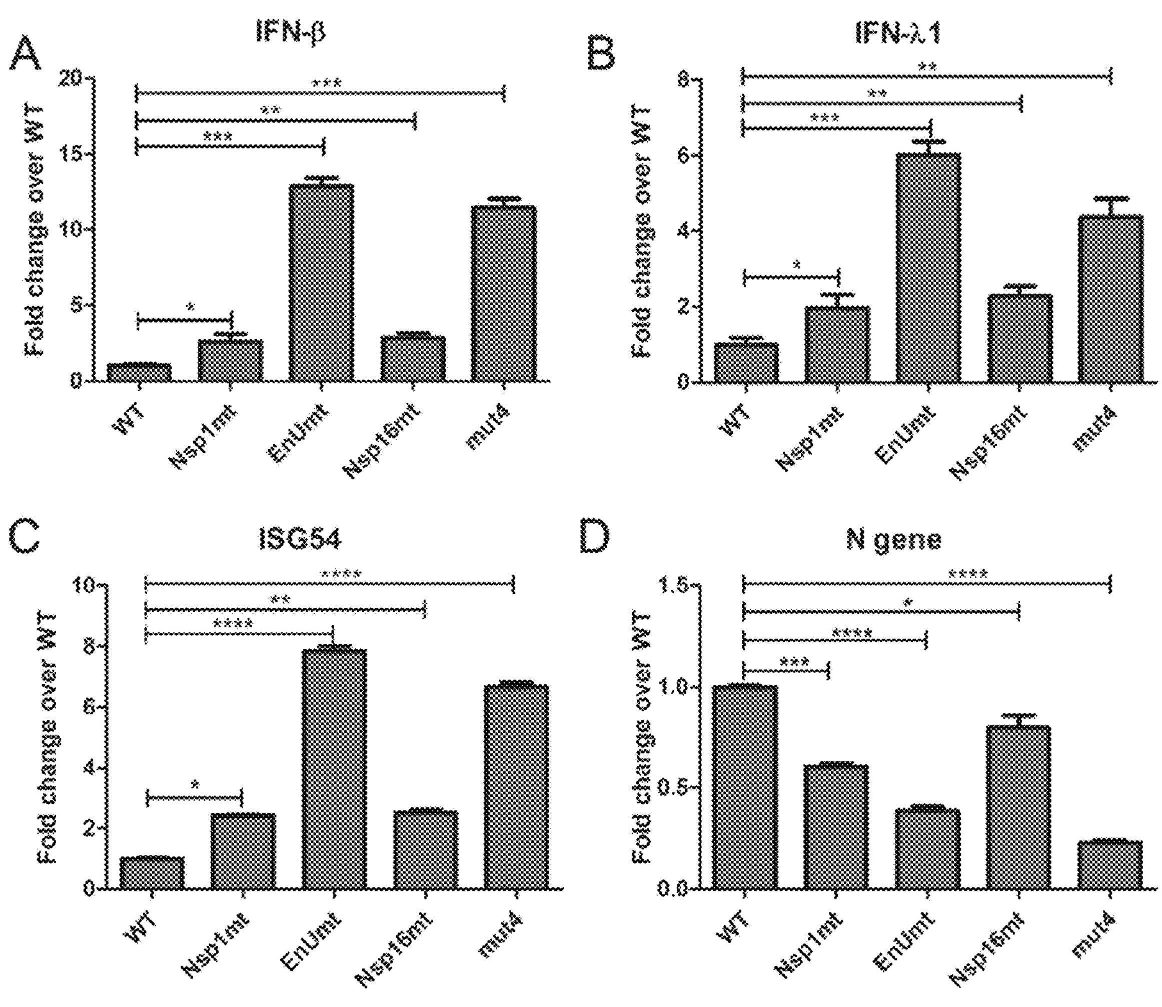
FIG. 3 shows an evaluation of the interferon responses to icPEDV infection in PK1 cells. PK1 cells were mock-infected or infected with the indicated strain of PEDV at a dose of 0.1 TCID50 per cell. At 24 HPI, cells were lysed to collect total RNA for cDNA synthesis, and quantitative PCR was used to measure the relative expression of the indicated mRNA. The level of gene expression in the wild-type virus-infected samples was set to 1, and the fold change in expression is relative to the PEDV wild-type virus-infected sample. Values are presented as mean±SD and analyzed with unpaired t-test. *, $p<0.05$; , $p<0.01$; *$p<0.001$; ****, $p<0.0001$.

PK1 cells were shown to respond to PEDV infection by activating the transcription of interferons (type I IFN-β and type III IFN-λ) and interferon stimulated genes, such as ISG54 (Deng X, et al., 2019, J Virol 93:e02000-18). To determine if inactivating multiple CoV interferon antagonists affected the IFN response to infection, PK1 cells were infected with the designated virus, incubated the infected cells for 24 hrs, harvested RNA from the cells, and performed RT-qPCR to evaluate the levels of expression of IFNs, ISG54 and the viral nucleocapsid (N) RNA. The relative expression of the target mRNA was compared to porcine GAPDH mRNA, the level of expression in PEDV-WT-infected cells was set to 1, and the fold change in gene expression detected in the mutant virus-infected cells was determined. The mutant virus-infected cells all had higher levels of IFNs and ISG54 as compared to the icPEDV-WT infected cells (FIG. 3A-C). Cells infected with icPEDV-EnUmt and the icPEDV-mut4 had the highest levels of IFN and ISG54 expression, with greater than 5-fold change compared to wild type PEDV infected cells. Viral replication was also evaluated by monitoring levels of PEDV N gene mRNA (FIG. 3D). We found that viral mRNA levels were significantly reduced in the mutant virus-infected cells, with icPEDV-mut4 being the most impaired. There was a correlation of high levels of IFN expression with reduced levels of viral RNA expression, consistent with the concept that IFN expression in PK1 cells is limiting virus replication. Both icPEDV-EnUmt and icPEDV-mut4 activate significantly higher levels of IFNs compared to the wild-type virus, and significantly lower levels of infectious particles were produced from the infected cells (FIGS. 3A-D and 1B).

Example 4

Evaluating the Pathogenesis of icPEDV-mut4 in Piglets

Figure 4:
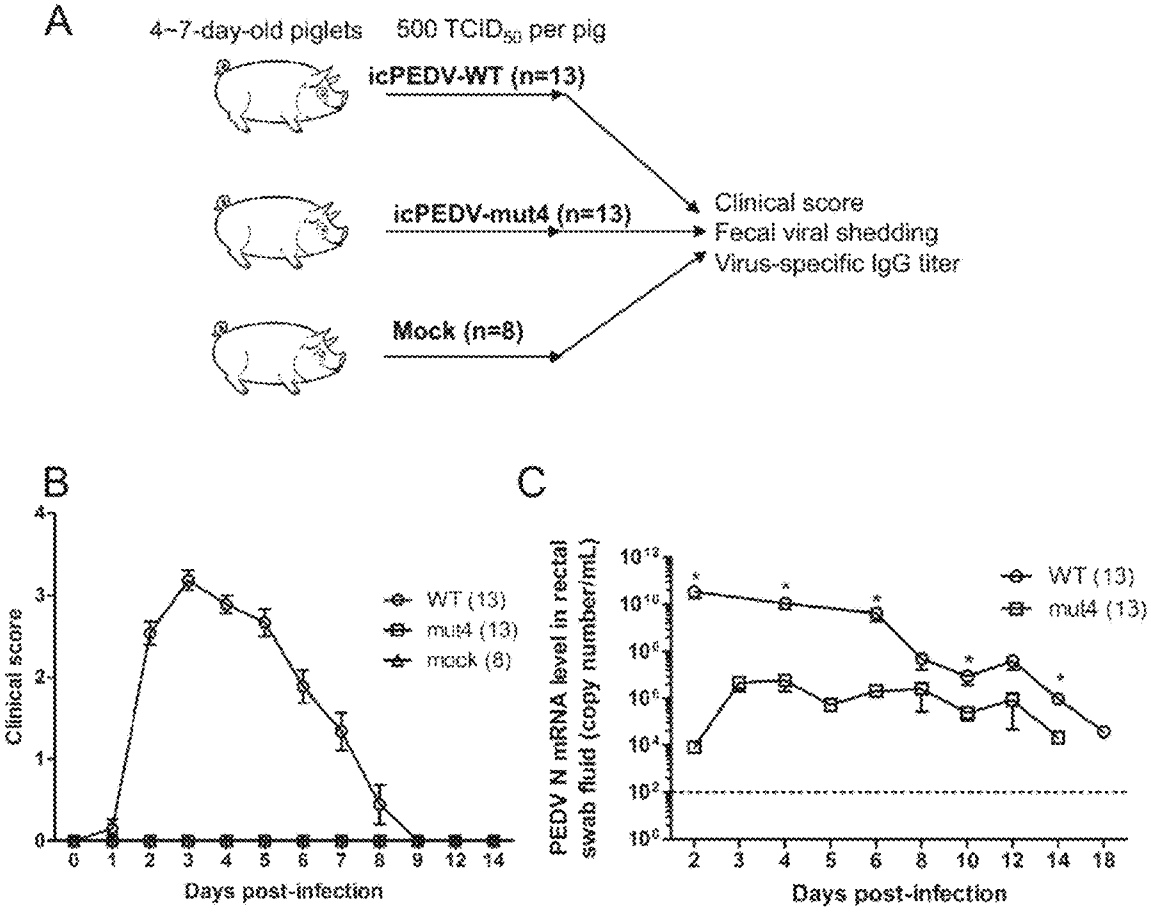
FIG. 4 shows experimental design and outcomes after PEDV infection.

Inoculation of piglets with icPEDV-WT was previously reported to result in significant disease and mortality in piglets, and that inoculation with icPEDV-EnUmt was associated with lower levels of virus shedding and no mortality (Deng X, et al., 2019, J Virol 93:e02000-18). In vitro studies indicated that icPEDV-mut4 induced similar levels of IFNs at 24 hrs post-infection as icPEDV-EnUmt, but that titer of infectious icPEDV-mut4 was significantly reduced in PK1 cells. Therefore, the pathogenesis of icPEDV-mut4 was evaluated in piglets and the results were compared to piglets inoculated with icPEDV-WT. For these studies, piglets from 3 sows were randomized into 3 groups (FIG. 4A). Piglets were orally inoculated with the designated virus (500 TCID50 per piglet), and monitored daily for signs of clinical disease. Fecal swabs were obtained from each piglet and PEDV RNA levels were determined by RT-qPCR. The icPEDV-WT-infected piglets all had signs of diarrhea (ranging from soft stool to watery diarrhea), as documented in the clinical score. In contrast, the icPEDV-mut4-infected animals showed no clinical signs of disease, similar to the mock-infected animals. By evaluating the shedding of viral RNA in the fecal swab, a significant reduction in the level of shedding in the icPEDV-mut4-infected animals was observed as compared to the icPEDV-WT-infected animals. 1010 copies of PEDV RNA/mL were detected in the fecal swabs from icPEDV-WT-infected animals at day 2 post-infection, compared to 104 copies of PEDV RNA/mL in the icPEDV-mut4-infected animals. The levels of virus shedding were consistently 100-1000 times lower in the fecal swabs of the icPEDV-mut4-infected animals compared to the icPEDV-WT-infected animals. The PEDV RNA in the fecal swab was below the limit of detection by day 18 post-infection in the icPEDV-mut4-infected animals.

Example 5

Figure 5:
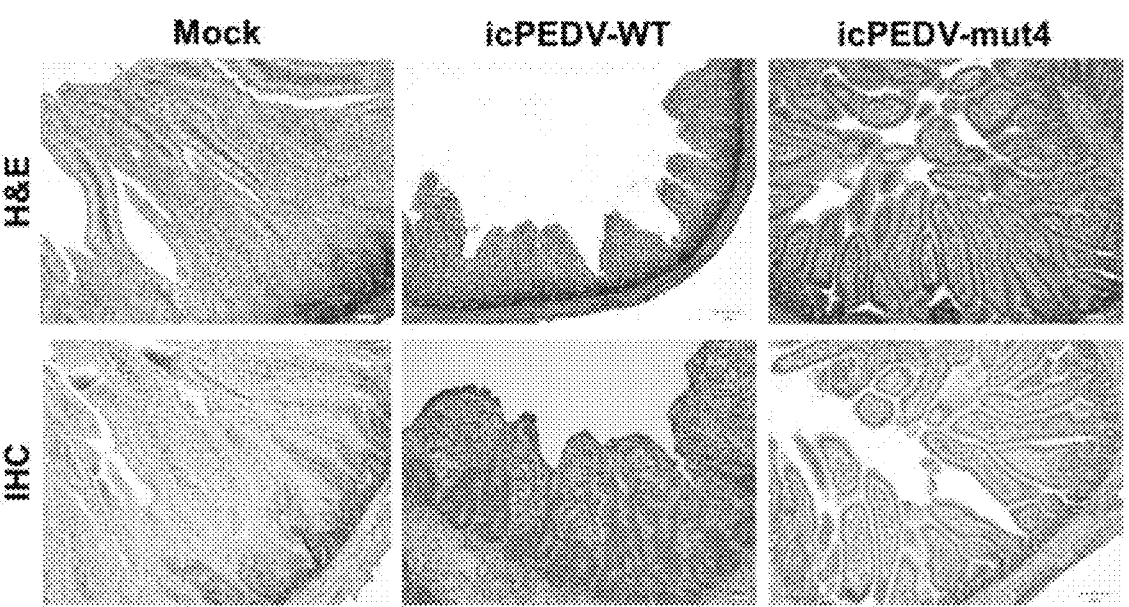
FIG. 5 shows histology and IHC staining of uninfected control, icPEDV-WT-, and icPEDV-mut4-infected piglet jejunum. Piglets were euthanized at day 2 post-infection. Images show representative histological slides of jejunum specimens visualized with H&E staining (upper panel, ×10), and immunohistochemistry (IHC) staining (lower panel, ×10) using mouse anti-PEDV-nucleocapsid antibody.

Analysis of icPEDV-WT and icPEDV-mut4 in the Small Intestine at Day 2 Post-Infection Histopathological examination of small intestine from the mock-infected control piglets and the icPEDV-mut4-infected piglets revealed no significant pathological lesions in either group. Intestinal villi were tall and lined by tall columnar epithelial cells. In contrast, piglets infected with icPEDV-WT exhibited classical microscopic lesions within sections of small intestine consisting of villus atrophy with degeneration and necrosis of villus tip enterocytes. Villus tip enterocytes were swollen and rounded to flattened, and were often separated from the underlying lamina. The superficial lamina was congested, and contained a few neutrophils. Immunohistochemistry (IHC) was utilized to detect PEDV nucleocapsid protein in all groups. Viral antigen was not detected by IHC within intestinal sections of the mock-infected control piglets or the icPEDV-mut4-infected piglets. Viral antigen was detected within mucosal epithelial cells of the icPEDV-WT-infected piglets. Representative images of sections of the jejunem are shown in FIG. 5.

Example 6

Figure 6:
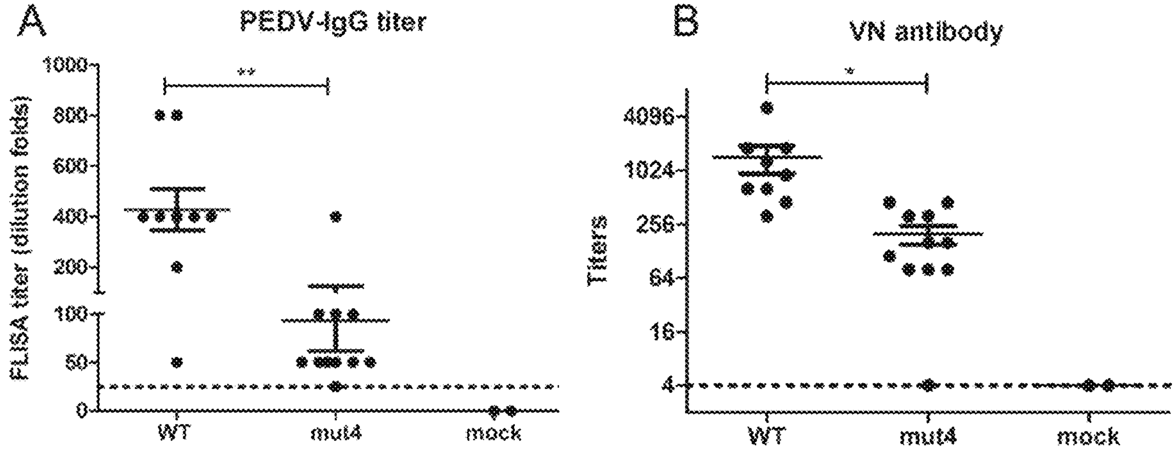
FIG. 6 shows virus-specific IgG titer and neutralizing antibody titer in sera collected from piglets infected with icPEDV wild-type or ic-PEDV-mut4.

Infection with icPEDV-mut4 Elicits Virus-Specific IGG Serum Antibodies with Neutralizing Activity To determine if the icPEDV-mut4-infected piglets generated an antibody response to the infection, serum samples were obtained at day 21 post-infection and used an immunofluorescence assay to evaluate the level of IgG to PEDV (Okda F, et al., 2015, BMC Vet Res 11:180). Except for the mock-infected group, all of icPEDV-WT and icPEDV-mut4-infected animals had a detectable level of PEDV-specific IgG (FIG. 6A). Higher titers were detected in the WT-infected piglets that exhibited clinical symptoms of disease. To determine the titers of neutralizing antibodies, a viral neutralizing (VN) assay was performed as described previously (Hou Y, 2019, J Virol 93:e00406-19). The sera sample collected from the icPEDV-WT-infected piglets contain high titers of neutralizing antibody. Similarly, the icPEDV-mut4-infected animals also generated neutralizing antibody, with an average titer of 1:256 (FIG. 6B). The VN titers of control sera were undetectable. Taken together, these results demonstrate that icPEDV-mut4 replicates in enterocytes and elicits a neutralizing antibody response in the piglets, without causing clinical signs of disease.

Taken together, the above Examples provide numerous embodiments including, but not limited to (a) inactivating three independent coronavirus interferon antagonists is an approach for attenuating a highly pathogenic, enteric coronavirus, (b) icPEDV-mut4 replicates as efficiently as wild type virus in Vero cells, but is highly impaired for replication in interferon responsive porcine kidney epithelial cells, (c) icPEDV-mut4-infected animals exhibited no clinical signs of disease (diarrhea), and (d) icPEDV-mut4 replicates in infected animals, as revealed by shedding of virus in the feces, and elicits an adaptive immune response, as revealed by detecting virus specific IgG and neutralizing antibody in the serum at 21 days post-infection. Thus, in one embodiment, inactivating three coronavirus interferon antagonists is an approach for generating live attenuated virus (LAV) coronavirus vaccine candidate strain.

What is claimed is:

1. A vaccine composition comprising a porcine epidemic diarrhea virus (PEDV) comprising one mutation in Nsp1, two mutations in Nsp15, and one mutation in Nsp16, wherein the mutation in Nsp1 is F44A as set out in SEQ ID NO: 4, the Nsp15 mutations are H226A and H241A as set out in SEQ ID NO: 8, and the Nsp16 mutation is D129A as set out in SEQ ID NO: 12, wherein said vaccine composition is capable of inducing an immune response in a non-human subject.

2. The vaccine composition of claim 1 wherein the PEDV is attenuated.

3. The vaccine composition of claim 2 wherein said immune response comprises interferon production, interferon-induced protein with tetratricopeptide repeats 2 (IFIT2 or ISG54) production, and antibody production.

4. The vaccine composition of claim 3 wherein said interferon production comprises type I IFN-β and type III IFN-λ production.

5. The vaccine composition of claim 3 wherein said interferon production is 2-fold above the level produced from wild-type PEDV infection.

6. The vaccine composition of claim 3 wherein said immune response comprises a neutralizing antibody response.

7. A method of inducing an immune response associated with a PEDV comprising administering a vaccine composition to a non-human subject, said composition comprising one mutation in Nsp1, two mutations in Nsp15, and one mutation in Nsp16, wherein the mutation in Nsp1 is F44A as set out in SEQ ID NO: 4, the Nsp15 mutations are H226A and H241A as set out in SEQ ID NO: 8, and the Nsp16 mutation is D129A as set out in SEQ ID NO: 12.

8. The method of claim 7, wherein said vaccine composition is capable of inducing type I IFN-β and type III IFN-λ production and a neutralizing antibody response.

* * * * *

SEQUENCE LISTING

<160> NUMBER OF SEQ ID NOS: 35

<210> SEQ ID NO 1
<211> LENGTH: 330
<212> TYPE: DNA
<213> ORGANISM: porcine epidemic diarrhea virus

<400> SEQUENCE: 1
atggctagca accatgttac attggctttt gccaatgatg cagaaatttc agcttttggc 60
ttttgcactg ctagtgaagc cgtctcatac tattctgagg ccgccgctag tggatttatg 120
caatgccgtt tcgtgtcctt cgatctcgct gacactgttg agggattgct tcccgaagac 180
tatgtcatgg tggtggtcgg cactaccaag cttagtgcgt atgtggacac ttttggtagc 240
cgccccaaaa acatttgtgg ttggctgtta ttttctaact gtaattactt cctcgaagag 300
ttagagctta cttttggtcg tcgtggtggt 330

<210> SEQ ID NO 2

<211> LENGTH: 330
<212> TYPE: DNA
<213> ORGANISM: porcine epidemic diarrhea virus

<400> SEQUENCE: 2
atggctagca accatgttac attggctttt gccaatgatg cagaaatttc agcttttggc 60
ttttgcactg ctagtgaagc cgtctcatac tattctgagg ccgccgctag tggatttatg 120
caatgccgtg ccgtgtcctt cgatctcgct gacactgttg agggattgct tcccgaagac 180
tatgtcatgg tggtggtcgg cactaccaag cttagtgcgt atgtggacac ttttggtagc 240
cgccccaaaa acatttgtgg ttggctgtta ttttctaact gtaattactt cctcgaagag 300
ttagagctta cttttggtcg tcgtggtggt 330

<210> SEQ ID NO 3
<211> LENGTH: 110
<212> TYPE: PRT
<213> ORGANISM: porcine epidemic diarrhea virus

<400> SEQUENCE: 3

Met Ala Ser Asn His Val Thr Leu Ala Phe Ala Asn Asp Ala Glu Ile
1 5 10 15

Ser Ala Phe Gly Phe Cys Thr Ala Ser Glu Ala Val Ser Tyr Tyr Ser
20 25 30

Glu Ala Ala Ala Ser Gly Phe Met Gln Cys Arg Phe Val Ser Phe Asp
35 40 45

Leu Ala Asp Thr Val Glu Gly Leu Leu Pro Glu Asp Tyr Val Met Val
50 55 60

Val Val Gly Thr Thr Lys Leu Ser Ala Tyr Val Asp Thr Phe Gly Ser
65 70 75 80

Arg Pro Lys Asn Ile Cys Gly Trp Leu Leu Phe Ser Asn Cys Asn Tyr
85 90 95

Phe Leu Glu Glu Leu Glu Leu Thr Phe Gly Arg Arg Gly Gly
100 105 110

<210> SEQ ID NO 4
<211> LENGTH: 110
<212> TYPE: PRT
<213> ORGANISM: porcine epidemic diarrhea virus

<400> SEQUENCE: 4

Met Ala Ser Asn His Val Thr Leu Ala Phe Ala Asn Asp Ala Glu Ile
1 5 10 15

Ser Ala Phe Gly Phe Cys Thr Ala Ser Glu Ala Val Ser Tyr Tyr Ser
20 25 30

Glu Ala Ala Ala Ser Gly Phe Met Gln Cys Arg Ala Val Ser Phe Asp
35 40 45

Leu Ala Asp Thr Val Glu Gly Leu Leu Pro Glu Asp Tyr Val Met Val
50 55 60

Val Val Gly Thr Thr Lys Leu Ser Ala Tyr Val Asp Thr Phe Gly Ser
65 70 75 80

Arg Pro Lys Asn Ile Cys Gly Trp Leu Leu Phe Ser Asn Cys Asn Tyr
85 90 95

Phe Leu Glu Glu Leu Glu Leu Thr Phe Gly Arg Arg Gly Gly
100 105 110

<210> SEQ ID NO 5
<211> LENGTH: 1017

<212> TYPE: DNA
<213> ORGANISM: porcine epidemic diarrhea virus

<400> SEQUENCE: 5
ggtcttgaga acattgcttt caatgtcgta aagaaaggat cttttgttgg tgccgaaggt 60
gaacttcctg tagctgtggt taatgacaaa gtgctcgtta gagatggtac tgttgatact 120
cttgttttta caaacaagac atcactaccc actaacgtag cttttgagtt gtatgccaag 180
cgtaaggtag gactcacccc acccattacg atcctacgta acttgggtgt agtttgtaca 240
tctaagtgtg tcatttggga ctatgaagcc gaacgtccac ttactacttt tacaaaggat 300
gtttgtaaat ataccgactt tgagggtgac gtctgtacac tctttgataa cagcattgtt 360
ggttcattag agcgattctc catgacccaa aatgctgtgc ttatgtcact tacagctgtt 420
aaaaagctta ctggcataaa gttaacttat ggttatctta atggtgtccc agttaacaca 480
catgaagata aacctttac ttggtatatt tacactagga agaacggcaa gttcgaggac 540
catcctgatg gctattttac ccaaggtaga acaaccgctg attttagccc tcgtagcgac 600
atggaaaagg acttcctaag tatggatatg ggtctgttta ttaacaagta cggacttgag 660
gattacggct ttgagcacgt tgtgtatggt gatgtttcaa aaaccaccct tggtggtttg 720
catctactaa tttcgcaggt gcgtctggcc tgtatgggtg tgctcaaaat agacgagttt 780
gtgtctagta atgatagcac gttaaagtct tgtactgtta catatgctga taaccctagt 840
agtaagatgg tttgtacgta tatggatctc ctgcttgacg attttgtcag cattcttaaa 900
tctttggatt tgggcgttgt atctaaagtt catgaagtta tggtcgattg taaaatgtgg 960
aggtggatgt tgtggtgtaa ggatcataaa ctccagacat tttatccgca acttcag 1017

<210> SEQ ID NO 6
<211> LENGTH: 1017
<212> TYPE: DNA
<213> ORGANISM: porcine epidemic diarrhea virus

<400> SEQUENCE: 6
ggtcttgaga acattgcttt caatgtcgta aagaaaggat cttttgttgg tgccgaaggt 60
gaacttcctg tagctgtggt taatgacaaa gtgctcgtta gagatggtac tgttgatact 120
cttgttttta caaacaagac atcactaccc actaacgtag cttttgagtt gtatgccaag 180
cgtaaggtag gactcacccc acccattacg atcctacgta acttgggtgt agtttgtaca 240
tctaagtgtg tcatttggga ctatgaagcc gaacgtccac ttactacttt tacaaaggat 300
gtttgtaaat ataccgactt tgagggtgac gtctgtacac tctttgataa cagcattgtt 360
ggttcattag agcgattctc catgacccaa aatgctgtgc ttatgtcact tacagctgtt 420
aaaaagctta ctggcataaa gttaacttat ggttatctta atggtgtccc agttaacaca 480
catgaagata aacctttac ttggtatatt tacactagga agaacggcaa gttcgaggac 540
catcctgatg gctattttac ccaaggtaga acaaccgctg attttagccc tcgtagcgac 600
atggaaaagg acttcctaag tatggatatg ggtctgttta ttaacaagta cggacttgag 660
gattacggct ttgaggccgt tgtgtatggt gatgtttcaa aaaccaccct tggtggtttg 720
gccctactaa tttcgcaggt gcgtctggcc tgtatgggtg tgctcaaaat agacgagttt 780
gtgtctagta atgatagcac gttaaagtct tgtactgtta catatgctga taaccctagt 840
agtaagatgg tttgtacgta tatggatctc ctgcttgacg attttgtcag cattcttaaa 900
tctttggatt tgggcgttgt atctaaagtt catgaagtta tggtcgattg taaaatgtgg 960

```
aggtggatgt tgtggtgtaa ggatcataaa ctccagacat tttatccgca acttcag      1017


<210> SEQ ID NO 7
<211> LENGTH: 339
<212> TYPE: PRT
<213> ORGANISM: porcine epidemic diarrhea virus

<400> SEQUENCE: 7

Gly Leu Glu Asn Ile Ala Phe Asn Val Val Lys Lys Gly Ser Phe Val
1               5                   10                  15

Gly Ala Glu Gly Glu Leu Pro Val Ala Val Val Asn Asp Lys Val Leu
            20                  25                  30

Val Arg Asp Gly Thr Val Asp Thr Leu Val Phe Thr Asn Lys Thr Ser
        35                  40                  45

Leu Pro Thr Asn Val Ala Phe Glu Leu Tyr Ala Lys Arg Lys Val Gly
    50                  55                  60

Leu Thr Pro Pro Ile Thr Ile Leu Arg Asn Leu Gly Val Val Cys Thr
65                  70                  75                  80

Ser Lys Cys Val Ile Trp Asp Tyr Glu Ala Glu Arg Pro Leu Thr Thr
                85                  90                  95

Phe Thr Lys Asp Val Cys Lys Tyr Thr Asp Phe Glu Gly Asp Val Cys
            100                 105                 110

Thr Leu Phe Asp Asn Ser Ile Val Gly Ser Leu Glu Arg Phe Ser Met
        115                 120                 125

Thr Gln Asn Ala Val Leu Met Ser Leu Thr Ala Val Lys Lys Leu Thr
    130                 135                 140

Gly Ile Lys Leu Thr Tyr Gly Tyr Leu Asn Gly Val Pro Val Asn Thr
145                 150                 155                 160

His Glu Asp Lys Pro Phe Thr Trp Tyr Ile Tyr Thr Arg Lys Asn Gly
                165                 170                 175

Lys Phe Glu Asp His Pro Asp Gly Tyr Phe Thr Gln Gly Arg Thr Thr
            180                 185                 190

Ala Asp Phe Ser Pro Arg Ser Asp Met Glu Lys Asp Phe Leu Ser Met
        195                 200                 205

Asp Met Gly Leu Phe Ile Asn Lys Tyr Gly Leu Glu Asp Tyr Gly Phe
    210                 215                 220

Glu His Val Val Tyr Gly Asp Val Ser Lys Thr Thr Leu Gly Gly Leu
225                 230                 235                 240

His Leu Leu Ile Ser Gln Val Arg Leu Ala Cys Met Gly Val Leu Lys
                245                 250                 255

Ile Asp Glu Phe Val Ser Ser Asn Asp Ser Thr Leu Lys Ser Cys Thr
            260                 265                 270

Val Thr Tyr Ala Asp Asn Pro Ser Ser Lys Met Val Cys Thr Tyr Met
        275                 280                 285

Asp Leu Leu Leu Asp Asp Phe Val Ser Ile Leu Lys Ser Leu Asp Leu
    290                 295                 300

Gly Val Val Ser Lys Val His Glu Val Met Val Asp Cys Lys Met Trp
305                 310                 315                 320

Arg Trp Met Leu Trp Cys Lys Asp His Lys Leu Gln Thr Phe Tyr Pro
                325                 330                 335

Gln Leu Gln


<210> SEQ ID NO 8
<211> LENGTH: 339
<212> TYPE: PRT
```

<213> ORGANISM: porcine epidemic diarrhea virus

<400> SEQUENCE: 8

```
Gly Leu Glu Asn Ile Ala Phe Asn Val Val Lys Lys Gly Ser Phe Val
1               5                   10                  15

Gly Ala Glu Gly Glu Leu Pro Val Ala Val Val Asn Asp Lys Val Leu
            20                  25                  30

Val Arg Asp Gly Thr Val Asp Thr Leu Val Phe Thr Asn Lys Thr Ser
        35                  40                  45

Leu Pro Thr Asn Val Ala Phe Glu Leu Tyr Ala Lys Arg Lys Val Gly
    50                  55                  60

Leu Thr Pro Pro Ile Thr Ile Leu Arg Asn Leu Gly Val Val Cys Thr
65                  70                  75                  80

Ser Lys Cys Val Ile Trp Asp Tyr Glu Ala Glu Arg Pro Leu Thr Thr
                85                  90                  95

Phe Thr Lys Asp Val Cys Lys Tyr Thr Asp Phe Glu Gly Asp Val Cys
            100                 105                 110

Thr Leu Phe Asp Asn Ser Ile Val Gly Ser Leu Glu Arg Phe Ser Met
        115                 120                 125

Thr Gln Asn Ala Val Leu Met Ser Leu Thr Ala Val Lys Lys Leu Thr
    130                 135                 140

Gly Ile Lys Leu Thr Tyr Gly Tyr Leu Asn Gly Val Pro Val Asn Thr
145                 150                 155                 160

His Glu Asp Lys Pro Phe Thr Trp Tyr Ile Tyr Thr Arg Lys Asn Gly
                165                 170                 175

Lys Phe Glu Asp His Pro Asp Gly Tyr Phe Thr Gln Gly Arg Thr Thr
            180                 185                 190

Ala Asp Phe Ser Pro Arg Ser Asp Met Glu Lys Asp Phe Leu Ser Met
        195                 200                 205

Asp Met Gly Leu Phe Ile Asn Lys Tyr Gly Leu Glu Asp Tyr Gly Phe
    210                 215                 220

Glu Ala Val Val Tyr Gly Asp Val Ser Lys Thr Thr Leu Gly Gly Leu
225                 230                 235                 240

Ala Leu Leu Ile Ser Gln Val Arg Leu Ala Cys Met Gly Val Leu Lys
                245                 250                 255

Ile Asp Glu Phe Val Ser Ser Asn Asp Ser Thr Leu Lys Ser Cys Thr
            260                 265                 270

Val Thr Tyr Ala Asp Asn Pro Ser Ser Lys Met Val Cys Thr Tyr Met
        275                 280                 285

Asp Leu Leu Leu Asp Asp Phe Val Ser Ile Leu Lys Ser Leu Asp Leu
    290                 295                 300

Gly Val Val Ser Lys Val His Glu Val Met Val Asp Cys Lys Met Trp
305                 310                 315                 320

Arg Trp Met Leu Trp Cys Lys Asp His Lys Leu Gln Thr Phe Tyr Pro
                325                 330                 335

Gln Leu Gln
```

<210> SEQ ID NO 9
<211> LENGTH: 906
<212> TYPE: DNA
<213> ORGANISM: porcine epidemic diarrhea virus

<400> SEQUENCE: 9

```
gccagtgaat ggaagtgtgg ttattccatg ccttctattt acaagataca acgtatgtgt      60
```

```
ttagaacctt gcaatctcta caactatggt gctggtatta agttacctga tggcattatg    120

tttaacgtag ttaaatacac acagctttgt caatatctca atagcaccac aatgtgtgta    180

ccccatcaca tgcgtgtgct acatcttggt gctggctccg acaagggtgt tgcacctggc    240

acggctgtct tacgacgttg gttgccactg gatgccatta tagttgacaa tgatagtgtg    300

gattacgtta gcgatgctga ttatagtgtt acaggagatt gctctacctt atacctgtca    360

gataagtttg atttagttat atctgatatg tatgatggta agattaaaag ttgtgatggg    420

gagaacgtgt ctaaagaagg cttctttccc tatattaatg gtgtcatcac cgaaaagttg    480

gcacttggtg gtactgtagc tattaaggtg acggagttta gttggaataa gaagttgtat    540

gaactcattc agaggtttga gtattggaca atgttctgta ccagtgttaa cacgtcatcg    600

tcagaggcat tcttaattgg tgttcactat ttaggtgatt ttgcaagtgg cgctgtgatt    660

gacggcaaca ctatgcatgc caattatatc ttctggcgta attccacaat tatgactatg    720

tcttacaata gtgtacttga tttaagcaag ttcaattgta agcataaggc tacagttgtc    780

attaatttaa aagattcatc cattagtgat gttgtgttag gtttgttgaa gaatggtaag    840

ttgctagtgc gtaataatga cgccatttgt ggtttttcta atcatttggt caacgtaaac    900

aaatga                                                               906
```

<210> SEQ ID NO 10
<211> LENGTH: 906
<212> TYPE: DNA
<213> ORGANISM: porcine epidemic diarrhea virus

<400> SEQUENCE: 10

```
gccagtgaat ggaagtgtgg ttattccatg ccttctattt acaagataca acgtatgtgt     60

ttagaacctt gcaatctcta caactatggt gctggtatta agttacctga tggcattatg    120

tttaacgtag ttaaatacac acagctttgt caatatctca atagcaccac aatgtgtgta    180

ccccatcaca tgcgtgtgct acatcttggt gctggctccg acaagggtgt tgcacctggc    240

acggctgtct tacgacgttg gttgccactg gatgccatta tagttgacaa tgatagtgtg    300

gattacgtta gcgatgctga ttatagtgtt acaggagatt gctctacctt atacctgtca    360

gataagtttg atttagttat atctgcaatg tatgatggta agattaaaag ttgtgatggg    420

gagaacgtgt ctaaagaagg cttctttccc tatattaatg gtgtcatcac cgaaaagttg    480

gcacttggtg gtactgtagc tattaaggtg acggagttta gttggaataa gaagttgtat    540

gaactcattc agaggtttga gtattggaca atgttctgta ccagtgttaa cacgtcatcg    600

tcagaggcat tcttaattgg tgttcactat ttaggtgatt ttgcaagtgg cgctgtgatt    660

gacggcaaca ctatgcatgc caattatatc ttctggcgta attccacaat tatgactatg    720

tcttacaata gtgtacttga tttaagcaag ttcaattgta agcataaggc tacagttgtc    780

attaatttaa aagattcatc cattagtgat gttgtgttag gtttgttgaa gaatggtaag    840

ttgctagtgc gtaataatga cgccatttgt ggtttttcta atcatttggt caacgtaaac    900

aaatga                                                               906
```

<210> SEQ ID NO 11
<211> LENGTH: 301
<212> TYPE: PRT
<213> ORGANISM: porcine epidemic diarrhea virus

<400> SEQUENCE: 11

```
Ala Ser Glu Trp Lys Cys Gly Tyr Ser Met Pro Ser Ile Tyr Lys Ile
```

```
1               5                   10                  15

Gln Arg Met Cys Leu Glu Pro Cys Asn Leu Tyr Asn Tyr Gly Ala Gly
            20                  25                  30

Ile Lys Leu Pro Asp Gly Ile Met Phe Asn Val Val Lys Tyr Thr Gln
        35                  40                  45

Leu Cys Gln Tyr Leu Asn Ser Thr Thr Met Cys Val Pro His His Met
    50                  55                  60

Arg Val Leu His Leu Gly Ala Gly Ser Asp Lys Gly Val Ala Pro Gly
65                  70                  75                  80

Thr Ala Val Leu Arg Arg Trp Leu Pro Leu Asp Ala Ile Ile Val Asp
                85                  90                  95

Asn Asp Ser Val Asp Tyr Val Ser Asp Ala Asp Tyr Ser Val Thr Gly
            100                 105                 110

Asp Cys Ser Thr Leu Tyr Leu Ser Asp Lys Phe Asp Leu Val Ile Ser
        115                 120                 125

Asp Met Tyr Asp Gly Lys Ile Lys Ser Cys Asp Gly Glu Asn Val Ser
    130                 135                 140

Lys Glu Gly Phe Phe Pro Tyr Ile Asn Gly Val Ile Thr Glu Lys Leu
145                 150                 155                 160

Ala Leu Gly Gly Thr Val Ala Ile Lys Val Thr Glu Phe Ser Trp Asn
                165                 170                 175

Lys Lys Leu Tyr Glu Leu Ile Gln Arg Phe Glu Tyr Trp Thr Met Phe
            180                 185                 190

Cys Thr Ser Val Asn Thr Ser Ser Ser Glu Ala Phe Leu Ile Gly Val
        195                 200                 205

His Tyr Leu Gly Asp Phe Ala Ser Gly Ala Val Ile Asp Gly Asn Thr
    210                 215                 220

Met His Ala Asn Tyr Ile Phe Trp Arg Asn Ser Thr Ile Met Thr Met
225                 230                 235                 240

Ser Tyr Asn Ser Val Leu Asp Leu Ser Lys Phe Asn Cys Lys His Lys
                245                 250                 255

Ala Thr Val Val Ile Asn Leu Lys Asp Ser Ser Ile Ser Asp Val Val
            260                 265                 270

Leu Gly Leu Leu Lys Asn Gly Lys Leu Leu Val Arg Asn Asn Asp Ala
        275                 280                 285

Ile Cys Gly Phe Ser Asn His Leu Val Asn Val Asn Lys
    290                 295                 300


<210> SEQ ID NO 12
<211> LENGTH: 301
<212> TYPE: PRT
<213> ORGANISM: porcine epidemic diarrhea virus

<400> SEQUENCE: 12

Ala Ser Glu Trp Lys Cys Gly Tyr Ser Met Pro Ser Ile Tyr Lys Ile
1               5                   10                  15

Gln Arg Met Cys Leu Glu Pro Cys Asn Leu Tyr Asn Tyr Gly Ala Gly
            20                  25                  30

Ile Lys Leu Pro Asp Gly Ile Met Phe Asn Val Val Lys Tyr Thr Gln
        35                  40                  45

Leu Cys Gln Tyr Leu Asn Ser Thr Thr Met Cys Val Pro His His Met
    50                  55                  60

Arg Val Leu His Leu Gly Ala Gly Ser Asp Lys Gly Val Ala Pro Gly
65                  70                  75                  80
```

```
Thr Ala Val Leu Arg Arg Trp Leu Pro Leu Asp Ala Ile Ile Val Asp
                85                  90                  95

Asn Asp Ser Val Asp Tyr Val Ser Asp Ala Asp Tyr Ser Val Thr Gly
            100                 105                 110

Asp Cys Ser Thr Leu Tyr Leu Ser Asp Lys Phe Asp Leu Val Ile Ser
        115                 120                 125

Ala Met Tyr Asp Gly Lys Ile Lys Ser Cys Asp Gly Glu Asn Val Ser
    130                 135                 140

Lys Glu Gly Phe Phe Pro Tyr Ile Asn Gly Val Ile Thr Glu Lys Leu
145                 150                 155                 160

Ala Leu Gly Gly Thr Val Ala Ile Lys Val Thr Glu Phe Ser Trp Asn
                165                 170                 175

Lys Lys Leu Tyr Glu Leu Ile Gln Arg Phe Glu Tyr Trp Thr Met Phe
            180                 185                 190

Cys Thr Ser Val Asn Thr Ser Ser Ser Glu Ala Phe Leu Ile Gly Val
        195                 200                 205

His Tyr Leu Gly Asp Phe Ala Ser Gly Ala Val Ile Asp Gly Asn Thr
    210                 215                 220

Met His Ala Asn Tyr Ile Phe Trp Arg Asn Ser Thr Ile Met Thr Met
225                 230                 235                 240

Ser Tyr Asn Ser Val Leu Asp Leu Ser Lys Phe Asn Cys Lys His Lys
                245                 250                 255

Ala Thr Val Val Ile Asn Leu Lys Asp Ser Ser Ile Ser Asp Val Val
            260                 265                 270

Leu Gly Leu Leu Lys Asn Gly Lys Leu Leu Val Arg Asn Asn Asp Ala
        275                 280                 285

Ile Cys Gly Phe Ser Asn His Leu Val Asn Val Asn Lys
    290                 295                 300
```

<210> SEQ ID NO 13
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 13
tttatgcaat gccgtgccgt gtccttcgat ct 32

<210> SEQ ID NO 14
<211> LENGTH: 32
<212> TYPE: DNA
<213> ORGANISM: Artificial Seqeucnce
<220> FEATURE:
<223> OTHER INFORMATION: Synthetic Polynucleotide

<400> SEQUENCE: 14
agatcgaagg acacggcacg gcattgcata aa 32

<210> SEQ ID NO 15
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 15
gattacggct ttgaggccgt tgtgtatggt gat 33

```
<210> SEQ ID NO 16
<211> LENGTH: 33
<212> TYPE: DNA
<213> ORGANISM: Artificial Seuqence
<220> FEATURE:
<223> OTHER INFORMATION: Synthetic Polynucleotide

<400> SEQUENCE: 16

atcaccatac acaacggcct caaagccgta atc                              33


<210> SEQ ID NO 17
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 17

acccttggtg gtttggccct actaatttcg cag                              33


<210> SEQ ID NO 18
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 18

ctgcgaaatt agtagggcca aaccaccaag ggt                              33


<210> SEQ ID NO 19
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 19

gatttagtta tatctgcaat gtatgatggt aag                              33


<210> SEQ ID NO 20
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 20

cttaccatca tacattgcag atataactaa atc                              33


<210> SEQ ID NO 21
<211> LENGTH: 20
<212> TYPE: DNA
<213> ORGANISM: Porcine

<400> SEQUENCE: 21

agcagatctt cggcattctc                                             20


<210> SEQ ID NO 22
<211> LENGTH: 20
<212> TYPE: DNA
<213> ORGANISM: Porcine

<400> SEQUENCE: 22

gtcatccatc tgcccatcaa                                             20
```

<210> SEQ ID NO 23
<211> LENGTH: 19
<212> TYPE: DNA
<213> ORGANISM: Porcine

<400> SEQUENCE: 23
actgtgatgc tggacttgg 19

<210> SEQ ID NO 24
<211> LENGTH: 21
<212> TYPE: DNA
<213> ORGANISM: Porcine

<400> SEQUENCE: 24
gcatccttgg ctttcttgaa g 21

<210> SEQ ID NO 25
<211> LENGTH: 21
<212> TYPE: DNA
<213> ORGANISM: Porcine

<400> SEQUENCE: 25
acctccacta catggtctac a 21

<210> SEQ ID NO 26
<211> LENGTH: 20
<212> TYPE: DNA
<213> ORGANISM: Porcine

<400> SEQUENCE: 26
atgacaagct tcccgttctc 20

<210> SEQ ID NO 27
<211> LENGTH: 20
<212> TYPE: DNA
<213> ORGANISM: Porcine

<400> SEQUENCE: 27
ctggcaaaga gccctaagga 20

<210> SEQ ID NO 28
<211> LENGTH: 22
<212> TYPE: DNA
<213> ORGANISM: Porcine

<400> SEQUENCE: 28
ctcagagggt caatggaatt cc 22

<210> SEQ ID NO 29
<211> LENGTH: 21
<212> TYPE: DNA
<213> ORGANISM: Porcine

<400> SEQUENCE: 29
cactaacctg ggtgtcagaa a 21

<210> SEQ ID NO 30
<211> LENGTH: 22
<212> TYPE: DNA
<213> ORGANISM: Porcine

<400> SEQUENCE: 30
cgtgaagtag gaggtgtgtt ag 22

<210> SEQ ID NO 31
<211> LENGTH: 20
<212> TYPE: DNA
<213> ORGANISM: Porcine

<400> SEQUENCE: 31
gaattcccaa gggcgaaaat 20

<210> SEQ ID NO 32
<211> LENGTH: 21
<212> TYPE: DNA
<213> ORGANISM: Porcine

<400> SEQUENCE: 32
ttttcgacaa attccgcatc t 21

<210> SEQ ID NO 33
<211> LENGTH: 23
<212> TYPE: DNA
<213> ORGANISM: Porcine
<220> FEATURE:
<221> NAME/KEY: misc_feature
<222> LOCATION: (1)..(1)
<223> OTHER INFORMATION: 5'- FAM
<220> FEATURE:
<221> NAME/KEY: misc_feature
<222> LOCATION: (23)..(23)
<223> OTHER INFORMATION: 3'- BHQ

<400> SEQUENCE: 33
cgtagcagct tgcttcggac cca 23

<210> SEQ ID NO 34
<211> LENGTH: 28062
<212> TYPE: DNA
<213> ORGANISM: porcine epidemic diarrhea virus

<400> SEQUENCE: 34
acttaaagag attttctatc tacggatagt tagctctttt tctagactct tgtctactca 60
attcaactaa acgaaatttt gtccttccgg ccgcatgtcc atgctgctgg aagctgacgt 120
ggaatttcat taggtttgct taagtagcca tcgcaagtgc tgtgctgtcc tctagttcct 180
ggttggcgtt ccgtcgcctt ctacatacta gacaaacagc cttcctccgg ttccgtctgg 240
gggttgtgtg gataactagt tctgtctagt ttgaaaccag taactgtcgg ctatggctag 300
caaccatgtt acattggctt ttgccaatga tgcagaaatt tcagcttttg gcttttgcac 360
tgctagtgaa gccgtctcat actattctga ggccgccgct agtggattta tgcaatgccg 420
tttcgtgtcc ttcgatctcg ctgacactgt tgagggattg cttcccgaag actatgtcat 480
ggtggtggtc ggcactacca agcttagtgc gtatgtggac acttttggta gccgccccaa 540
aaacatttgt ggttggctgt tattttctaa ctgtaattac ttcctcgaag agttagagct 600
tacttttggt cgtcgtggtg gtaacatcgt gccagttgac caatacatgt gtggcgctga 660
cggtaaacct gttcttcagg aatccgaatg ggagtataca gatttctttg ctgactccga 720
agacggtcaa ctcaacattg ctggtatcac ttatgtgaag gcctggattg tagagcgatc 780
ggatgtctct tatgcgagtc agaatttaac atctattaag tctattactt actgttcaac 840
ctatgagcat acttttcctg atggtactgc catgaaggtt gcacgtactc caaagattaa 900
gaagactgtt gtcttgtctg agccacttgc tactatctac agggaaattg gttctccttt 960

-continued

```
tgtggataat gggagcgatg ctcgttctat cattaagaga ccagtgttcc tccacgcttt   1020
tgttaagtgt aagtgtggta gttatcattg gactgttggt gattggactt cctatgtctc   1080
cacttgctgt ggctttaagt gtaagccagt ccttgtggct tcatgctctg ctacgcctgg   1140
ttctgttgtg gttacgcgcg ctggtgctgg cactggtgtt aagtattaca acaacatgtt   1200
cctgcgccat gtggcagaca ttgatgggtt ggcattctgg cgaattctca aggtgcagtc   1260
caaagacgac ctcgcttgct ctggtaaatt ccttgaacac catgaggaag gtttcacaga   1320
tccttgctac tttttgaatg actcgagcat tgctactaag ctcaagtttg acatccttag   1380
tggcaagttt tctgatgaag tcaaacaagc tatctttgct ggtcatgttg ttgttggcag   1440
cgcgctcgtt gacattgttg acgatgcact gggacagcct tggtttatac gtaagcttgg   1500
tgaccttgca agtgcagctt gggagcagct taaggctgtc gttagaggcc ttaacctcct   1560
gtctgatgag gtcgtgctct ttggcaaaag acttagctgt gccactctta gtatcgttaa   1620
cggtgttttt gagttcatcg ccgaagtgcc tgagaagttg gctgcggctg ttacagtttt   1680
tgtcaacttc ttgaatgagc tttttgagtc tgcctgtgac tgcttaaagg tcggaggtaa   1740
aacctttaac aaggttggct cttatgttct ttttgacaac gcattggtta agcttgtcaa   1800
ggcaaaagtt cgcggcccac gacaggcagg tgtttgtgaa gttcgttaca caagccttgt   1860
tattgggagt actaccaagg tggtttccaa gcgcgttgaa aatgccaatg tgaatctcgt   1920
cgtcgttgac gaggatgtga ccctcaacac cactggtcgt acagttgttg ttgacggact   1980
tgcattcttc gagagtgacg ggttttacag acatcttgct gatgctgacg ttgtcattga   2040
acatcctgtt tataagtctg cttgtgagct caagccagtt tttgagtgtg acccaatacc   2100
tgattttcct atgcctgtgg ccgctagtgt tgcagagctt tgtgtgcaaa ctgatctgtt   2160
gcttaaaaat tacaacactc cttataaaac ttacagctgc gttgtgagag gtgataagtg   2220
ttgtatcact tgcaccttac atttcacagc accaagttat atggaggctg ctgctaattt   2280
tgtagacctc tgtaccaaga acattggtac tgctggtttt catgagtttt acattacggc   2340
ccatgaacaa caggatctgc aagggttcgt aaccacttgt tgcacgatgt caggttttga   2400
gtgttttatg cctataatcc cacagtgtcc agcagtgctt gaagagattg atggtggtag   2460
catctggcgg tcttttatca ctggtcttaa tacaatgtgg gatttttgca agcatcttaa   2520
agtcagcttt ggactagatg gcattgttgt cactgtagca cgcaaattta aacgacttgg   2580
tgctctcttg gcagaaatgt ataacactta cctttcaact gtggtggaaa acttggtact   2640
ggccggtgtt agcttcaagt attatgccac cagtgtccca aaaattgttt tgggctgttg   2700
ttttcacagt gttaaaagtg ttcttgcaag tgccttccag attcctgtcc aggcaggcgt   2760
tgagaagttt aaagtcttcc ttaactgtgt tcaccctgtt gtaccacgtg tcattgaaac   2820
ttcttttgtg gaattagaag agacgacatt taaaccacca gcactcaatg gtagtattgc   2880
tattgttgat ggctttgctt tctattatga tggaacacta tactatccca ccgatggtaa   2940
tagcgttgtt cctatctgct ttaagaagaa aggtggtggt gatgtcaaat tctctgatga   3000
agtctctgtt aaaaccattg acccagttta taaggtctcc cttgaatttg agttcgagtc   3060
tgagactatt atggctgtgc ttaataaggc tgttggtaat tgtatcaagg ttacaggtgg   3120
ttgggacgat gttgttgagt atatcaatgt tgccattgag gttcttaaag atcacatcga   3180
tgtgcctaag tactacatct atgatgagga aggtggcacc gatcctaatc tgcccgtaat   3240
ggtttctcag tggccgttga atgatgacac gatctcacag gatctgcttg atgttgaagt   3300
tgttactgat gcgccagttg atttcgaggg tgatgaagta gactcctctg accctgataa   3360
```

```
ggtggcagac gtggctaact ctgagcctga ggatgacggt cttaatgtag ctcctgaaac   3420
aaatgtagag tctgaagttg aggaagttgc cgcaaccttg tcctttatta aagatacacc   3480
ttccacagtt actaaggatc cttttgcttt tgactttgca agctatggag gacttaaggt   3540
tttaagacaa tctcataaca actgctgggt tacttctacc ttggtgcagc tacaattgct   3600
tggcatcgtt gatgaccctg caatggagct tttagtgct ggtagagttg gtccaatggt   3660
tcgcaaatgc tatgagtcac aaaaggctat cttgggatct ttgggtgatg tgtcggcttg   3720
cctagagtct ctgactaagg acctacacac acttaagatt acctgttctg tagtctgtgg   3780
ttgtggtact ggtgaacgta tctatgatgg ttgtgctttt cgtatgacgc caactttgga   3840
accgttccca tatggtgctt gtgctcagtg tgctcaagtt ttgatgcaca cttttaaaag   3900
tattgttggc accggcatct tttgtcgaga tactactgct ctctccttgg attctttggt   3960
tgtaaaacct ctttgtgcgg ctgcttttat aggcaaggat agtggtcatt atgtcactaa   4020
cttttatgat gccgctatgg ctattgatgg ttatggtcgt catcagataa agtatgacac   4080
actgaacact atttgtgtta aagacgttaa ttggacagca ccttttgtcc cagacgttga   4140
gcctgtattg gagcttgttg tcaaaccttt ctattcttat aagaatgttg atttttacca   4200
aggagatttt agtgaccttg ttaaacttcc atgtgatttt gttgttaatg ctgcaaatga   4260
gaatttgtct cacggtggcg gcatagcaaa ggccattgat gtttatacca agggcatgtt   4320
gcagaagtgc tcgaatgatt acattaaagc acacggtccc attaaagttg gacgtggtgt   4380
catgttggag gcattaggtc ttaaggtctt taatgttgtt ggtccacgta agggtaagca   4440
tgcacctgag cttcttgtta aggcttataa gtccgttttt gctaattcag gtgttgctct   4500
tacacctttg attagtgttg gaatttttag tgttcctttg gaagaatctt tatctgcttt   4560
tcttgcatgt gttggtgatc gccactgtaa gtgcttttgt tatagtgaca aagagcgcga   4620
ggcgatcatt aattacatgg atggcttggt agatgctatt ttcaaagatg cacttgttga   4680
tactactcct gtccaggaag atgttcaaca agtttcacaa aaaccagttt tgcctaattt   4740
tgaacctttc aggattgaag gtgctcatgc tttctatgag tgcaaccctg aaggtttgat   4800
gtcattaggt gctgacaagc tggtgttgtt tacaaattcc aatttggatt tttgtagcgt   4860
tggtaagtgt cttaacaatg tgactggcgg tgcattgctt gaagccataa atgtatttaa   4920
aaagagtaac aaaacagtgc ctgctggcaa ctgtgttact tttgagtgtg cagatatgat   4980
ttctattact atggtagtat tgccatctga cggtgatgct aattatgaca aaaattatgc   5040
acgcgccgtc gtcaaggtat ctaagcttaa aggcaagtta ttgcttgctg ttggtgatgc   5100
catgttgtat tccaagttgt cccacctcag cgtgttaggt ttcgtatcca cacctgatga   5160
tgtggagcgt ttctacgcaa ataagagtgt ggttattaaa gttactgagg atacacgtag   5220
tgttaagact gttaaagtag aatccactgt tacttatgga caacaaattg gaccttgtct   5280
tgttaatgac accgttgtca cagacaacaa acctgttgtt gctgatgttg tagctaaggt   5340
tgtaccaagt gctaattggg attcacatta tggttttgat aaggctggtg agttccacat   5400
gctagaccat actgggtttg cctttcctag tgaagttgtt aacggtaggc gtgtgcttaa   5460
aaccacagat aataactgtt gggttaatgt tacatgttta caattacagt ttgctagatt   5520
taggttcaag tcagcaggtc tacaggctat gtgggagtcc tattgtactg gtgatgttgc   5580
tatgtttgtg cattggttgt actggcttac tggtgttgac aaaggtcagc ctagtgattc   5640
agaaaatgca cttaacatgt tgtctaagta cattgttcct gctggttctg tcactattga   5700
```

```
acgtgtcacg catgacggtt gttgttgtag taagcgtgtt gtcactgcac cagttgtgaa   5760
tgctagcgtg ttgaagcttg gcgtcgagga tggtctttgt ccacatggtc ttaactacat   5820
tgacaaagtt gttgtagtta aaggtactac aattgttgtc aatgttggaa aacctgtagt   5880
ggcaccatcg cacctctttc ttaagggtgt ttcctacaca acattcctag ataatggtaa   5940
cggtgttgcc ggccattata ctgtttttga tcatgacact ggtatggtgc atgatggaga   6000
tgtttttgta ccaggtgatc tcaatgtgtc tcctgttaca aatgttgtcg tctcagagca   6060
gacggctgtt gtgattaaag accctgtgaa gaaagtagag ttagacgcta caaagctgtt   6120
agacactatg aattatgcat cggaaagatt cttttccttt ggtgatttta tgtcacgtaa   6180
tttaattaca gtgtttttgt acatccttag tattttgggt ctctgtttta gggcctttcg   6240
taagagggat gttaaagttc tagctggtgt accccaacgt actggtatta tattgcgtaa   6300
aagtgtgcgc tataatgcaa aggctttggg tgtcttcttc aagctaaaac tttattggtt   6360
caaagttctt ggtaagttta gtttgggtat ttatgcattg tatgcattac tattcatgac   6420
aatacgcttt acacctatag gtggccctgt ttgtgatgat gttgttgctg gttatgctaa   6480
ttctagtttt gacaagaatg agtattgcaa cagtgttatt tgtaaggtct gtctctatgg   6540
gtaccaggaa ctttcggact tctctcacac acaggtagta tggcaacacc ttagagaccc   6600
attaattggt aatgtgatgc ctttctttta tttggcattt ctggcaattt ttggggggtgt   6660
ttatgtaaag gctattactc tctattttat tttccagtat cttaacatac ttggtgtgtt   6720
tttgggccta caacagtcca tttggttttt gcagcttgtg ccttttgatg tctttggtga   6780
cgagatcgtc gtctttttca tcgttacacg cgtattgatg ttccttaagc atgttttcct   6840
tggctgcgat aaggcatctt gtgtggcttg ctctaagagt gctcgcctta agcgcgttcc   6900
tgtccagact atttttcagg gtactagcaa atccttctac gtacatgcca atggtggttc   6960
taagttctgt aagaagcaca atttcttttg tttaaattgt gattcttatg gtccaggctg   7020
cacttttatt aatgacgtca ttgcaactga agttggtaat gttgtcaaac ttaatgtgca   7080
accgacaggt cctgccacta ttcttattga caaggttgaa ttcagtaatg gtttttacta   7140
tctttatagt ggtgacacat tttggaagta caactttgac ataacagata acaaatacac   7200
ttgcaaagag tcacttaaaa attgtagcat aatcacagac tttattgttt ttaacaataa   7260
tggttccaat gtaaatcagg ttaagaatgc atgtgtgtat tttcacaga tgctttgtaa   7320
acctgttaag ttagtggact cagcgttgtt ggccagtttg tctgttgatt ttggtgcaag   7380
cttacatagt gcttttgtta gtgtgttgtc gaatagtttt ggcaaagacc tgtcaagttg   7440
taatgacatg caggattgca agagcacatt gggttttgat gatgtaccat tggatacctt   7500
taatgctgct gttgctgagg ctcatcgtta cgatgtcctc ttgactgaca tgtcgttcaa   7560
caattttacc accagttatg caaaaccaga ggaaaaactt cccgtccatg acattgccac   7620
gtgtatgcgt gtaggtgcca agattgttaa tcataacgtt cttgtcaagg atagtatacc   7680
tgtggtgtgg cttgtacgtg atttcattgc cctttctgaa gaaactagga agtacattat   7740
tcgtacgact aaagttaagg gtataacctt catgttgacc tttaatgatt gtcgtatgca   7800
tactaccata cctactgttt gcattgcaaa taagaagggt gcaggtcttc ctagtttttc   7860
aaaggttaag aaattcttct ggtttttgtg tctgttcata gttgctgttt tctttgcact   7920
aagctttttt gattttagta ctcaggttag cagtgatagt gattatgact tcaagtatat   7980
tgagagtggc cagttgaaga cttttgacaa tccacttagt tgtgtgcata atgtctttag   8040
taacttcgac cagtggcatg atgccaagtt tggtttcacc cccgtcaaca atcctagttg   8100
```

```
tcctatagtc gttggtgtat cagacgaagc gcgcactgtt ccaggtatcc cagcaggtgt   8160
ttatttagct ggtaaaacac ttgtttttgc tattaacacc atttttggta catctggttt   8220
gtgctttgat gctagtggcg ttgctgataa gggcgcttgc atttttaatt cggcttgcac   8280
cacattatct ggtttgggtg gaactgctgt ctactgttat aagaatggtc tagttgaagg   8340
tgctaaactt tatagtgagt tggcacctca tagctactat aaaatggtag atggtaatgc   8400
tgtgtcttta cctgaaatta tctcacgcgg ctttggcatc cgtactatcc gtacaaaggc   8460
tatgacctac tgtcgcgttg gccagtgtgt gcaatctgca gaaggtgttt gttttggcgc   8520
cgatagattc tttgtctata atgcagaatc tggttctgac tttgtttgtg gcacagggct   8580
ctttacattg ttgatgaacg ttattagtgt tttttccaag acagtaccag taactgtgtt   8640
gtctggtcaa atacttttta attgcattat tgcttttgct gctgttgcgg tgtgtttctt   8700
atttacaaag tttaagcgca tgttcggtga tatgtctgtt ggcgttttca ctgtcggtgc   8760
ttgtactttg ttgaacaatg tttcctacat tgtaacacag aacacacttg gcatgttggg   8820
ctatgcaact ttgtactttt tgtgcactaa aggtgttaga tatatgtgga tttggcattt   8880
gggatttttg atctcatata tacttattgc accatggtgg gttttgatgg tttatgcctt   8940
ttcagccatt tttgagttta tgcctaacct ttttaagctt aaggtttcaa cacaactttt   9000
tgagggtgac aagttcgtag gctcttttga aaatgctgca gcaggtacat ttgtgcttga   9060
tatgcatgcc tatgagagac ttgccaactc tatctcaact gaaaaactgc gtcagtatgc   9120
tagtacttac aataagtaca agtattattc aggcagtgct tcagaggctg attacaggct   9180
tgcttgtttt gcccatttgg ccaaggctat gatggattat gcttctaatc acaacgacac   9240
gttatacaca ccacccactg tgagttacaa ttcaactcta caggctggct tgcgtaagat   9300
ggcacaacca tctggtgttg ttgagaagtg catagttcgt gtttgctatg gtaatatggc   9360
tcttaatggc ctatggcttg gtgatactgt tatctgccca cgccatgtta tagcgtctag   9420
tactactagc actatagatt atgactatgc cctttctgtt ttacgcctcc acaacttctc   9480
catttcatct ggtaatgttt tcctaggtgt tgtgggtgta accatgcgag gtgctttgtt   9540
gcagataaag gttaatcaaa acaatgtcca cacgcctaag tacacctatc gcacagttag   9600
accgggtgaa tcttttaata tcttggcgtg ctatgatggt tctgcagctg gtgtttacgg   9660
cgttaacatg cgctctaatt acactattag aggctcgttc attaatggcg cttgtggttc   9720
acctggttat aacattaaca atggtaccgt tgagttttgc tatttacacc agcttgaact   9780
tggttcaggc tgtcatgttg gtagcgactt agatggtgtt atgtatggtg gttatgagga   9840
ccaacctact ttgcaagttg aaggcgctag tagtctgttt acagagaatg tgttggcatt   9900
tctttatgca gcactcatta atggttctac ctggtggctt agttcttcta ggattgctgt   9960
agacaggttt aatgagtggg ctgttcataa tggtatgaca acagtagtta atactgattg  10020
cttttctatt cttgctgcta agactggtgt tgatgtacaa cgtttgttgg cctcaatcca  10080
gtctctgcat aagaattttg gtggaaagca aattcttggc tatacctcgt tgacagatga  10140
gtttactaca ggtgaagtta tacgtcaaat gtatggcgtt aatcttcaga gtggttatgt  10200
ttcacgcgcc tgtagaaatg tcttgctggt tggttctttt ctgactttct tttggtcaga  10260
attagtttcc tacactaagt tcttttgggt aaatcctggt tatgtcacac ctatgtttgc  10320
gtgtttgtca ttgctgtcct cacttttgat gttcacactc aagcataaga cattgttttt  10380
ccaggtcttt ctaatacctg ctctgattgt tacatcttgc attaatttgg catttgatgt  10440
```

-continued

```
tgaagtctac aactatttgg cagagcattt tgattaccat gtttctctca tgggttttaa  10500
tgcacaaggt cttgttaaca tctttgtctg ctttgttgtt accattttac acggcacata  10560
cacatggcgc ttttttaaca cacctgtgag ttctgtcact tatgtggtag ctttgctgac  10620
tgcggcatat aactattttt acgctagtga cattcttagt tgtgctatga cactatttgc  10680
tagtgtgact ggcaactggt tcgttggtgc tgtttgttat aaagctgctg tttatatggc  10740
cttgagattt cctacttttg tggctatttt tggtgatatt aagagtgtta tgttctgtta  10800
ccttgtgttg ggttatttta cctgttgctt ctacggtatt ctctactggt tcaacaggtt  10860
ttttaaggtt agtgtaggtg tctatgacta tactgttagt gctgctgagt ttaagtatat  10920
ggttgctaac ggcctacgtg caccaactgg aacacttgat tcactacttc tgtctgccaa  10980
attgattggt attggtggtg agcggaatat taagatttct tccgttcagt ctaaactgac  11040
tgatattaag tgtagtaacg ttgtgctttt aggctgtctc tctagcatga atgtctcagc  11100
aaattcaaca gaatgggcct attgtgttga cttgcataac aagatcaact tgtgtaatga  11160
cccagaaaaa gcgcaggaaa tgctacttgc tttgttggca tttttcctta gtaagaatag  11220
tgcttttggt ttagatgact tattggaatc ctattttaat gacaatagta tgttgcagag  11280
tgttgcatct acttatgtcg gtttgccttc ttatgtcatt tatgaaaatg cacgccaaca  11340
gtatgaagat gctgttaata atggttctcc acctcagttg gttaagcaat tgcgccatgc  11400
catgaatgta gcaaagagcg aatttgaccg tgaggcttct actcagcgta agcttgatag  11460
aatggcggaa caggctgcag cacagatgta caaagaggca cgagcagtta ataggaagtc  11520
caaagttgta agtgctatgc attcactgct tttggtatg ttgagacgtt tggacatgtc  11580
ttctgtagac accattctca acttggcaaa ggatggggtt gtacctctgt ctgtcatacc  11640
ggcagtcagt gctactaagc ttaacattgt tacttctgat atcgattctt ataatcgtat  11700
ccagcgtgag ggatgtgtcc actacgctgg taccatttgg aatataattg atatcaagga  11760
caatgatggc aaggtggtac acgttaagga ggtaaccgca cagaatgctg agtccctgtc  11820
atggcccctg gtccttgggt gtgagcgtat tgtcaagctc cagaataatg aaattattcc  11880
cggtaagctg aagcagcgct ccattaaggc agaaggagat ggcatagttg gagaaggtaa  11940
ggcactttac aataatgagg gtggacgtac ttttatgtat gctttcatct cggacaaacc  12000
ggacctgcgt gtagtcaagt gggagttcga tggtggttgt aacactattg agctagaacc  12060
accacgtaag ttcttggtgg attctcctaa tggtgcacag atcaagtatc tctactttgt  12120
tcgtaacctt aacacgttac gtaggggtgc tgttctcggc tacataggtg ccactgtacg  12180
cttgcaggct ggtaaacaaa cagaacaggc tattaactct tcattgttga cactttgcgc  12240
tttcgctgtg gatcctgcta agacctacat cgatgctgtc aaaagtggtc acaaaccagt  12300
aggtaactgt gttaagatgt tggccaatgg ttctggtaat ggacaagctg ttactaatgg  12360
tgtggaggct agtactaacc aggattcata cggtggtgcg tccgtgtgtc tatattgtag  12420
agcacatgtt gagcatccat ctatggatgg tttttgcaga ctgaaaggca agtacgtaca  12480
ggttccacta ggtacagtgg atcctatacg ttttgtactt gagaatgacg tttgcaaggt  12540
ttgtggttgt tggctggcta atggctgcac ttgtgacaga tccattatgc aaagcactga  12600
tatggcttat ttaaacgagt acggggctct agtgcagctc gactagagcc ctgtaacggt  12660
actgatacac aacatgtgta tcgtgctttt gacatctaca acaaggatgt tgcttgtcta  12720
ggtaaattcc tcaaggtgaa ctgtgttcgc ctgaagaatt tggataagca tgatgcattc  12780
tatgttgtca aaagatgtac caagtctgcg atggaacacg agcaatccat ctatagcaga  12840
```

```
cttgaaaagt gtggagccgt agccgaacac gatttcttca cttggaagga tggtcgtgcc  12900
atctatggta acgtttgtag aaaggatctt accgagtata ctatgatgga tttgtgttac  12960
gctttacgta actttgatga aaacaattgc gatgttctta agagcatttt aattaaggta  13020
ggcgcttgtg aggagtccta cttcaataat aaagtctggt ttgaccctgt tgaaaatgaa  13080
gacattcatc gtgtctatgc attgttaggt accattgttt cacgtgctat gcttaaatgc  13140
gttaagttct gtgatgcaat ggttgaacaa ggtatagttg gtgttgtcac attagataat  13200
caggatctta atggtgattt ttatgatttt ggtgatttta cttgtagcat caagggaatg  13260
ggtataccca tttgcacatc atattactct tatatgatgc ctgttatggg tatgactaat  13320
tgccttgcta gtgagtgttt tgttaagagt gatatatttg gtgaggattt caagtcatat  13380
gacctgctgg aatatgattt cacggagcat aagacagcac tcttcaacaa gtatttcaag  13440
tattggggac tgcaatacca ccctaattgt gtggactgca gtgatgagca gtgcatagtt  13500
cactgtgcca acttcaatac gttgttttcc actactatac ctattacggc atttggacct  13560
ttgtgtcgca agtgttggat tgatggtgtt ccactggtaa ttacagctgg ttatcatttt  13620
aaacagttag gtatagtttg gaacaatgac ctcaacttac actctagcag gctctctatt  13680
aacgaattac tccagttttg tagtgatcct gcattgctta tagcatcatc accagccctt  13740
gttgatcagc gtactgtttg cttttcagtt gcagcgctag gtacaggtat gactaaccag  13800
actgttaaac ctggccattt caataaggag ttttatgact tcttacttga gcaaggtttc  13860
ttttctgagg gctctgagct tactttaaag cacttcttct ttgcacagaa gggtgatgca  13920
gctgttaagg attttgacta ctataggtat aatagaccta ctgttctgga catttgccaa  13980
gctcgcgtcg tgtatcaaat agtgcaacgc tattttgata tttacgaagg tggttgtatc  14040
actgctaaag aggtggttgt tacaaacctt aacaagagcg caggttatcc tttgaacaag  14100
tttggtaaag ctggtcttta ctatgagtct ttatcctatg aggaacagga tgaactttat  14160
gcttatacta agcgtaacat cctgcccact atgacacagc tcaaccttaa atatgctata  14220
agtggcaaag aacgtgcacg cacagtgggt ggtgtttcgc ttttgtcaac catgactact  14280
cggcagtatc atcagaaaca ccttaagtcc atagttaata ctaggggcgc ttcggttgtt  14340
attggtacta ctaagtttta tggtggttgg gacaatatgc ttaagaacct tattgatggt  14400
gttgaaaatc cgtgtcttat gggttgggac tacccaaagt gcgacagagc actgcccaat  14460
atgatacgta tgatttcagc catgatttta ggctctaagc acaccacatg ctgcagttcc  14520
actgaccgct tttcaggtt gtgcaatgaa ttggctcaag tccttactga ggttgtttat  14580
tctaatggag gtttttattt gaagccaggt ggtactacct ctggtgatgc aaccaccgca  14640
tatgcaaact cagtttttaa tatcttccaa gcagtaagtg ccaatgttaa caaacttctt  14700
agtgttgaca gcaatgtctg tcataattta gaagttaagc aattgcagcg taagctttat  14760
gagtgctgtt atagatcaac taccgtcgat gaccagttcg tcgttgagta ttatggttac  14820
ttgcgtaaac atttttcaat gatgattctt tctgatgatg gcgttgtttg ttataacaat  14880
gactatgcat cacttggtta tgtcgctgat cttaacgcct tcaaggctgt tttgtattac  14940
cagaacaatg tcttcatgag cgcctctaaa tgttggatcg agcctgacat taataaaggt  15000
cctcatgaat tttgctcgca gcatactatg cagattgtcg ataaagatgg tacttattac  15060
cttccttacc ctgatccttc aagaattctc tctgcaggtg tgtttgttga tgacgttgtt  15120
aaaactgatg cagttgtatt gcttgaacgt tatgtgtcat tggctataga tgcctacccg  15180
```

-continued

```
ttatctaagc atgaaaaccc tgaatataag aaggtgtttt atgtgctttt ggattgggtt  15240
aagcatctgt acaaaactct taatgctggt gtgttagagt ctttttctgt cacacttttg  15300
gaagattcta ctgctaaatt ctgggatgag agcttttatg ccaacatgta tgagaaatct  15360
gcagttttac aatctgcagg gctttgtgtt gtttgtggct ctcaaactgt tttacgttgt  15420
ggtgattgtc tacggcgtcc tatgctttgt actaagtgtg cttatgatca tgtcattgga  15480
acaactcaca agttcatttt ggccatcact ccatatgtgt gttgtgcttc agattgtggt  15540
gtcaatgatg taactaagct ctacttaggt ggtcttagtt attggtgtca tgaccacaag  15600
ccacgtcttg cattcccgtt gtgctctgct ggtaatgttt ttggcttgta caaaaattct  15660
gctaccggct cacccgatgt tgaagacttt aatcgcattg ctacatccga ttggactgat  15720
gtttctgact acaggttggc aaatgatgtc aaggactcat tgcgtctgtt tgcagcggaa  15780
actatcaagg ccaaggagga gagcgttaag tcatcctatg cttgtgcaac actacatgag  15840
gttgtaggac ctaaagagtt gttgctcaaa tgggaagtcg gcagacccaa accacccctt  15900
aatagaaatt cggttttcac ttgttatcat ataacgaaga acaccaaatt tcaaatcggt  15960
gagtttgtgt ttgagaaggc agaatatgat aatgatgctg taacatataa aactaccgcc  16020
acaacaaaac ttgttcctgg catggttttt gtgcttacct cacataatgt tcagccattg  16080
cgcgcaccga ccattgctaa tcaagaacgt tattccacta tacataagtt gcatcctgct  16140
tttaacatac ctgaagctta ttctagctta gtgccctatt accaattgat tggtaagcag  16200
aagattacaa ctattcaggg acctcccggt agtggtaaat ctcactgtgt tatagggcta  16260
ggtttgtact atccaggtgc acgtatagtg tttacagctt gttctcatgc agcggtcgat  16320
tcactttgtg tgaaagcttc cactgcttat agcaatgaca aatgttcacg catcatacca  16380
cagcgcgctc gtgttgagtg ttatgatggt ttcaagtcta ataatactag tgctcagtac  16440
cttttctcta ctgtcaatgc tttgccagag tgcaatgcgg acattgttgt ggtggatgag  16500
gtctctatgt gcactaatta tgacttgtct gtcataaatc agcgcatcag ctataggcat  16560
gtagtctatg ttggtgaccc tcaacagctg cctgcaccac gtgttatgat ttcacgtggt  16620
actttggaac caaaggacta caacgttgtc actcaacgca tgtgtgccct taagcctgat  16680
gttttcttgc acaagtgtta tcgctgtcct gctgagatag tgcgtactgt gtctgagatg  16740
gtctatgaaa accaattcat tcctgtgcac ccagatagca agcagtgttt taaaatcttt  16800
tgcaagggta atgttcaggt tgataatggt tcaagcatta atcgcaggca attggatgtt  16860
gtgcgtatgt ttttggctaa aaatcctagg tggtcaaagg ctgtttttat ttctccttat  16920
aacagccaga attatgttgc cagccgcatg ctaggtctac aaattcagac agttgactca  16980
tcccagggta gtgagtatga ctatgtcatt tacacacaaa cttcagatac tgcccatgcc  17040
tgtaatgtta acaggtttaa tgttgccatc acaagggcca agaaaggcat attatgtata  17100
atgtgcgata ggtccctttt tgatgtgctt aaattctttg agcttaaatt gtctgatttg  17160
caggctaatg agggttgtgg tctttttaaa gactgtagca gaggtgatga tctgttgcca  17220
ccatctcacg ctaacacctt catgtcttta gcggacaatt ttaagactga tcaagatctt  17280
gctgttcaaa taggtgttaa tggacccatt aaatatgagc atgttatctc gtttatgggt  17340
ttccgttttg atatcaacat acccaaccat catactctct tttgcacacg cgactttgcc  17400
atgcgcaatg ttagaggttg gttaggcttt gacgttgaag gagcacatgt tgttggctct  17460
aacgtcggta caaatgtccc attgcaatta gggttttcta acggtgttga ttttgttgtc  17520
agacctgaag gttgcgttgt aacagagtct ggtgactaca ttaaacccgt cagagctcgt  17580
```

```
gctccaccag gggaacaatt cgcacacctt ttgcctttac ttaaacgcgg ccaaccatgg  17640
gatgttgtcc gcaaacgtat agtgcagatg tgtagtgact acctggccaa cctatcagac  17700
atactaattt ttgtgttgtg ggctggtggt ttggagttga caactatgcg ttattttgtc  17760
aagattggac caagtaagag ttgtgattgt ggtaaggttg ctacttgtta caatagtgcg  17820
ctgcatacgt actgttgttt caaacatgcc cttggttgtg attatctgta taacccatac  17880
tgtattgata tacagcagtg gggatacaag ggatcactta gccttaacca ccatgagcat  17940
tgtaatgtac atagaaacga gcatgtggct tctggtgatg ccataatgac tcgctgtctg  18000
gccatacatg attgctttgt caagaacgtt gactggtcca tcacataccc atttattggt  18060
aatgaggctg ttattaataa gagcggccga attgtgcaat cacacactat gcggtcagtt  18120
cttaagttat acaatccgaa agccatatat gatattggca atcctaaggg cattagatgt  18180
gccgtaacgg atgctaagtg gttttgcttt gacaagaatc ctactaattc taatgtcaag  18240
acattggagt atgactatat aacacatggc caatttgatg ggttgtgctt gttttggaat  18300
tgcaatgtag acatgtatcc agaattttct gtggtctgtc gttttgatac tcgctgtagg  18360
tcaccactca acttggaggg ttgtaatggt ggttcactgt atgttaataa tcatgcattc  18420
catacaccgg cttttgacaa gcgtgctttt gctaagttga agccaatgcc atttttcttt  18480
tatgatgata ctgagtgtga caagttacag gactccataa actatgttcc tcttagggct  18540
agtaactgca ttactaaatg taatgttggt ggtgctgtct gtagtaagca ttgtgctatg  18600
tatcatagct atgttaatgc ttacaacact tttacgtcgg cgggctttac tatttgggtg  18660
cctacttcgt ttgacaccta taatctgtgg cagacattta gtaacaattt gcaaggtctt  18720
gagaacattg ctttcaatgt cgtaaagaaa ggatcttttg ttggtgccga aggtgaactt  18780
cctgtagctg tggttaatga caaagtgctc gttagagatg gtactgttga tactcttgtt  18840
tttacaaaca agacatcact acccactaac gtagcttttg agttgtatgc caagcgtaag  18900
gtaggactca ccccacccat tacgatccta cgtaacttgg gtgtagtttg tacatctaag  18960
tgtgtcattt gggactatga agccgaacgt ccacttacta cttttacaaa ggatgtttgt  19020
aaatataccg actttgaggg tgacgtctgt acactctttg ataacagcat tgttggttca  19080
ttagagcgat tctccatgac ccaaaatgct gtgcttatgt cacttacagc tgttaaaaag  19140
cttactggca taaagttaac ttatggttat cttaatggtg tcccagttaa cacacatgaa  19200
gataaacctt ttacttggta tatttacact aggaagaacg gcaagttcga ggaccatcct  19260
gatggctatt ttacccaagg tagaacaacc gctgatttta gccctcgtag cgacatggaa  19320
aaggacttcc taagtatgga tatgggtctg tttattaaca agtacggact tgaggattac  19380
ggctttgagc acgttgtgta tggtgatgtt tcaaaaacca cccttggtgg tttgcatcta  19440
ctaatttcgc aggtgcgtct ggcctgtatg ggtgtgctca aaatagacga gtttgtgtct  19500
agtaatgata gcacgttaaa gtcttgtact gttacatatg ctgataaccc tagtagtaag  19560
atggtttgta cgtatatgga tctcctgctt gacgattttg tcagcattct taaatctttg  19620
gatttgggcg ttgtatctaa agttcatgaa gttatggtcg attgtaaaat gtggaggtgg  19680
atgttgtggt gtaaggatca taaactccag acattttatc cgcaacttca ggccagtgaa  19740
tggaagtgtg gttattccat gccttctatt tacaagatac aacgtatgtg tttagaacct  19800
tgcaatctct acaactatgg tgctggtatt aagttacctg atggcattat gtttaacgta  19860
gttaaataca cacagctttg tcaatatctc aatagcacca caatgtgtgt accccatcac  19920
```

```
atgcgtgtgc tacatcttgg tgctggctcc gacaagggtg ttgcacctgg cacggctgtc  19980
ttacgacgtt ggttgccact ggatgccatt atagttgaca atgatagtgt ggattacgtt  20040
agcgatgctg attatagtgt tacaggagat tgctctacct tatacctgtc agataagttt  20100
gatttagtta tatctgatat gtatgatggt aagattaaaa gttgtgatgg ggagaacgtg  20160
tctaaagaag gcttctttcc ctatattaat ggtgtcatca ccgaaaagtt ggcacttggt  20220
ggtactgtag ctattaaggt gacggagttt agttggaata agaagttgta tgaactcatt  20280
cagaggtttg agtattggac aatgttctgt accagtgtta acacgtcatc gtcagaggca  20340
ttcttaattg gtgttcacta tttaggtgat tttgcaagtg gcgctgtgat tgacggcaac  20400
actatgcatg ccaattatat cttctggcgt aattccacaa ttatgactat gtcttacaat  20460
agtgtacttg atttaagcaa gttcaattgt aagcataagg ctacagttgt cattaattta  20520
aaagattcat ccattagtga tgttgtgtta ggtttgttga agaatggtaa gttgctagtg  20580
cgtaataatg acgccatttg tggtttttct aatcatttgg tcaacgtaaa caaatgaagt  20640
ctttaaccta cttctggttg ttcttaccag tactttcaac acttagccta ccacaagatg  20700
tcaccaggtg ctcagctaac actaatttta ggcggttctt ttcaaaattt aatgttcagg  20760
cgcctgcagt tgttgtactg ggcggttatc tacctattgg tgaaaaccag ggtgtcaatt  20820
caacttggta ctgtgctggc caacatccaa ctgctagtgg cgttcatggt atctttgtta  20880
gccatattag aggtggtcat ggctttgaga ttggcatttc gcaagagcct tttgacccta  20940
gtggttacca gctttattta cataaggcta ctaacggtaa cactaatgct actgcgcgac  21000
tgcgcatttg ccagtttcct agcattaaaa cattgggccc cactgctaat aatgatgtta  21060
caacaggtcg taattgccta tttaacaaag ccatcccagc tcatatgagt gaacatagtg  21120
ttgtcggcat aacatgggat aatgatcgtg tcactgtctt ttctgacaag atctattatt  21180
tttattttaa aaatgattgg tcccgtgttg cgacaaagtg ttacaacagt ggaggttgtg  21240
ctatgcaata tgtttacgaa cccacctatt acatgcttaa tgttactagt gctggtgagg  21300
atggtatttc ttatcaaccc tgtacagcta attgcattgg ttatgctgcc aatgtatttg  21360
ctactgagcc caatggccac ataccagaag gttttagttt taataattgg tttcttttgt  21420
ccaatgattc cactttggtg catggtaagg tggtttccaa ccaaccattg ttggtcaatt  21480
gtcttttggc cattcctaag atttatggac taggccaatt tttctccttt aatcaaacga  21540
tcgatggtgt ttgtaatgga gctgctgtgc agcgtgcccc agaggctctg aggtttaata  21600
ttaatgacat ctctgtcatt cttgctgaag gctcaattgt acttcatact gctttaggaa  21660
caaatttttc ttttgtttgc agtaattcct caaatcctca cttagccacc ttcgccatac  21720
ctctgggtgc tacccaagta ccttattatt gtttttttaa agtggatact tacaactcca  21780
ctgtttataa atttttggct gttttacctc ctaccgtcag ggaaattgtc atcaccaagt  21840
atggtgatgt ttatgtcaat gggtttggat acttgcatct cggtttgttg gatgctgtca  21900
caattaattt cactggtcat ggcactgacg atgatgtttc tggtttttgg accatagcat  21960
cgactaattt tgttgatgca ctcatcgaag ttcaaggaac cgccattcag cgtattcttt  22020
attgtgatgg gcatcctgtt agccaactca agtgttctca ggttgctttt gaccttgacg  22080
atggttttta cactatttct tctagaaacc ttctgagtca tgaacagcca atttcttttg  22140
ttactctgcc atcatttaat gatcattctt ttgttaacat tactgtatct gcttcctttg  22200
gtggtcatag tggtgccaac cttattgcat ctgacactac tatcaatggg tttagttctt  22260
tctgtgttga cactagacaa tttaccattt cactgtttta taacgttaca aacagttatg  22320
```

```
gttatgtgtc taaatcacag gacagtaatt gccctttcac cttgcaatct gttaatgatt  22380
acctgtcttt tagcaaattt tgtgtttcca ccagcctttt ggctagtgcc tgtaccatag  22440
atctttttgg ttaccctgag tttggtagtg gtgttaagtt tacgtccctt tactttcaat  22500
tcacaaaggg tgagttgatt actggcacgc ctaaaccact tgaaggtgtc acggacgttt  22560
cttttatgac tctggatgtg tgtaccaagt atactatcta tggctttaaa ggtgagggta  22620
tcattaccct tacaaattct agctttttgg caggtgttta ttacacatct gattctggac  22680
agttgttagc ctttaagaat gtcactagtg gtgctgttta ttctgttacg ccatgttctt  22740
tttcagagca ggctgcatat gttgatgatg atatagtggg tgttatttct agtttgtcta  22800
gctccacttt taacagtact agggagttgc ctggtttctt ctaccattct aatgatggct  22860
ctaattgtac agagcctgtg ttggtgtata gtaacatagg tgtttgtaaa tctggcagta  22920
ttggctacgt cccatctcag tctggccaag tcaagattgc acccacggtt actgggaata  22980
ttagtattcc caccaacttt agtatgagta ttaggacaga atatttacag ctttacaaca  23040
cgcctgttag tgttgattgt gccacatatg tttgtaatgg taactctcgt tgtaaacaat  23100
tactcaccca gtacactgca gcatgtaaga ccatagagtc agcattacaa ctcagcgcta  23160
ggcttgagtc tgttgaagtt aactctatgc ttactatttc tgatgaggct ctacagttag  23220
ctaccattag ttcgtttaat ggtgatggat ataattttac taatgtgctg ggtgtttctg  23280
tgtatgatcc tgcaagtggc agggtggtaa agaagaggtc ttttattgaa gacctgcttt  23340
ttaataaagt ggttactaat ggccttggta ctgttgatga agactataag cgctgttcta  23400
atggtcgctc tgtggcagat ctagtctgtg cacagtatta ctctggtgtc atggtactac  23460
ctggtgttgt tgacgctgag aagcttcaca tgtatagtgc gtctctcatc ggtggtatgg  23520
tgctaggagg ttttacttct gcagcggcat tgccttttag ctatgctgtt caagctagac  23580
tcaattatct tgctctacag acggatgttc tacagcggaa ccagcaattg cttgctgagt  23640
cttttaactc tgctattggt aatataactt cagcctttga gagtgttaaa gaggctatta  23700
gtcaaacttc caagggtttg aacactgtgg ctcatgcgct tactaaggtt caagaggttg  23760
ttaactcgca gggtgcagct ttgactcaac ttaccgtaca gctgcaacac aacttccaag  23820
ccatttctag ttctattgat gacatttact ctcgactgga cattctttca gccgatgctc  23880
aggttgaccg tctcatcacc ggcagattat cagcacttaa tgcttttgtt gctcaaaccc  23940
tcactaagta tactgaggtt caggctagca ggaagttagc acagcaaaag gttaatgagt  24000
gcgttaaatc gcaatctcag cgttatggtt tttgtggtgg tgatggcgag cacattttct  24060
ctctggtaca ggcagcacct cagggcctgc tgtttttaca tacagtactt gtaccgagtg  24120
attttgtaga tgttattgcc atcgctggct tatgcgttaa cgatgaaatt gccttgactc  24180
tacgtgagcc tggcttagtc ttgtttacgc atgaacttca aaatcatact gcgacggaat  24240
attttgtttc atcgcgacgt atgtttgaac ctagaaaacc taccgttagt gattttgttc  24300
aaattgagag ttgtgtggtc acctatgtca atttgactag agaccaacta ccagatgtaa  24360
tcccagatta catcgatgtt aacaaaacac tttatgagat tttagcttct ctgcccaata  24420
gaactggtcc aagtcttcct ttagatgttt ttaatgccac ttatcttaat ctcactggtg  24480
aaattgcaga tttagagcag cgttcagagt ctctccgtaa tactacagag gagctccaaa  24540
gtcttatata taatatcaac aacacactag ttgaccttga gtggctcaac cgagttgaga  24600
catatatcaa gtggccgtgg tgggtttggt tgattatttt cattgttctc atctttgttg  24660
```

-continued

```
tgtcattact agtgttctgc tgcatttcca cgggttgttg tggatgctgc ggctgctgct  24720
gtgcttgttt ctcaggttgt tgtaggggtc ctagacttca accttacgaa gtttttgaaa  24780
aggtccacgt gcagtgatgt ttcttggact ttttcaatac acgattgaca cagttgtcaa  24840
agatgtctca aagtctgcta acttgtcttt ggatgctgtc caagagttgg agctcaatgt  24900
agttccaatt agacaagctt caaatgtgac gggttttctt ttcaccagtg tttttatcta  24960
cttctttgca ctgtttaaag cgtcttcttt gaggcgcaat tatattatgt tggcagcgcg  25020
ttttgctgtc attgttcttt attgcccact tttatattat tgtggtgcat ttttagatgc  25080
aactattatt tgttgcacac ttattggcag gctttgttta gtctgctttt actcctggcg  25140
ctataaaaat gcgctcttta ttatttttaa tactacgaca ctttctttcc tcaatggtaa  25200
agcagcttat tatgacggca aatccattgt gattttagaa ggtggtgacc attacatcac  25260
ttttggcaac tcttttgttg cttttgttag tagcatcgac ttgtatctag ctatacgtgg  25320
gcggcaagaa gctgacctac agctgttgcg aactgttgag cttcttgatg gcaagaagct  25380
ttatgtcttt tcgcaacatc aaattgttgg cattactaat gctgcatttg actcaattca  25440
actagacgag tatgctacaa ttagtgaatg ataatggtct agtagttaat gttatacttt  25500
ggcttttcgt actctttttc ctgcttatta taagcattac tttcgtccaa ttggttaatc  25560
tgtgcttcac ttgtcaccgg ttgtgtaata gcgcagttta cacacctata gggcgtttgt  25620
atagagttta taagtcttac atgcaaatag acccccctcct tagtactgtt attgacgtat  25680
aaacgaaata tgtctaacgg ttctattccc gttgatgagg tgattcaaca ccttagaaac  25740
tggaatttca catggaatat catactgacg atactacttg tagtgcttca gtatggccat  25800
tacaagtact ctgcgttctt gtatggtgtc aagatggcta ttctatggat actttggcct  25860
cttgtgttag cactgtcact tttgatgca tgggctagct ttcaggtcaa ttgggtcttt  25920
tttgctttca gcatccttat ggcttgcatc actcttatgc tgtggataat gtactttgtc  25980
aatagcattc ggttgtggcg caggacacat tcttggtggt ctttcaatcc tgaaacagac  26040
gcgcttctca ctacttctgt gatgggccga caggtctgca ttccagtgct tggagcacca  26100
actggtgtaa cgctaacact ccttagtggt acattgcttg tagagggcta taaggttgct  26160
actggcgtac aggtaagtca attacctaat ttcgtcacag tcgccaaggc cactacaaca  26220
attgtctacg gacgtgttgg tcgttcagtc aatgcttcat ctggcactgg ttgggctttc  26280
tatgtccggt ccaaacacgg cgactactca gctgtgagta atccgagttc ggttctcaca  26340
gatagtgaga aagtgcttca tttagtctaa acagaaactt tatggcttct gtcagttttc  26400
aggatcgtgg ccgcaaacgg gtgccattat ccctctatgc ccctcttagg gttactaatg  26460
acaaacccct ttctaaggta cttgcaaata atgctgtacc cactaataaa ggaaataagg  26520
accagcaaat tggatactgg aatgagcaaa ttcgctggcg catgcgccgt ggtgagcgaa  26580
ttgaacaacc ttccaattgg catttctact acctcggaac aggacctcac gccgacctcc  26640
gctataggac tcgtactgag ggtgttttct gggttgctaa agaaggcgca aagactgaac  26700
ccactaacct gggtgtcaga aaggcgtctg aaaagccaat tattccaaat ttctctcaac  26760
agcttcccag cgtagttgag attgttgaac ctaacacacc tcctacttca cgtgcaaatt  26820
cacgtagcag gagtcgtggt aatggcaaca acaggtccag atctccaagt aacaacagag  26880
gcaataacca gtcccgcggt aattcacaga atcgtggaaa taaccagggt cgtggagctt  26940
ctcagaacag aggaggcaat aataataaca ataacaagtc tcgtaaccag tccaagaaca  27000
gaaaccagtc aaatgaccgt ggtggtgtaa catcacgcga tgatctggtg gctgctgtca  27060
```

```
aggatgccct taaatctttg ggtattggcg aaaaccctga caagcttaag caacagcaga  27120
agcccaaaca ggaaaggtct gacagcagcg gcaaaaatac acctaagaag aacaaatcca  27180
gagccacttc gaaagaacgt gacctcaaag acatcccaga gtggaggaga attcccaagg  27240
gcgaaaatag cgtagcagct tgcttcggac ccaggggagg cttcaaaaat tttggagatg  27300
cggaatttgt cgaaaaaggt gttgatgcct caggctatgc tcagatcgcc agtttagcac  27360
caaatgttgc agcattgctc tttggtggta atgtggctgt tcgtgagcta gcggactctt  27420
acgagattac atataattat aaaatgactg tgccaaagtc tgatccaaat gtagagcttc  27480
ttgtttcaca ggtggatgca tttaaaactg ggaatgcaaa accccagaga aagaaggaaa  27540
agaagaacaa gcgtgaaacc acgcagcagc tgaatgaaga ggccatctac gatgatgtgg  27600
gtgtgccatc tgatgtgact catgccaatt tggaatggga cacagctgtt gatggtggtg  27660
acacggccgt tgaaattatc aacgagatct tcgacacagg aaattaaaca atgtttgact  27720
ggcttatcct ggctatgtcc cagggtagtg ccattacact gttattactg agtgtttttc  27780
tagcgacttg gctgctgggc tatggctttg ccctctaact agcggtcttg gtcttgcaca  27840
caacggtaag ccagtggtaa tgtcagtgca agaaggatat taccatagca ctgtcatgag  27900
gggaacgcag taccttttca tctaaacctt tgcacgagta atcaaagatc cgcttgacga  27960
gcctatatgg aagagcgtgc caggtatttg actcaaggac tgttagtaac tgaagacctg  28020
acggtgttga tatggataca caaaaaaaaa aaaaaaaaaa aa                    28062
```

<210> SEQ ID NO 35
<211> LENGTH: 28062
<212> TYPE: DNA
<213> ORGANISM: porcine epidemic diarrhea virus

<400> SEQUENCE: 35

```
acttaaagag attttctatc tacggatagt tagctctttt tctagactct tgtctactca     60
attcaactaa acgaaatttt gtccttccgg ccgcatgtcc atgctgctgg aagctgacgt    120
ggaatttcat taggtttgct taagtagcca tcgcaagtgc tgtgctgtcc tctagttcct    180
ggttggcgtt ccgtcgcctt ctacatacta gacaaacagc cttcctccgg ttccgtctgg    240
gggttgtgtg gataactagt tctgtctagt ttgaaaccag taactgtcgg ctatggctag    300
caaccatgtt acattggctt ttgccaatga tgcagaaatt tcagcttttg gcttttgcac    360
tgctagtgaa gccgtctcat actattctga ggccgccgct agtggattta tgcaatgccg    420
tgccgtgtcc ttcgatctcg ctgacactgt tgagggattg cttcccgaag actatgtcat    480
ggtggtggtc ggcactacca agcttagtgc gtatgtggac acttttggta gccgccccaa    540
aaacatttgt ggttggctgt tattttctaa ctgtaattac ttcctcgaag agttagagct    600
tacttttggt cgtcgtggtg gtaacatcgt gccagttgac caatacatgt gtggcgctga    660
cggtaaacct gttcttcagg aatccgaatg ggagtataca gatttctttg ctgactccga    720
agacggtcaa ctcaacattg ctggtatcac ttatgtgaag gcctggattg tagagcgatc    780
ggatgtctct tatgcgagtc agaatttaac atctattaag tctattactt actgttcaac    840
ctatgagcat acttttcctg atggtactgc catgaaggtt gcacgtactc caaagattaa    900
gaagactgtt gtcttgtctg agccacttgc tactatctac agggaaattg gttctccttt    960
tgtggataat gggagcgatg ctcgttctat cattaagaga ccagtgttcc tccacgcttt   1020
tgttaagtgt aagtgtggta gttatcattg gactgttggt gattggactt cctatgtctc   1080
```

```
cacttgctgt ggctttaagt gtaagccagt ccttgtggct tcatgctctg ctacgcctgg   1140
ttctgttgtg gttacgcgcg ctggtgctgg cactggtgtt aagtattaca acaacatgtt   1200
cctgcgccat gtggcagaca ttgatgggtt ggcattctgg cgaattctca aggtgcagtc   1260
caaagacgac ctcgcttgct ctggtaaatt ccttgaacac catgaggaag gtttcacaga   1320
tccttgctac tttttgaatg actcgagcat tgctactaag ctcaagtttg acatccttag   1380
tggcaagttt tctgatgaag tcaaacaagc tatctttgct ggtcatgttg ttgttggcag   1440
cgcgctcgtt gacattgttg acgatgcact gggacagcct tggtttatac gtaagcttgg   1500
tgaccttgca agtgcagctt gggagcagct taaggctgtc gttagaggcc ttaacctcct   1560
gtctgatgag gtcgtgctct ttggcaaaag acttagctgt gccactctta gtatcgttaa   1620
cggtgttttt gagttcatcg ccgaagtgcc tgagaagttg gctgcggctg ttacagtttt   1680
tgtcaacttc ttgaatgagc tttttgagtc tgcctgtgac tgcttaaagg tcggaggtaa   1740
aacctttaac aaggttggct cttatgttct ttttgacaac gcattggtta agcttgtcaa   1800
ggcaaaagtt cgcggcccac gacaggcagg tgtttgtgaa gttcgttaca caagccttgt   1860
tattgggagt actaccaagg tggtttccaa gcgcgttgaa aatgccaatg tgaatctcgt   1920
cgtcgttgac gaggatgtga ccctcaacac cactggtcgt acagttgttg ttgacggact   1980
tgcattcttc gagagtgacg ggttttacag acatcttgct gatgctgacg ttgtcattga   2040
acatcctgtt tataagtctg cttgtgagct caagccagtt tttgagtgtg acccaatacc   2100
tgattttcct atgcctgtgg ccgctagtgt tgcagagctt tgtgtgcaaa ctgatctgtt   2160
gcttaaaaat tacaacactc cttataaaac ttacagctgc gttgtgagag gtgataagtg   2220
ttgtatcact tgcaccttac atttcacagc accaagttat atggaggctg ctgctaattt   2280
tgtagacctc tgtaccaaga acattggtac tgctggtttt catgagtttt acattacggc   2340
ccatgaacaa caggatctgc aagggttcgt aaccacttgt tgcacgatgt caggttttga   2400
gtgttttatg cctataatcc cacagtgtcc agcagtgctt gaagagattg atggtggtag   2460
catctggcgg tcttttatca ctggtcttaa tacaatgtgg gatttttgca agcatcttaa   2520
agtcagcttt ggactagatg gcattgttgt cactgtagca cgcaaattta aacgacttgg   2580
tgctctcttg gcagaaatgt ataacactta cctttcaact gtggtggaaa acttggtact   2640
ggccggtgtt agcttcaagt attatgccac cagtgtccca aaaattgttt tgggctgttg   2700
ttttcacagt gttaaaagtg ttcttgcaag tgccttccag attcctgtcc aggcaggcgt   2760
tgagaagttt aaagtcttcc ttaactgtgt tcaccctgtt gtaccacgtg tcattgaaac   2820
ttcttttgtg gaattagaag agacgacatt taaaccacca gcactcaatg gtagtattgc   2880
tattgttgat ggctttgctt tctattatga tggaacacta tactatccca ccgatggtaa   2940
tagcgttgtt cctatctgct ttaagaagaa aggtggtggt gatgtcaaat tctctgatga   3000
agtctctgtt aaaaccattg acccagttta taaggtctcc cttgaatttg agttcgagtc   3060
tgagactatt atggctgtgc ttaataaggc tgttggtaat tgtatcaagg ttacaggtgg   3120
ttgggacgat gttgttgagt atatcaatgt tgccattgag gttcttaaag atcacatcga   3180
tgtgcctaag tactacatct atgatgagga aggtggcacc gatcctaatc tgcccgtaat   3240
ggtttctcag tggccgttga atgatgacac gatctcacag gatctgcttg atgttgaagt   3300
tgttactgat gcgccagttg atttcgaggg tgatgaagta gactcctctg accctgataa   3360
ggtggcagac gtggctaact ctgagcctga ggatgacggt cttaatgtag ctcctgaaac   3420
aaatgtagag tctgaagttg aggaagttgc cgcaaccttg tcctttatta aagatacacc   3480
```

```
ttccacagtt actaaggatc cttttgcttt tgactttgca agctatggag gacttaaggt   3540
tttaagacaa tctcataaca actgctgggt tacttctacc ttggtgcagc tacaattgct   3600
tggcatcgtt gatgaccctg caatggagct tttagtgct ggtagagttg gtccaatggt   3660
tcgcaaatgc tatgagtcac aaaaggctat cttgggatct ttgggtgatg tgtcggcttg   3720
cctagagtct ctgactaagg acctacacac acttaagatt acctgttctg tagtctgtgg   3780
ttgtggtact ggtgaacgta tctatgatgg ttgtgctttt cgtatgacgc caactttgga   3840
accgttccca tatggtgctt gtgctcagtg tgctcaagtt ttgatgcaca cttttaaaag   3900
tattgttggc accggcatct tttgtcgaga tactactgct ctctccttgg attctttggt   3960
tgtaaaacct ctttgtgcgg ctgcttttat aggcaaggat agtggtcatt atgtcactaa   4020
cttttatgat gccgctatgg ctattgatgg ttatggtcgt catcagataa agtatgacac   4080
actgaacact atttgtgtta aagacgttaa ttggacagca ccttttgtcc cagacgttga   4140
gcctgtattg gagcttgttg tcaaaccttt ctattcttat aagaatgttg atttttacca   4200
aggagatttt agtgaccttg ttaaacttcc atgtgatttt gttgttaatg ctgcaaatga   4260
gaatttgtct cacggtggcg gcatagcaaa ggccattgat gtttatacca agggcatgtt   4320
gcagaagtgc tcgaatgatt acattaaagc acacggtccc attaaagttg gacgtggtgt   4380
catgttggag gcattaggtc ttaaggtctt taatgttgtt ggtccacgta agggtaagca   4440
tgcacctgag cttcttgtta aggcttataa gtccgttttt gctaattcag gtgttgctct   4500
tacacctttg attagtgttg gaatttttag tgttcctttg gaagaatctt tatctgcttt   4560
tcttgcatgt gttggtgatc gccactgtaa gtgcttttgt tatagtgaca aagagcgcga   4620
ggcgatcatt aattacatgg atggcttggt agatgctatt ttcaaagatg cacttgttga   4680
tactactcct gtccaggaag atgttcaaca agtttcacaa aaaccagttt tgcctaattt   4740
tgaacctttc aggattgaag gtgctcatgc tttctatgag tgcaaccctg aaggtttgat   4800
gtcattaggt gctgacaagc tggtgttgtt tacaaattcc aatttggatt tttgtagcgt   4860
tggtaagtgt cttaacaatg tgactggcgg tgcattgctt gaagccataa atgtatttaa   4920
aaagagtaac aaaacagtgc ctgctggcaa ctgtgttact tttgagtgtg cagatatgat   4980
ttctattact atggtagtat tgccatctga cggtgatgct aattatgaca aaaattatgc   5040
acgcgccgtc gtcaaggtat ctaagcttaa aggcaagtta ttgcttgctg ttggtgatgc   5100
catgttgtat tccaagttgt cccacctcag cgtgttaggt ttcgtatcca cacctgatga   5160
tgtggagcgt ttctacgcaa ataagagtgt ggttattaaa gttactgagg atacacgtag   5220
tgttaagact gttaaagtag aatccactgt tacttatgga caacaaattg gaccttgtct   5280
tgttaatgac accgttgtca cagacaacaa acctgttgtt gctgatgttg tagctaaggt   5340
tgtaccaagt gctaattggg attcacatta tggttttgat aaggctggtg agttccacat   5400
gctagaccat actgggtttg cctttcctag tgaagttgtt aacggtaggc gtgtgcttaa   5460
aaccacagat aataactgtt gggttaatgt tacatgttta caattacagt ttgctagatt   5520
taggttcaag tcagcaggtc tacaggctat gtgggagtcc tattgtactg gtgatgttgc   5580
tatgtttgtg cattggttgt actggcttac tggtgttgac aaaggtcagc ctagtgattc   5640
agaaaatgca cttaacatgt tgtctaagta cattgttcct gctggttctg tcactattga   5700
acgtgtcacg catgacggtt gttgttgtag taagcgtgtt gtcactgcac cagttgtgaa   5760
tgctagcgtg ttgaagcttg gcgtcgagga tggtctttgt ccacatggtc ttaactacat   5820
```

-continued

```
tgacaaagtt gttgtagtta aaggtactac aattgttgtc aatgttggaa aacctgtagt   5880
ggcaccatcg cacctctttc ttaagggtgt ttcctacaca acattcctag ataatggtaa   5940
cggtgttgcc ggccattata ctgtttttga tcatgacact ggtatggtgc atgatggaga   6000
tgtttttgta ccaggtgatc tcaatgtgtc tcctgttaca aatgttgtcg tctcagagca   6060
gacggctgtt gtgattaaag accctgtgaa gaaagtagag ttagacgcta caaagctgtt   6120
agacactatg aattatgcat cggaaagatt cttttccttt ggtgatttta tgtcacgtaa   6180
tttaattaca gtgtttttgt acatccttag tattttgggt ctctgtttta gggcctttcg   6240
taagagggat gttaaagttc tagctggtgt accccaacgt actggtatta tattgcgtaa   6300
aagtgtgcgc tataatgcaa aggctttggg tgtcttcttc aagctaaaac tttattggtt   6360
caaagttctt ggtaagttta gtttgggtat ttatgcattg tatgcattac tattcatgac   6420
aatacgcttt acacctatag gtggccctgt ttgtgatgat gttgttgctg gttatgctaa   6480
ttctagtttt gacaagaatg agtattgcaa cagtgttatt tgtaaggtct gtctctatgg   6540
gtaccaggaa ctttcggact tctctcacac acaggtagta tggcaacacc ttagagaccc   6600
attaattggt aatgtgatgc ctttctttta tttggcattt ctggcaattt ttggggggtgt   6660
ttatgtaaag gctattactc tctattttat tttccagtat cttaacatac ttggtgtgtt   6720
tttgggccta caacagtcca tttggttttt gcagcttgtg ccttttgatg tctttggtga   6780
cgagatcgtc gtctttttca tcgttacacg cgtattgatg ttccttaagc atgttttcct   6840
tggctgcgat aaggcatctt gtgtggcttg ctctaagagt gctcgcctta agcgcgttcc   6900
tgtccagact atttttcagg gtactagcaa atccttctac gtacatgcca atggtggttc   6960
taagttctgt aagaagcaca atttcttttg tttaaattgt gattcttatg gtccaggctg   7020
cacttttatt aatgacgtca ttgcaactga agttggtaat gttgtcaaac ttaatgtgca   7080
accgacaggt cctgccacta ttcttattga caaggttgaa ttcagtaatg gtttttacta   7140
tctttatagt ggtgacacat tttggaagta caactttgac ataacagata acaaatacac   7200
ttgcaaagag tcacttaaaa attgtagcat aatcacagac tttattgttt ttaacaataa   7260
tggttccaat gtaaatcagg ttaagaatgc atgtgtgtat ttttcacaga tgctttgtaa   7320
acctgttaag ttagtggact cagcgttgtt ggccagtttg tctgttgatt ttggtgcaag   7380
cttacatagt gcttttgtta gtgtgttgtc gaatagtttt ggcaaagacc tgtcaagttg   7440
taatgacatg caggattgca agagcacatt gggttttgat gatgtaccat tggatacctt   7500
taatgctgct gttgctgagg ctcatcgtta cgatgtcctc ttgactgaca tgtcgttcaa   7560
caattttacc accagttatg caaaaccaga ggaaaaactt cccgtccatg acattgccac   7620
gtgtatgcgt gtaggtgcca agattgttaa tcataacgtt cttgtcaagg atagtatacc   7680
tgtggtgtgg cttgtacgtg atttcattgc cctttctgaa gaaactagga agtacattat   7740
tcgtacgact aaagttaagg gtataacctt catgttgacc tttaatgatt gtcgtatgca   7800
tactaccata cctactgttt gcattgcaaa taagaagggt gcaggtcttc ctagtttttc   7860
aaaggttaag aaattcttct ggtttttgtg tctgttcata gttgctgttt tctttgcact   7920
aagctttttt gattttagta ctcaggttag cagtgatagt gattatgact tcaagtatat   7980
tgagagtggc cagttgaaga cttttgacaa tccacttagt tgtgtgcata atgtctttag   8040
taacttcgac cagtggcatg atgccaagtt tggtttcacc cccgtcaaca atcctagttg   8100
tcctatagtc gttggtgtat cagacgaagc gcgcactgtt ccaggtatcc cagcaggtgt   8160
ttatttagct ggtaaaacac ttgtttttgc tattaacacc atttttggta catctggttt   8220
```

```
gtgctttgat gctagtggcg ttgctgataa gggcgcttgc atttttaatt cggcttgcac   8280
cacattatct ggtttgggtg gaactgctgt ctactgttat aagaatggtc tagttgaagg   8340
tgctaaactt tatagtgagt tggcacctca tagctactat aaaatggtag atggtaatgc   8400
tgtgtcttta cctgaaatta tctcacgcgg ctttggcatc cgtactatcc gtacaaaggc   8460
tatgacctac tgtcgcgttg gccagtgtgt gcaatctgca gaaggtgttt gttttggcgc   8520
cgatagattc tttgtctata atgcagaatc tggttctgac tttgtttgtg gcacagggct   8580
ctttacattg ttgatgaacg ttattagtgt tttttccaag acagtaccag taactgtgtt   8640
gtctggtcaa atacttttta attgcattat tgcttttgct gctgttgcgg tgtgtttctt   8700
atttacaaag tttaagcgca tgttcggtga tatgtctgtt ggcgttttca ctgtcggtgc   8760
ttgtactttg ttgaacaatg tttcctacat tgtaacacag aacacacttg gcatgttggg   8820
ctatgcaact ttgtactttt tgtgcactaa aggtgttaga tatatgtgga tttggcattt   8880
gggatttttg atctcatata tacttattgc accatggtgg gttttgatgg tttatgcctt   8940
ttcagccatt tttgagttta tgcctaacct ttttaagctt aaggtttcaa cacaactttt   9000
tgagggtgac aagttcgtag gctcttttga aaatgctgca gcaggtacat ttgtgcttga   9060
tatgcatgcc tatgagagac ttgccaactc tatctcaact gaaaaactgc gtcagtatgc   9120
tagtacttac aataagtaca agtattattc aggcagtgct tcagaggctg attacaggct   9180
tgcttgtttt gcccatttgg ccaaggctat gatggattat gcttctaatc acaacgacac   9240
gttatacaca ccacccactg tgagttacaa ttcaactcta caggctggct tgcgtaagat   9300
ggcacaacca tctggtgttg ttgagaagtg catagttcgt gtttgctatg gtaatatggc   9360
tcttaatggc ctatggcttg gtgatactgt tatctgccca cgccatgtta tagcgtctag   9420
tactactagc actatagatt atgactatgc cctttctgtt ttacgcctcc acaacttctc   9480
catttcatct ggtaatgttt tcctaggtgt tgtgggtgta accatgcgag gtgctttgtt   9540
gcagataaag gttaatcaaa acaatgtcca cacgcctaag tacacctatc gcacagttag   9600
accgggtgaa tcttttaata tcttggcgtg ctatgatggt tctgcagctg gtgtttacgg   9660
cgttaacatg cgctctaatt acactattag aggctcgttc attaatggcg cttgtggttc   9720
acctggttat aacattaaca atggtaccgt tgagttttgc tatttacacc agcttgaact   9780
tggttcaggc tgtcatgttg gtagcgactt agatggtgtt atgtatggtg gttatgagga   9840
ccaacctact ttgcaagttg aaggcgctag tagtctgttt acagagaatg tgttggcatt   9900
tctttatgca gcactcatta atggttctac ctggtggctt agttcttcta ggattgctgt   9960
agacaggttt aatgagtggg ctgttcataa tggtatgaca acagtagtta atactgattg  10020
cttttctatt cttgctgcta agactggtgt tgatgtacaa cgtttgttgg cctcaatcca  10080
gtctctgcat aagaattttg gtggaaagca aattcttggc tatacctcgt tgacagatga  10140
gtttactaca ggtgaagtta tacgtcaaat gtatggcgtt aatcttcaga gtggttatgt  10200
ttcacgcgcc tgtagaaatg tcttgctggt tggttctttt ctgactttct tttggtcaga  10260
attagtttcc tacactaagt tcttttgggt aaatcctggt tatgtcacac ctatgtttgc  10320
gtgtttgtca ttgctgtcct cacttttgat gttcacactc aagcataaga cattgttttt  10380
ccaggtcttt ctaatacctg ctctgattgt tacatcttgc attaatttgg catttgatgt  10440
tgaagtctac aactatttgg cagagcattt tgattaccat gtttctctca tgggttttaa  10500
tgcacaaggt cttgttaaca tctttgtctg ctttgttgtt accattttac acggcacata  10560
```

```
cacatggcgc ttttttaaca cacctgtgag ttctgtcact tatgtggtag ctttgctgac  10620
tgcggcatat aactattttt acgctagtga cattcttagt tgtgctatga cactatttgc  10680
tagtgtgact ggcaactggt tcgttggtgc tgtttgttat aaagctgctg tttatatggc  10740
cttgagattt cctacttttg tggctatttt tggtgatatt aagagtgtta tgttctgtta  10800
ccttgtgttg ggttatttta cctgttgctt ctacggtatt ctctactggt tcaacaggtt  10860
ttttaaggtt agtgtaggtg tctatgacta tactgttagt gctgctgagt ttaagtatat  10920
ggttgctaac ggcctacgtg caccaactgg aacacttgat tcactacttc tgtctgccaa  10980
attgattggt attggtggtg agcggaatat taagatttct tccgttcagt ctaaactgac  11040
tgatattaag tgtagtaacg ttgtgctttt aggctgtctc tctagcatga atgtctcagc  11100
aaattcaaca gaatgggcct attgtgttga cttgcataac aagatcaact tgtgtaatga  11160
cccagaaaaa gcgcaggaaa tgctacttgc tttgttggca tttttcctta gtaagaatag  11220
tgcttttggt ttagatgact tattggaatc ctattttaat gacaatagta tgttgcagag  11280
tgttgcatct acttatgtcg gtttgccttc ttatgtcatt tatgaaaatg cacgccaaca  11340
gtatgaagat gctgttaata atggttctcc acctcagttg gttaagcaat tgcgccatgc  11400
catgaatgta gcaaagagcg aatttgaccg tgaggcttct actcagcgta agcttgatag  11460
aatggcggaa caggctgcag cacagatgta caaagaggca cgagcagtta ataggaagtc  11520
caaagttgta agtgctatgc attcactgct tttggtatg ttgagacgtt tggacatgtc  11580
ttctgtagac accattctca acttggcaaa ggatggggtt gtacctctgt ctgtcatacc  11640
ggcagtcagt gctactaagc ttaacattgt tacttctgat atcgattctt ataatcgtat  11700
ccagcgtgag ggatgtgtcc actacgctgg taccatttgg aatataattg atatcaagga  11760
caatgatggc aaggtggtac acgttaagga ggtaaccgca cagaatgctg agtccctgtc  11820
atggcccctg gtccttgggt gtgagcgtat tgtcaagctc cagaataatg aaattattcc  11880
cggtaagctg aagcagcgct ccattaaggc agaaggagat ggcatagttg gagaaggtaa  11940
ggcactttac aataatgagg gtggacgtac ttttatgtat gctttcatct cggacaaacc  12000
ggacctgcgt gtagtcaagt gggagttcga tggtggttgt aacactattg agctagaacc  12060
accacgtaag ttcttggtgg attctcctaa tggtgcacag atcaagtatc tctactttgt  12120
tcgtaacctt aacacgttac gtaggggtgc tgttctcggc tacataggtg ccactgtacg  12180
cttgcaggct ggtaaacaaa cagaacaggc tattaactct tcattgttga cactttgcgc  12240
tttcgctgtg gatcctgcta agacctacat cgatgctgtc aaaagtggtc acaaaccagt  12300
aggtaactgt gttaagatgt tggccaatgg ttctggtaat ggacaagctg ttactaatgg  12360
tgtggaggct agtactaacc aggattcata cggtggtgcg tccgtgtgtc tatattgtag  12420
agcacatgtt gagcatccat ctatggatgg tttttgcaga ctgaaaggca agtacgtaca  12480
ggttccacta ggtacagtgg atcctatacg ttttgtactt gagaatgacg tttgcaaggt  12540
ttgtggttgt tggctggcta atggctgcac ttgtgacaga tccattatgc aaagcactga  12600
tatggcttat ttaaacgagt acggggctct agtgcagctc gactagagcc ctgtaacggt  12660
actgatacac aacatgtgta tcgtgctttt gacatctaca acaaggatgt tgcttgtcta  12720
ggtaaattcc tcaaggtgaa ctgtgttcgc ctgaagaatt tggataagca tgatgcattc  12780
tatgttgtca aaagatgtac caagtctgcg atggaacacg agcaatccat ctatagcaga  12840
cttgaaaagt gtggagccgt agccgaacac gatttcttca cttggaagga tggtcgtgcc  12900
atctatggta acgtttgtag aaaggatctt accgagtata ctatgatgga tttgtgttac  12960
```

```
gctttacgta actttgatga aaacaattgc gatgttctta agagcatttt aattaaggta  13020
ggcgcttgtg aggagtccta cttcaataat aaagtctggt ttgaccctgt tgaaaatgaa  13080
gacattcatc gtgtctatgc attgttaggt accattgttt cacgtgctat gcttaaatgc  13140
gttaagttct gtgatgcaat ggttgaacaa ggtatagttg gtgttgtcac attagataat  13200
caggatctta atggtgattt ttatgatttt ggtgatttta cttgtagcat caagggaatg  13260
ggtataccca tttgcacatc atattactct tatatgatgc ctgttatggg tatgactaat  13320
tgccttgcta gtgagtgttt tgttaagagt gatatatttg gtgaggattt caagtcatat  13380
gacctgctgg aatatgattt cacggagcat aagacagcac tcttcaacaa gtatttcaag  13440
tattggggac tgcaatacca ccctaattgt gtggactgca gtgatgagca gtgcatagtt  13500
cactgtgcca acttcaatac gttgttttcc actactatac ctattacggc atttggacct  13560
ttgtgtcgca agtgttggat tgatggtgtt ccactggtaa ttacagctgg ttatcatttt  13620
aaacagttag gtatagtttg gaacaatgac ctcaacttac actctagcag gctctctatt  13680
aacgaattac tccagttttg tagtgatcct gcattgctta tagcatcatc accagccctt  13740
gttgatcagc gtactgtttg cttttcagtt gcagcgctag gtacaggtat gactaaccag  13800
actgttaaac ctggccattt caataaggag ttttatgact tcttacttga gcaaggtttc  13860
ttttctgagg gctctgagct tactttaaag cacttcttct ttgcacagaa gggtgatgca  13920
gctgttaagg attttgacta ctataggtat aatagaccta ctgttctgga catttgccaa  13980
gctcgcgtcg tgtatcaaat agtgcaacgc tattttgata tttacgaagg tggttgtatc  14040
actgctaaag aggtggttgt tacaaacctt aacaagagcg caggttatcc tttgaacaag  14100
tttggtaaag ctggtcttta ctatgagtct ttatcctatg aggaacagga tgaactttat  14160
gcttatacta agcgtaacat cctgcccact atgacacagc tcaaccttaa atatgctata  14220
agtggcaaag aacgtgcacg cacagtgggt ggtgtttcgc ttttgtcaac catgactact  14280
cggcagtatc atcagaaaca ccttaagtcc atagttaata ctaggggcgc ttcggttgtt  14340
attggtacta ctaagtttta tggtggttgg gacaatatgc ttaagaacct tattgatggt  14400
gttgaaaatc cgtgtcttat gggttgggac tacccaaagt gcgacagagc actgcccaat  14460
atgatacgta tgatttcagc catgatttta ggctctaagc acaccacatg ctgcagttcc  14520
actgaccgct tttcaggtt gtgcaatgaa ttggctcaag tccttactga ggttgtttat  14580
tctaatggag gtttttattt gaagccaggt ggtactacct ctggtgatgc aaccaccgca  14640
tatgcaaact cagtttttaa tatcttccaa gcagtaagtg ccaatgttaa caaacttctt  14700
agtgttgaca gcaatgtctg tcataattta gaagttaagc aattgcagcg taagctttat  14760
gagtgctgtt atagatcaac taccgtcgat gaccagttcg tcgttgagta ttatggttac  14820
ttgcgtaaac atttttcaat gatgattctt tctgatgatg gcgttgtttg ttataacaat  14880
gactatgcat cacttggtta tgtcgctgat cttaacgcct tcaaggctgt tttgtattac  14940
cagaacaatg tcttcatgag cgcctctaaa tgttggatcg agcctgacat taataaaggt  15000
cctcatgaat tttgctcgca gcatactatg cagattgtcg ataaagatgg tacttattac  15060
cttccttacc ctgatccttc aagaattctc tctgcaggtg tgtttgttga tgacgttgtt  15120
aaaactgatg cagttgtatt gcttgaacgt tatgtgtcat tggctataga tgcctacccg  15180
ttatctaagc atgaaaaccc tgaatataag aaggtgtttt atgtgctttt ggattgggtt  15240
aagcatctgt acaaaactct taatgctggt gtgttagagt ctttttctgt cacacttttg  15300
```

-continued

```
gaagattcta ctgctaaatt ctgggatgag agcttttatg ccaacatgta tgagaaatct  15360
gcagttttac aatctgcagg gctttgtgtt gtttgtggct ctcaaactgt tttacgttgt  15420
ggtgattgtc tacggcgtcc tatgctttgt actaagtgtg cttatgatca tgtcattgga  15480
acaactcaca agttcatttt ggccatcact ccatatgtgt gttgtgcttc agattgtggt  15540
gtcaatgatg taactaagct ctacttaggt ggtcttagtt attggtgtca tgaccacaag  15600
ccacgtcttg cattcccgtt gtgctctgct ggtaatgttt ttggcttgta caaaaattct  15660
gctaccggct cacccgatgt tgaagacttt aatcgcattg ctacatccga ttggactgat  15720
gtttctgact acaggttggc aaatgatgtc aaggactcat tgcgtctgtt tgcagcggaa  15780
actatcaagg ccaaggagga gagcgttaag tcatcctatg cttgtgcaac actacatgag  15840
gttgtaggac ctaaagagtt gttgctcaaa tgggaagtcg gcagacccaa accacccctt  15900
aatagaaatt cggttttcac ttgttatcat ataacgaaga acaccaaatt tcaaatcggt  15960
gagtttgtgt ttgagaaggc agaatatgat aatgatgctg taacatataa aactaccgcc  16020
acaacaaaac ttgttcctgg catggttttt gtgcttacct cacataatgt tcagccattg  16080
cgcgcaccga ccattgctaa tcaagaacgt tattccacta tacataagtt gcatcctgct  16140
tttaacatac ctgaagctta ttctagctta gtgccctatt accaattgat tggtaagcag  16200
aagattacaa ctattcaggg acctcccggt agtggtaaat ctcactgtgt tatagggcta  16260
ggtttgtact atccaggtgc acgtatagtg tttacagctt gttctcatgc agcggtcgat  16320
tcactttgtg tgaaagcttc cactgcttat agcaatgaca aatgttcacg catcatacca  16380
cagcgcgctc gtgttgagtg ttatgatggt ttcaagtcta ataatactag tgctcagtac  16440
cttttctcta ctgtcaatgc tttgccagag tgcaatgcgg acattgttgt ggtggatgag  16500
gtctctatgt gcactaatta tgacttgtct gtcataaatc agcgcatcag ctataggcat  16560
gtagtctatg ttggtgaccc tcaacagctg cctgcaccac gtgttatgat ttcacgtggt  16620
actttggaac caaaggacta caacgttgtc actcaacgca tgtgtgccct taagcctgat  16680
gttttcttgc acaagtgtta tcgctgtcct gctgagatag tgcgtactgt gtctgagatg  16740
gtctatgaaa accaattcat tcctgtgcac ccagatagca agcagtgttt taaaatcttt  16800
tgcaagggta atgttcaggt tgataatggt tcaagcatta atcgcaggca attggatgtt  16860
gtgcgtatgt tttggctaa aaatcctagg tggtcaaagg ctgtttttat ttctccttat  16920
aacagccaga attatgttgc cagccgcatg ctaggtctac aaattcagac agttgactca  16980
tcccagggta gtgagtatga ctatgtcatt tacacacaaa cttcagatac tgcccatgcc  17040
tgtaatgtta acaggtttaa tgttgccatc acaagggcca agaaaggcat attatgtata  17100
atgtgcgata ggtccctttt tgatgtgctt aaattctttg agcttaaatt gtctgatttg  17160
caggctaatg agggttgtgg tctttttaaa gactgtagca gaggtgatga tctgttgcca  17220
ccatctcacg ctaacacctt catgtcttta gcggacaatt ttaagactga tcaagatctt  17280
gctgttcaaa taggtgttaa tggacccatt aaatatgagc atgttatctc gtttatgggt  17340
ttccgttttg atatcaacat acccaaccat catactctct tttgcacacg cgactttgcc  17400
atgcgcaatg ttagaggttg gttaggcttt gacgttgaag gagcacatgt tgttggctct  17460
aacgtcggta caaatgtccc attgcaatta gggttttcta acggtgttga ttttgttgtc  17520
agacctgaag gttgcgttgt aacagagtct ggtgactaca ttaaacccgt cagagctcgt  17580
gctccaccag gggaacaatt cgcacacctt ttgcctttac ttaaacgcgg ccaaccatgg  17640
gatgttgtcc gcaaacgtat agtgcagatg tgtagtgact acctggccaa cctatcagac  17700
```

```
atactaattt ttgtgttgtg ggctggtggt ttggagttga caactatgcg ttattttgtc  17760
aagattggac caagtaagag ttgtgattgt ggtaaggttg ctacttgtta caatagtgcg  17820
ctgcatacgt actgttgttt caaacatgcc cttggttgtg attatctgta taacccatac  17880
tgtattgata tacagcagtg gggatacaag ggatcactta gccttaacca ccatgagcat  17940
tgtaatgtac atagaaacga gcatgtggct tctggtgatg ccataatgac tcgctgtctg  18000
gccatacatg attgctttgt caagaacgtt gactggtcca tcacataccc atttattggt  18060
aatgaggctg ttattaataa gagcggccga attgtgcaat cacacactat gcggtcagtt  18120
cttaagttat acaatccgaa agccatatat gatattggca atcctaaggg cattagatgt  18180
gccgtaacgg atgctaagtg gttttgcttt gacaagaatc ctactaattc taatgtcaag  18240
acattggagt atgactatat aacacatggc caatttgatg ggttgtgctt gttttggaat  18300
tgcaatgtag acatgtatcc agaattttct gtggtctgtc gttttgatac tcgctgtagg  18360
tcaccactca acttggaggg ttgtaatggt ggttcactgt atgttaataa tcatgcattc  18420
catacaccgg cttttgacaa gcgtgctttt gctaagttga agccaatgcc atttttcttt  18480
tatgatgata ctgagtgtga caagttacag gactccataa actatgttcc tcttagggct  18540
agtaactgca ttactaaatg taatgttggt ggtgctgtct gtagtaagca ttgtgctatg  18600
tatcatagct atgttaatgc ttacaacact tttacgtcgg cgggctttac tatttgggtg  18660
cctacttcgt ttgacaccta taatctgtgg cagacattta gtaacaattt gcaaggtctt  18720
gagaacattg ctttcaatgt cgtaaagaaa ggatcttttg ttggtgccga aggtgaactt  18780
cctgtagctg tggttaatga caaagtgctc gttagagatg gtactgttga tactcttgtt  18840
tttacaaaca agacatcact acccactaac gtagcttttg agttgtatgc caagcgtaag  18900
gtaggactca ccccacccat tacgatccta cgtaacttgg gtgtagtttg tacatctaag  18960
tgtgtcattt gggactatga agccgaacgt ccacttacta cttttacaaa ggatgtttgt  19020
aaatataccg actttgaggg tgacgtctgt acactctttg ataacagcat tgttggttca  19080
ttagagcgat tctccatgac ccaaaatgct gtgcttatgt cacttacagc tgttaaaaag  19140
cttactggca taaagttaac ttatggttat cttaatggtg tcccagttaa cacacatgaa  19200
gataaacctt ttacttggta tatttacact aggaagaacg gcaagttcga ggaccatcct  19260
gatggctatt ttacccaagg tagaacaacc gctgatttta gccctcgtag cgacatggaa  19320
aaggacttcc taagtatgga tatgggtctg tttattaaca agtacggact tgaggattac  19380
ggctttgagg ccgttgtgta tggtgatgtt tcaaaaacca cccttggtgg tttggcccta  19440
ctaatttcgc aggtgcgtct ggcctgtatg ggtgtgctca aaatagacga gtttgtgtct  19500
agtaatgata gcacgttaaa gtcttgtact gttacatatg ctgataaccc tagtagtaag  19560
atggtttgta cgtatatgga tctcctgctt gacgattttg tcagcattct taaatctttg  19620
gatttgggcg ttgtatctaa agttcatgaa gttatggtcg attgtaaaat gtggaggtgg  19680
atgttgtggt gtaaggatca taaactccag acattttatc cgcaacttca ggccagtgaa  19740
tggaagtgtg gttattccat gccttctatt tacaagatac aacgtatgtg tttagaacct  19800
tgcaatctct acaactatgg tgctggtatt aagttacctg atggcattat gtttaacgta  19860
gttaaataca cacagctttg tcaatatctc aatagcacca caatgtgtgt accccatcac  19920
atgcgtgtgc tacatcttgg tgctggctcc gacaagggtg ttgcacctgg cacggctgtc  19980
ttacgacgtt ggttgccact ggatgccatt atagttgaca atgatagtgt ggattacgtt  20040
```

```
agcgatgctg attatagtgt tacaggagat tgctctacct tatacctgtc agataagttt  20100
gatttagtta tatctgcaat gtatgatggt aagattaaaa gttgtgatgg ggagaacgtg  20160
tctaaagaag gcttctttcc ctatattaat ggtgtcatca ccgaaaagtt ggcacttggt  20220
ggtactgtag ctattaaggt gacggagttt agttggaata agaagttgta tgaactcatt  20280
cagaggtttg agtattggac aatgttctgt accagtgtta acacgtcatc gtcagaggca  20340
ttcttaattg gtgttcacta tttaggtgat tttgcaagtg gcgctgtgat tgacggcaac  20400
actatgcatg ccaattatat cttctggcgt aattccacaa ttatgactat gtcttacaat  20460
agtgtacttg atttaagcaa gttcaattgt aagcataagg ctacagttgt cattaattta  20520
aaagattcat ccattagtga tgttgtgtta ggtttgttga agaatggtaa gttgctagtg  20580
cgtaataatg acgccatttg tggtttttct aatcatttgg tcaacgtaaa caaatgaagt  20640
ctttaaccta cttctggttg ttcttaccag tactttcaac acttagccta ccacaagatg  20700
tcaccaggtg ctcagctaac actaatttta ggcggttctt ttcaaaattt aatgttcagg  20760
cgcctgcagt tgttgtactg ggcggttatc tacctattgg tgaaaaccag ggtgtcaatt  20820
caacttggta ctgtgctggc caacatccaa ctgctagtgg cgttcatggt atctttgtta  20880
gccatattag aggtggtcat ggctttgaga ttggcatttc gcaagagcct tttgacccta  20940
gtggttacca gctttattta cataaggcta ctaacggtaa cactaatgct actgcgcgac  21000
tgcgcatttg ccagtttcct agcattaaaa cattgggccc cactgctaat aatgatgtta  21060
caacaggtcg taattgccta tttaacaaag ccatcccagc tcatatgagt gaacatagtg  21120
ttgtcggcat aacatgggat aatgatcgtg tcactgtctt ttctgacaag atctattatt  21180
tttattttaa aaatgattgg tcccgtgttg cgacaaagtg ttacaacagt ggaggttgtg  21240
ctatgcaata tgtttacgaa cccacctatt acatgcttaa tgttactagt gctggtgagg  21300
atggtatttc ttatcaaccc tgtacagcta attgcattgg ttatgctgcc aatgtatttg  21360
ctactgagcc caatggccac ataccagaag gttttagttt taataattgg tttcttttgt  21420
ccaatgattc cactttggtg catggtaagg tggtttccaa ccaaccattg ttggtcaatt  21480
gtcttttggc cattcctaag atttatggac taggccaatt tttctccttt aatcaaacga  21540
tcgatggtgt ttgtaatgga gctgctgtgc agcgtgcccc agaggctctg aggtttaata  21600
ttaatgacat ctctgtcatt cttgctgaag gctcaattgt acttcatact gctttaggaa  21660
caaatttttc ttttgtttgc agtaattcct caaatcctca cttagccacc ttcgccatac  21720
ctctgggtgc tacccaagta ccttattatt gtttttttaa agtggatact tacaactcca  21780
ctgtttataa atttttggct gttttacctc ctaccgtcag ggaaattgtc atcaccaagt  21840
atggtgatgt ttatgtcaat gggtttggat acttgcatct cggtttgttg gatgctgtca  21900
caattaattt cactggtcat ggcactgacg atgatgtttc tggtttttgg accatagcat  21960
cgactaattt tgttgatgca ctcatcgaag ttcaaggaac cgccattcag cgtattcttt  22020
attgtgatgg gcatcctgtt agccaactca agtgttctca ggttgctttt gaccttgacg  22080
atggttttta cactatttct tctagaaacc ttctgagtca tgaacagcca atttcttttg  22140
ttactctgcc atcatttaat gatcattctt ttgttaacat tactgtatct gcttcctttg  22200
gtggtcatag tggtgccaac cttattgcat ctgacactac tatcaatggg tttagttctt  22260
tctgtgttga cactagacaa tttaccattt cactgtttta taacgttaca aacagttatg  22320
gttatgtgtc taaatcacag gacagtaatt gccctttcac cttgcaatct gttaatgatt  22380
acctgtcttt tagcaaattt tgtgtttcca ccagcctttt ggctagtgcc tgtaccatag  22440
```

```
atctttttgg ttaccctgag tttggtagtg gtgttaagtt tacgtccctt tactttcaat  22500
tcacaaaggg tgagttgatt actggcacgc ctaaaccact tgaaggtgtc acggacgttt  22560
cttttatgac tctggatgtg tgtaccaagt atactatcta tggctttaaa ggtgagggta  22620
tcattaccct tacaaattct agctttttgg caggtgttta ttacacatct gattctggac  22680
agttgttagc ctttaagaat gtcactagtg gtgctgttta ttctgttacg ccatgttctt  22740
tttcagagca ggctgcatat gttgatgatg atatagtggg tgttatttct agtttgtcta  22800
gctccacttt taacagtact agggagttgc ctggtttctt ctaccattct aatgatggct  22860
ctaattgtac agagcctgtg ttggtgtata gtaacatagg tgtttgtaaa tctggcagta  22920
ttggctacgt cccatctcag tctggccaag tcaagattgc acccacggtt actgggaata  22980
ttagtattcc caccaacttt agtatgagta ttaggacaga atatttacag ctttacaaca  23040
cgcctgttag tgttgattgt gccacatatg tttgtaatgg taactctcgt tgtaaacaat  23100
tactcaccca gtacactgca gcatgtaaga ccatagagtc agcattacaa ctcagcgcta  23160
ggcttgagtc tgttgaagtt aactctatgc ttactatttc tgatgaggct ctacagttag  23220
ctaccattag ttcgtttaat ggtgatggat ataattttac taatgtgctg ggtgtttctg  23280
tgtatgatcc tgcaagtggc agggtggtaa agaagaggtc ttttattgaa gacctgcttt  23340
ttaataaagt ggttactaat ggccttggta ctgttgatga agactataag cgctgttcta  23400
atggtcgctc tgtggcagat ctagtctgtg cacagtatta ctctggtgtc atggtactac  23460
ctggtgttgt tgacgctgag aagcttcaca tgtatagtgc gtctctcatc ggtggtatgg  23520
tgctaggagg ttttacttct gcagcggcat tgccttttag ctatgctgtt caagctagac  23580
tcaattatct tgctctacag acggatgttc tacagcggaa ccagcaattg cttgctgagt  23640
cttttaactc tgctattggt aatataactt cagcctttga gagtgttaaa gaggctatta  23700
gtcaaacttc caagggtttg aacactgtgg ctcatgcgct tactaaggtt caagaggttg  23760
ttaactcgca gggtgcagct ttgactcaac ttaccgtaca gctgcaacac aacttccaag  23820
ccatttctag ttctattgat gacatttact ctcgactgga cattctttca gccgatgctc  23880
aggttgaccg tctcatcacc ggcagattat cagcacttaa tgcttttgtt gctcaaaccc  23940
tcactaagta tactgaggtt caggctagca ggaagttagc acagcaaaag gttaatgagt  24000
gcgttaaatc gcaatctcag cgttatggtt tttgtggtgg tgatggcgag cacattttct  24060
ctctggtaca ggcagcacct cagggcctgc tgtttttaca tacagtactt gtaccgagtg  24120
attttgtaga tgttattgcc atcgctggct tatgcgttaa cgatgaaatt gccttgactc  24180
tacgtgagcc tggcttagtc ttgtttacgc atgaacttca aaatcatact gcgacggaat  24240
attttgtttc atcgcgacgt atgtttgaac ctagaaaacc taccgttagt gattttgttc  24300
aaattgagag ttgtgtggtc acctatgtca atttgactag agaccaacta ccagatgtaa  24360
tcccagatta catcgatgtt aacaaaacac tttatgagat tttagcttct ctgcccaata  24420
gaactggtcc aagtcttcct ttagatgttt ttaatgccac ttatcttaat ctcactggtg  24480
aaattgcaga tttagagcag cgttcagagt ctctccgtaa tactacagag gagctccaaa  24540
gtcttatata taatatcaac aacacactag ttgaccttga gtggctcaac cgagttgaga  24600
catatatcaa gtggccgtgg tgggtttggt tgattatttt cattgttctc atctttgttg  24660
tgtcattact agtgttctgc tgcatttcca cgggttgttg tggatgctgc ggctgctgct  24720
gtgcttgttt ctcaggttgt tgtaggggtc ctagacttca accttacgaa gtttttgaaa  24780
```

```
aggtccacgt gcagtgatgt ttcttggact ttttcaatac acgattgaca cagttgtcaa  24840
agatgtctca aagtctgcta acttgtcttt ggatgctgtc caagagttgg agctcaatgt  24900
agttccaatt agacaagctt caaatgtgac gggttttctt ttcaccagtg tttttatcta  24960
cttctttgca ctgtttaaag cgtcttcttt gaggcgcaat tatattatgt tggcagcgcg  25020
ttttgctgtc attgttcttt attgcccact tttatattat tgtggtgcat ttttagatgc  25080
aactattatt tgttgcacac ttattggcag gctttgttta gtctgctttt actcctggcg  25140
ctataaaaat gcgctcttta ttatttttaa tactacgaca ctttctttcc tcaatggtaa  25200
agcagcttat tatgacggca aatccattgt gattttagaa ggtggtgacc attacatcac  25260
ttttggcaac tcttttgttg cttttgttag tagcatcgac ttgtatctag ctatacgtgg  25320
gcggcaagaa gctgacctac agctgttgcg aactgttgag cttcttgatg gcaagaagct  25380
ttatgtcttt tcgcaacatc aaattgttgg cattactaat gctgcatttg actcaattca  25440
actagacgag tatgctacaa ttagtgaatg ataatggtct agtagttaat gttatacttt  25500
ggcttttcgt actctttttc ctgcttatta taagcattac tttcgtccaa ttggttaatc  25560
tgtgcttcac ttgtcaccgg ttgtgtaata gcgcagttta cacacctata gggcgtttgt  25620
atagagttta taagtcttac atgcaaatag accccctcct tagtactgtt attgacgtat  25680
aaacgaaata tgtctaacgg ttctattccc gttgatgagg tgattcaaca ccttagaaac  25740
tggaatttca catggaatat catactgacg atactacttg tagtgcttca gtatggccat  25800
tacaagtact ctgcgttctt gtatggtgtc aagatggcta ttctatggat actttggcct  25860
cttgtgttag cactgtcact tttgatgca tgggctagct ttcaggtcaa ttgggtcttt  25920
tttgctttca gcatccttat ggcttgcatc actcttatgc tgtggataat gtactttgtc  25980
aatagcattc ggttgtggcg caggacacat tcttggtggt ctttcaatcc tgaaacagac  26040
gcgcttctca ctacttctgt gatgggccga caggtctgca ttccagtgct tggagcacca  26100
actggtgtaa cgctaacact ccttagtggt acattgcttg tagagggcta taaggttgct  26160
actggcgtac aggtaagtca attacctaat ttcgtcacag tcgccaaggc cactacaaca  26220
attgtctacg gacgtgttgg tcgttcagtc aatgcttcat ctggcactgg ttgggctttc  26280
tatgtccggt ccaaacacgg cgactactca gctgtgagta atccgagttc ggttctcaca  26340
gatagtgaga aagtgcttca tttagtctaa acagaaactt tatggcttct gtcagttttc  26400
aggatcgtgg ccgcaaacgg gtgccattat ccctctatgc ccctcttagg gttactaatg  26460
acaaacccct ttctaaggta cttgcaaata atgctgtacc cactaataaa ggaaataagg  26520
accagcaaat tggatactgg aatgagcaaa ttcgctggcg catgcgccgt ggtgagcgaa  26580
ttgaacaacc ttccaattgg catttctact acctcggaac aggacctcac gccgacctcc  26640
gctataggac tcgtactgag ggtgttttct gggttgctaa agaaggcgca aagactgaac  26700
ccactaacct gggtgtcaga aaggcgtctg aaaagccaat tattccaaat ttctctcaac  26760
agcttcccag cgtagttgag attgttgaac ctaacacacc tcctacttca cgtgcaaatt  26820
cacgtagcag gagtcgtggt aatggcaaca acaggtccag atctccaagt aacaacagag  26880
gcaataacca gtcccgcggt aattcacaga atcgtggaaa taaccagggt cgtggagctt  26940
ctcagaacag aggaggcaat aataataaca ataacaagtc tcgtaaccag tccaagaaca  27000
gaaaccagtc aaatgaccgt ggtggtgtaa catcacgcga tgatctggtg gctgctgtca  27060
aggatgccct taaatctttg ggtattggcg aaaaccctga caagcttaag caacagcaga  27120
agcccaaaca ggaaaggtct gacagcagcg gcaaaaatac acctaagaag aacaaatcca  27180
```

-continued

```
gagccacttc gaaagaacgt gacctcaaag acatcccaga gtggaggaga attcccaagg  27240
gcgaaaatag cgtagcagct tgcttcggac ccaggggagg cttcaaaaat tttggagatg  27300
cggaatttgt cgaaaaaggt gttgatgcct caggctatgc tcagatcgcc agtttagcac  27360
caaatgttgc agcattgctc tttggtggta atgtggctgt tcgtgagcta gcggactctt  27420
acgagattac atataattat aaaatgactg tgccaaagtc tgatccaaat gtagagcttc  27480
ttgtttcaca ggtggatgca tttaaaactg ggaatgcaaa accccagaga aagaaggaaa  27540
agaagaacaa gcgtgaaacc acgcagcagc tgaatgaaga ggccatctac gatgatgtgg  27600
gtgtgccatc tgatgtgact catgccaatt tggaatggga cacagctgtt gatggtggtg  27660
acacggccgt tgaaattatc aacgagatct tcgacacagg aaattaaaca atgtttgact  27720
ggcttatcct ggctatgtcc cagggtagtg ccattacact gttattactg agtgtttttc  27780
tagcgacttg gctgctgggc tatggctttg ccctctaact agcggtcttg gtcttgcaca  27840
caacggtaag ccagtggtaa tgtcagtgca agaaggatat taccatagca ctgtcatgag  27900
gggaacgcag taccttttca tctaaacctt tgcacgagta atcaaagatc cgcttgacga  27960
gcctatatgg aagagcgtgc caggtatttg actcaaggac tgttagtaac tgaagacctg  28020
acggtgttga tatggataca caaaaaaaaa aaaaaaaaaa aa                     28062
```